US011738219B2

(12) United States Patent
Bergeron et al.

(10) Patent No.: US 11,738,219 B2
(45) Date of Patent: *Aug. 29, 2023

(54) RESPIRATOR MASK FOR CBRN OR OTHER PROTECTION

(71) Applicant: AIRBOSS ENGINEERED PRODUCTS INC., Newmarket (CA)

(72) Inventors: David Bergeron, Bromont (CA); Alessandro Del Mistro, Bromont (CA); Luc Dionne, Bromont (CA); Charles Langevin-Bouffard, Bromont (CA); Sebastien Lagace, Sherbrooke (CA); Philippe-Alexandre Lefebvre, Trois-Rivieres (CA); Jean-Luc Lemyre, Granby (CA); Jean-Francois Morissette, Saint-Hugues (CA)

(73) Assignee: AIRBOSS ENGINEERED PRODUCTS INC., Newmarket (CA)

( * ) Notice: Subject to any disclaimer, the term of this patent is extended or adjusted under 35 U.S.C. 154(b) by 343 days.

This patent is subject to a terminal disclaimer.

(21) Appl. No.: 16/525,697

(22) Filed: Jul. 30, 2019

(65) Prior Publication Data

US 2021/0106853 A1   Apr. 15, 2021

Related U.S. Application Data

(63) Continuation of application No. 14/786,914, filed as application No. PCT/CA2014/000376 on Apr. 25, 2014, now Pat. No. 10,363,441.

(30) Foreign Application Priority Data

Apr. 25, 2013 (CA) .................................. CA2813954

(51) Int. Cl.
*A62B 23/02* (2006.01)
*A62B 18/08* (2006.01)
(Continued)

(52) U.S. Cl.
CPC .............. *A62B 23/025* (2013.01); *A62B 7/10* (2013.01); *A62B 18/006* (2013.01); *A62B 18/02* (2013.01);
(Continued)

(58) Field of Classification Search
CPC ........ A61M 16/06; A62B 23/025; A62B 7/10; A62B 18/02; A62B 18/08; A62B 18/082; A62B 18/10; A62B 19/00
See application file for complete search history.

(56) References Cited

U.S. PATENT DOCUMENTS 2,201,315 A * 5/1940 William ............... A62B 23/025
128/206.16
4,453,544 A * 6/1984 Silverthorn ............ A62B 18/08
128/206.15
(Continued)

*Primary Examiner* — Timothy A Stanis
(74) *Attorney, Agent, or Firm* — Tanner IP, PLLC

(57) ABSTRACT

A respirator mask wearable by a wearer for protecting the wearer against inhalation of noxious agents (e.g., chemical agents, biological agents, radiological agents, and/or other poisonous or otherwise harmful agents that can cause disease, injury or death), such as a CBRN mask, may be configured to enhance protection of the wearer (e.g., by providing ballistic protection in addition to protecting against noxious agent inhalation) while reducing a burden on the wearer, such as by reducing respiratory resistance, improving visibility, and/or facilitating use of the mask (e.g., connection or disconnection of a filter, conduit, or other air-providing device to or from a breathing interface of the mask).

16 Claims, 49 Drawing Sheets

(51) Int. Cl.
*A62B 19/00* (2006.01)
*A62B 18/10* (2006.01)
*A62B 7/10* (2006.01)
*A62B 18/00* (2006.01)
*A62B 18/02* (2006.01)
*A61M 16/06* (2006.01)

(52) U.S. Cl.
CPC ............ *A62B 18/08* (2013.01); *A62B 18/082* (2013.01); *A62B 18/10* (2013.01); *A62B 19/00* (2013.01); *A61M 16/06* (2013.01)

(56) References Cited

U.S. PATENT DOCUMENTS

| | | | | |
|---|---|---|---|---|
| 6,543,450 B1* | 4/2003 | Flynn | ..................... | A62B 18/02 |
| | | | | 128/201.25 |
| 6,763,830 B1* | 7/2004 | Davis | ..................... | A62B 18/08 |
| | | | | 128/201.24 |
| 6,860,267 B2* | 3/2005 | Capon | ..................... | A62B 23/02 |
| | | | | 128/206.15 |
| 2007/0277829 A1* | 12/2007 | Casewell | ............... | A62B 18/02 |
| | | | | 128/206.24 |
| 2014/0115864 A1* | 5/2014 | Patil | ..................... | A62B 18/082 |
| | | | | 29/453 |

* cited by examiner

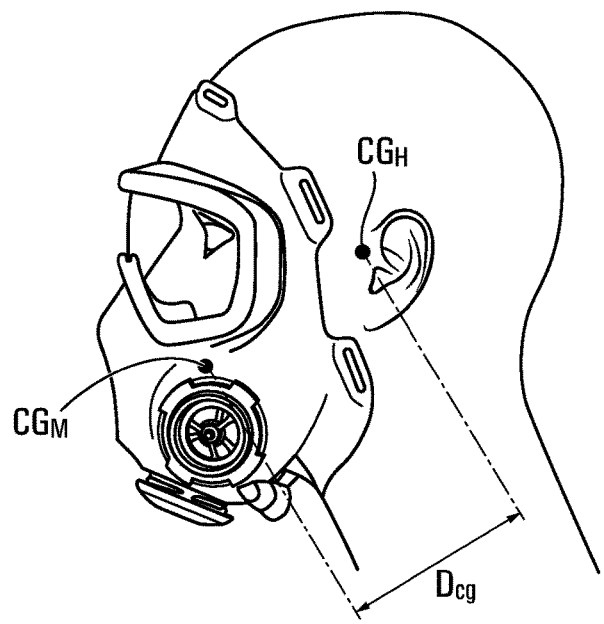
FIG. 17A
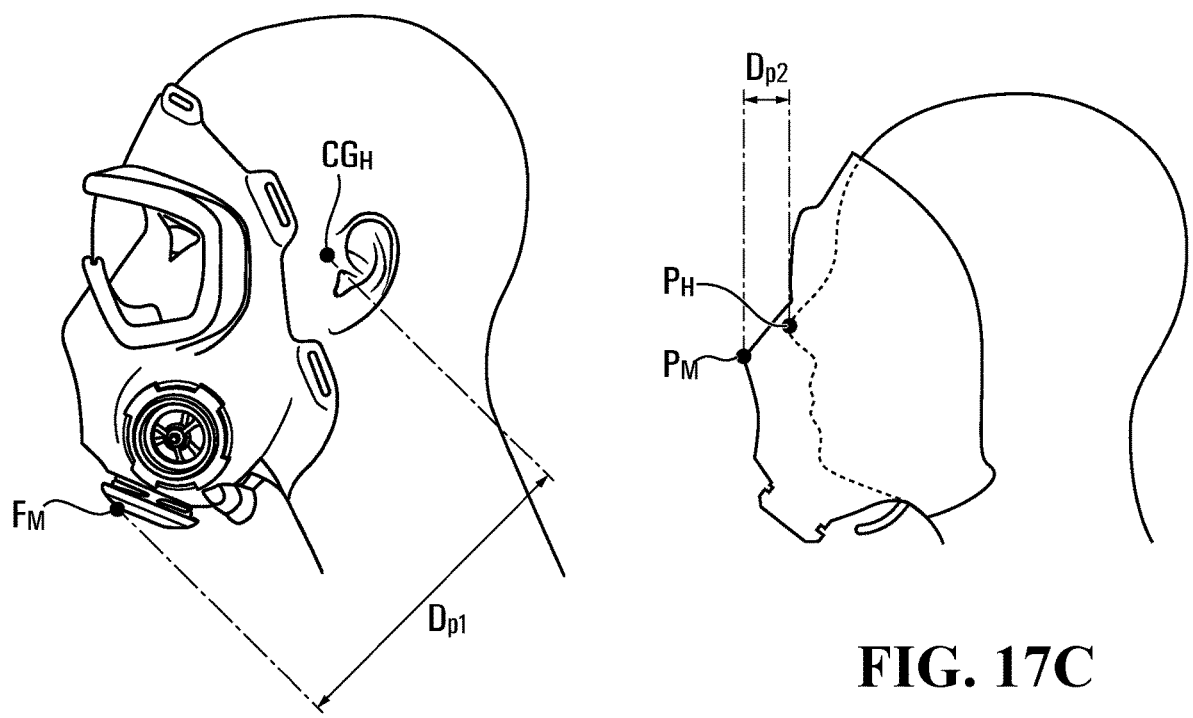
FIG. 17B
FIG. 17C

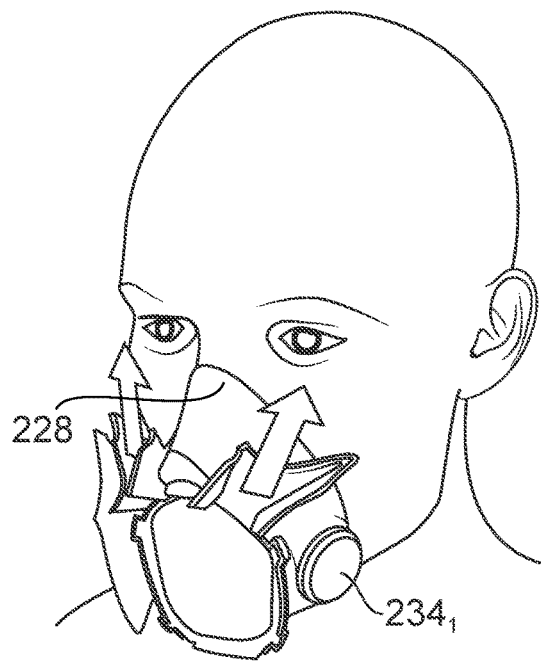
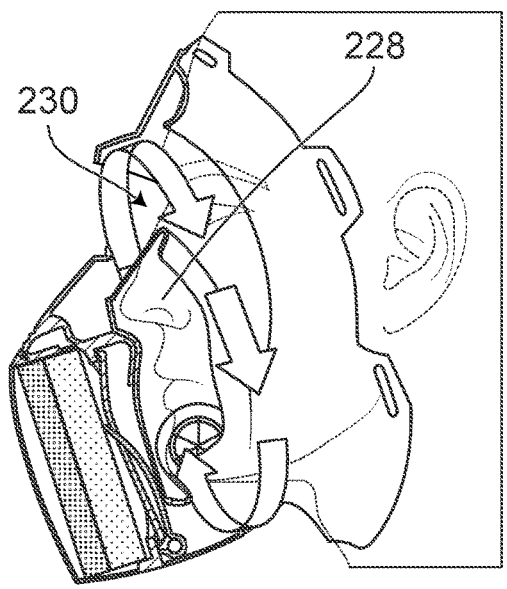
FIG. 30E  FIG. 30F
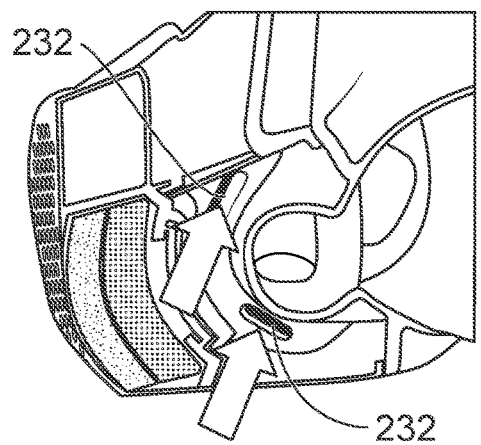
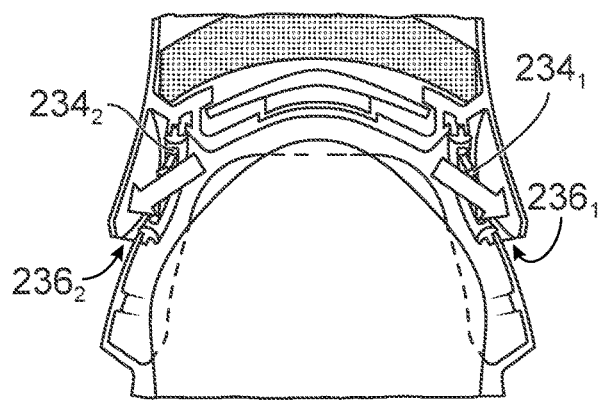
FIG. 30G  FIG. 30H

RESPIRATOR MASK FOR CBRN OR OTHER PROTECTION

RELATED APPLICATIONS

This application is a continuation application of U.S. Ser. No. 14/786,914, filed Oct. 23, 2015, which is a National Stage Application of PCT/CA2014/000376, filed Apr. 25, 2014, which claims priority to CA 2813954, filed Apr. 25, 2013, the contents of all of which are hereby incorporated herein by reference.

FIELD

The invention relates generally to respirator masks for chemical, biological, radiological and nuclear (CBRN) protection and other applications.

BACKGROUND

Respirator masks, sometimes referred to as "gas masks", are used extensively in chemical, biological, radiological and nuclear (CBRN) defense and other applications (e.g., other military, industrial or police applications) to protect a wearer against inhalation of noxious agents (e.g., chemical agents, biological agents, radiological agents, and/or other poisonous or otherwise harmful agents that can cause disease, injury or death). These masks may also provide protection for the wearer's eyes and/or skin.

It is typically desirable to have a respirator mask which, besides protecting its wearer, will minimally affect comfort and/or performance of the wearer. For example, low respiratory resistance is important to avoid making it difficult for the wearer to properly breathe. As another example, lightness or proper weight distribution of the mask is usually desirable such that the wearer is not overburdened with unnecessary weight or a significant weight imbalance on his/her head. Other factors that can often be relevant include visibility, ease of use, and airflow management.

For these and other reasons, there is a need for improvements in respirator masks that can be used in CBRN defense and other applications.

SUMMARY

According to various aspects of the invention, there is provided a respirator mask wearable by a wearer for protecting the wearer against inhalation of noxious agents (e.g., a CBRN mask), wherein the respirator mask may be configured to enhance protection of the wearer (e.g., by providing ballistic protection) and/or reduce a burden on the wearer (e.g., by reducing respiratory resistance, improving visibility, and/or facilitating use of the mask).

For example, according to an aspect of the invention, there is provided a respirator mask for protecting a wearer against inhalation of noxious agents. The respirator mask comprises a facepiece, a visor connected to the facepiece, and a filter mount for mounting a filter to the respirator mask. The filter mount allows a plurality of different types of filters to be mounted to the filter mount.

According to another aspect of the invention, there is provided a respirator mask for protecting a wearer against inhalation of noxious agents. The respirator mask comprises a facepiece, a visor connected to the facepiece, and a mount for mounting an air-providing device to the respirator mask. The mount allows a plurality of different types of air-providing devices to be mounted to the mount. The mount comprises a plurality of connectors that are different from one another to connect respective ones of the different types of air-providing devices.

According to another aspect of the invention, there is provided a respirator mask for protecting a wearer against inhalation of noxious agents. The respirator mask comprises a facepiece, a visor connected to the facepiece, and a mount for mounting an air-providing device to the respirator mask. The mount comprises a valve to regulate airflow within the respirator mask. The valve is configured to remain open while the air-providing device is connected to the mount.

According to another aspect of the invention, there is provided a respirator mask for protecting a wearer against inhalation of noxious agents. The respirator mask comprises a facepiece, a visor connected to the facepiece, and a mount for mounting an air-providing device to the respirator mask. The mount comprises a valve to regulate airflow within the respirator mask. The valve is configured to automatically close in response to the air-providing device being disconnected from the filter mount.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens. The lens is panoramic and comprises a rigid material providing ballistic protection. The lens is curved in a transversal direction of the lens and in a vertical direction of the lens.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens. The lens is panoramic and comprises a rigid material providing ballistic protection. The lens comprises a recess in a nose region of the lens.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens. The lens is panoramic and comprises a rigid material providing ballistic protection. The lens comprises enlarged portions and a constricted portion that is narrower than and interconnects the enlarged portions.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens having a thickness that is variable.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor is removable from the respirator mask.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. A distance between a center of gravity of the respirator mask and a center of gravity of the wearer's head represented by a standard headform according to ISO/TS 16976-2:2010 is no more than 85 mm.

According to another aspect of the invention, there is provided respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens that is panoramic. A distance between a center of gravity of the respirator mask and a center of gravity of the wearer's head represented by a standard headform according to ISO/TS 16976-2:2010 is no more than 85 mm.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. A greatest distance from the respirator mask to a center of gravity of the wearer's head represented by a standard headform according to ISO/TS 16976-2:2010 is no more than 175 mm.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens that is panoramic. A greatest distance from the respirator mask to a center of gravity of the wearer's head represented by a standard headform according to ISO/TS 16976-2:2010 is no more than 175 mm.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. A horizontal distance between a frontmost point of the respirator mask and a frontmost point of the wearer's head represented by a standard headform according to ISO/TS 16976-2:2010 is no more than 27 mm.

According to another aspect of the invention, there is provided a respirator mask for protecting a wearer against inhalation of noxious agents. The respirator mask comprises a facepiece, a breathing interface connected to the facepiece for allowing the wearer to breathe clean air, and a visor connected to the facepiece. The visor comprises a lens that is panoramic. A horizontal distance between a frontmost point of the respirator mask and a frontmost point of the wearer's head represented by a standard headform according to ISO/TS 16976-2:2010 is no more than 27 mm.

According to another aspect of the invention, there is provided a respirator mask for protecting a wearer against inhalation of noxious agents. The respirator mask comprises a facepiece, a breathing interface connected to the facepiece for allowing the wearer to breathe clean air, a visor connected to the facepiece, and a harness connected to the facepiece for securing the respirator mask to the wearer's head. The harness comprises an adjustment strap to adjust a fit of the respirator mask on the wearer's head. The adjustment strap is pullable towards a front of the wearer's head to tighten the respirator mask on the wearer's head.

According to another aspect of the invention, there is provided a respirator mask for protecting a wearer against inhalation of noxious agents. The respirator mask comprises a facepiece, a breathing interface connected to the facepiece for allowing the wearer to breathe clean air, a visor connected to the facepiece, and a harness connected to the facepiece for securing the respirator mask to the wearer's head. The harness extends to the facepiece along at least a majority of a width of a forehead portion of the facepiece.

According to another aspect of the invention, there is provided a respirator mask for protecting a wearer against inhalation of noxious agents. The respirator mask comprises a facepiece, a breathing interface connected to the facepiece for allowing the wearer to breathe clean air, a visor connected to the facepiece, and a harness connected to the facepiece for securing the respirator mask to the wearer's head. The facepiece comprises an elastomeric material overmolded onto the harness.

According to another aspect of the invention, there is provided a respirator mask for protecting a wearer against inhalation of noxious agents. The respirator mask comprises a facepiece comprising an elastomeric material, a breathing interface connected to the facepiece for allowing the wearer to breathe clean air, a visor connected to the facepiece, and a harness connected to the facepiece for securing the respirator mask to the wearer's head. The facepiece comprises a plurality of anchors receiving the harness. Each anchor comprises an opening receiving a part of the harness and an anchoring element embedded in the elastomeric material adjacent to the opening.

According to another aspect of the invention, there is provided a respirator mask for protecting a wearer against inhalation of noxious agents. The respirator mask comprises a facepiece, a visor connected to the facepiece, and a breathing interface connected to the facepiece for allowing the wearer to breathe clean air. The facepiece comprises a plurality of different materials.

According to another aspect of the invention, there is provided a respirator mask for protecting a wearer against inhalation of noxious agents. The respirator mask comprises a facepiece, a visor connected to the facepiece, and a breathing interface connected to the facepiece for allowing the wearer to breathe clean air. The facepiece comprises a first material for engaging the wearer's head and a second material different from the first material and supporting at least one of the visor and the breathing interface.

According to another aspect of the invention, there is provided a respirator mask for protecting a wearer against inhalation of noxious agents. The respirator mask comprises a facepiece, a visor connected to the facepiece, and a breathing interface connected to the facepiece for allowing the wearer to breathe clean air. The facepiece comprises a polymeric material molded into a shape of at least part of the facepiece and overmolded onto a functional component of the respirator mask.

According to another aspect of the invention, there is provided a respirator mask for protecting a wearer against inhalation of noxious agents. The respirator mask comprises a facepiece, a visor connected to the facepiece, and a filter mount for mounting a conforming filter to the respirator mask such that the conforming filter conforms to part of an external surface of the facepiece.

According to another aspect of the invention, there is provided a conforming filter for a respirator mask to protect a wearer against inhalation of noxious agents. The respirator mask comprises a facepiece, a visor connected to the facepiece, and a filter mount for mounting the conforming filter to the respirator mask. The conforming filter comprises a filtering material and an external surface. The external surface is configured to conform to part of an external surface of the facepiece when the conforming filter is mounted to the filter mount.

According to another aspect of the invention, there is provided a respirator mask for protecting a wearer against inhalation of noxious agents. The respirator mask comprises a facepiece, a visor connected to the facepiece, a breathing interface connected to the facepiece for allowing the wearer to breathe clean air, and a speech transmitter for transmitting the wearer's speech. The speech transmitter is attachable to and detachable from the respirator mask.

According to another aspect of the invention, there is provided a respirator mask for protecting a wearer against inhalation of noxious agents. The respirator mask comprises a facepiece, a visor connected to the facepiece, a breathing interface connected to the facepiece for allowing the wearer to breathe clean air, a first speech transmitter for transmitting the wearer's speech, and a second speech transmitter for transmitting the wearer's speech. The first speech transmitter is fixed to the facepiece and the second speech transmitter is attachable to and detachable from the respirator mask.

According to another aspect of the invention, there is provided a speech transmitter for a respirator mask to protect a wearer against inhalation of noxious agents. The respirator mask comprises a facepiece, a visor connected to the facepiece, and a mount for mounting an air-providing device to the respirator mask. The speech transmitter comprises a speech-transmission unit for transmitting the wearer's speech and a connector connectable to the mount to connect the speech transmitter to the respirator mask.

According to another aspect of the invention, there is provided a respirator mask for protecting a wearer against inhalation of noxious agents. The respirator mask comprises a facepiece, a visor connected to the facepiece, a breathing interface connected to the facepiece for allowing the wearer to breathe clean air, and a hydration interface connected to the facepiece for providing potable liquid to the wearer. The hydration interface comprises a channel for conveying the potable liquid. The channel has a curved configuration in a direction of flow of the potable liquid through the hydration interface.

These and other aspects of the invention will now become apparent to those of ordinary skill in the art upon review of the following description of embodiments of the invention in conjunction with the accompanying drawings.

BRIEF DESCRIPTION OF THE DRAWINGS

A detailed description of embodiments of the invention is provided below, by way of example only, with reference to the accompanying drawings, in which:

FIGS. 17A to 17C show the respirator mask in relation to the wearer's face and a center of gravity of the wearer's head;

FIGS. 30A to 30I show air circulation within the respirator mask of FIGS. 24 and 25.

It is to be expressly understood that the description and drawings are only for the purpose of illustrating certain embodiments of the invention and are an aid for understanding. They are not intended to be a definition of the limits of the invention.

DETAILED DESCRIPTION OF EMBODIMENTS

Figure 1:
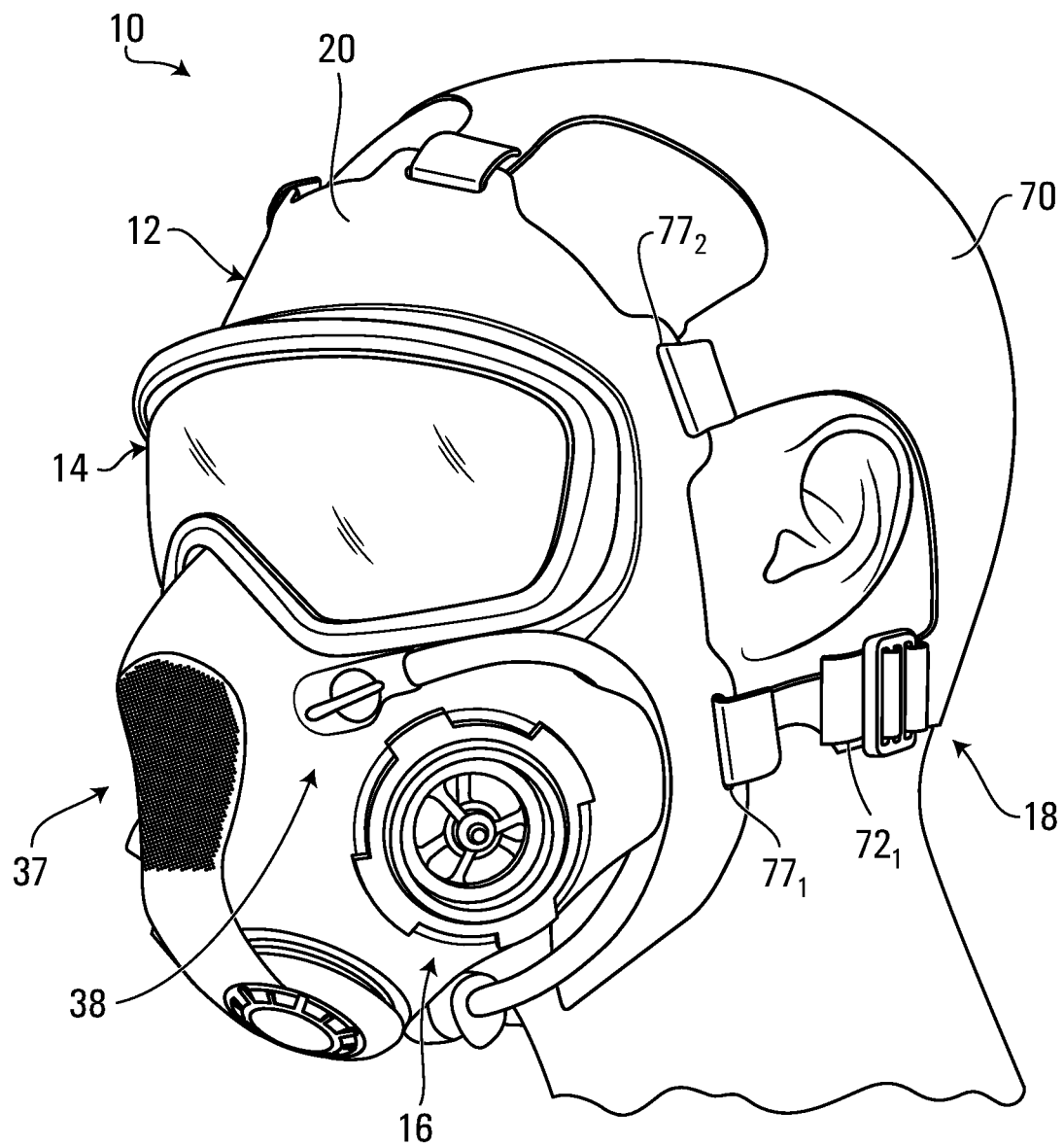
FIGS. 1 and 2 show an example of a respirator mask wearable by a wearer for protecting the wearer against inhalation of noxious agents in accordance with an embodiment of the invention.
Figure 2:
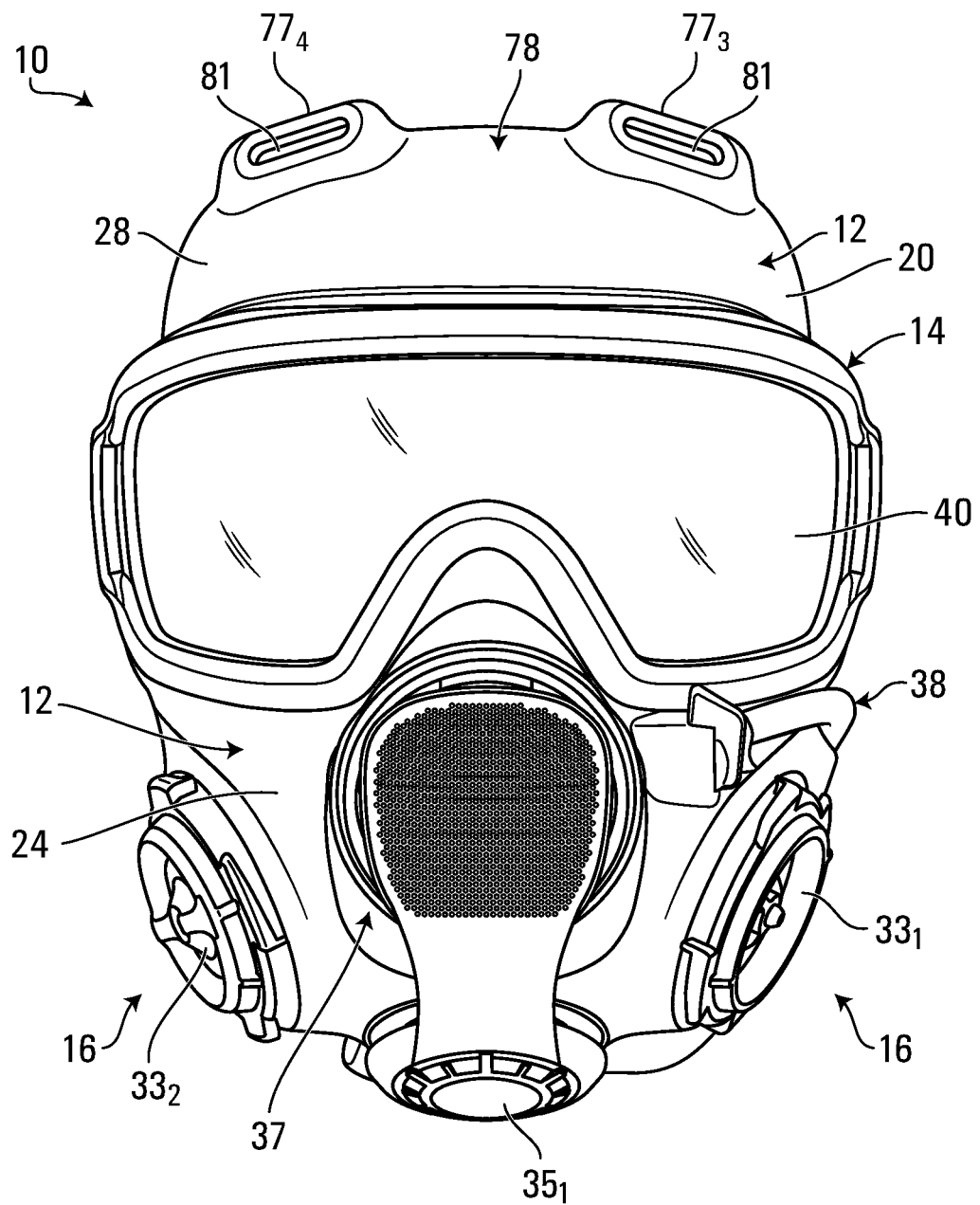

FIGS. 1 and 2 show an example of a respirator mask 10 wearable by a wearer for protecting the wearer against inhalation of noxious agents (e.g., chemical agents, biological agents, radiological agents, and/or other poisonous or otherwise harmful agents that can cause disease, injury or death) in accordance with an embodiment of the invention. In this embodiment, the mask 10 is a chemical, biological, radiological and nuclear (CBRN) respirator mask to protect the wearer who may be exposed to a chemical, biological, radiological or nuclear hazard.

The mask 10 comprises a facepiece 12 for covering at least part of the wearer's face, a visor 14 for allowing the wearer to see, a breathing interface 16 for allowing the wearer to breathe clean air, and a harness 18 for securing the mask 10 to the wearer's head. In this embodiment, the mask 10 also comprises a speech transmitter 37 to transmit the wearer's speech and a hydration interface 38 to provide potable water or other liquid to the wearer.

As further discussed later, in this embodiment, the mask 10 is configured to enhance protection of the wearer (e.g., by providing ballistic protection in addition to protecting against noxious agent inhalation) while reducing a burden on the wearer, such as by reducing respiratory resistance, improving visibility, and/or facilitating use of the mask 10 (e.g., connection or disconnection of a filter, conduit, or other air-providing device to or from the breathing interface 16).

The facepiece 12 overlies at least part of the wearer's face when the mask 10 is worn. Notably, the facepiece 12 extends over the wearer's face such that the mask 10 covers at least the wearer's nose and mouth. In this embodiment, the facepiece 12 also extends over the wearer's chin and forehead as well as lateral sides of the wearer's head. Thus, in this embodiment, the mask 10 may be referred to as a "full-face" mask. In other embodiments, the facepiece 12 may cover a different (e.g., smaller) extent of the wearer's face (e.g., the mask 10 may be a "half-face" mask).

Figure 3:
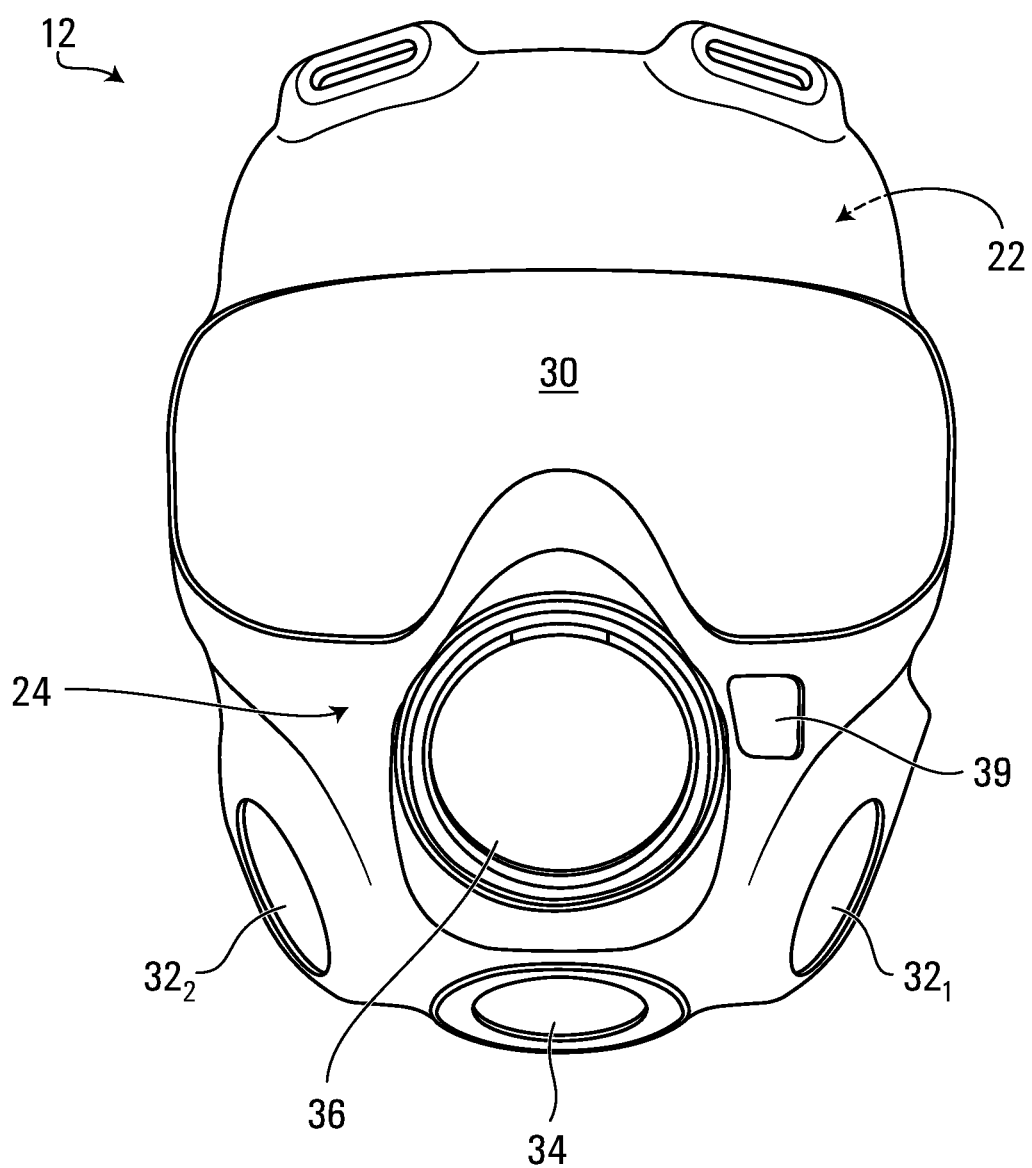
FIG. 3 shows a facepiece of the respirator mask.

More particularly, in this embodiment, with additional reference to FIG. 3, the facepiece 12 comprises a face-engaging portion 20 which engages the wearer's face. The face-engaging portion 20 extends substantially around a perimeter of the wearer's face and includes a sealing surface 22 which creates a seal against the wearer's face.

The facepiece 12 also comprises a support portion 24 supporting components of the mask 10 that are connected to the facepiece 12, including the visor 14, the breathing interface 16, the speech transmitter 37, and the hydration interface 38. More specifically, in this embodiment, the support portion 24 comprises a plurality of openings for accommodating components of the mask 10, including an opening 30 for the visor 14, openings 32$_1$, 32$_2$ for inhalation ports 33$_1$, 33$_2$ of the breathing interface 16, an opening 34 for an exhalation port 35$_1$ of the breathing interface 16, an opening 36 for the speech transmitter 37, and an opening 39 for the hydration interface 38.

In this embodiment, the facepiece 12 comprises a polymeric material 28 molded into a shape of at least part of the facepiece 12. More particularly, in this embodiment, the polymeric material 28 is an elastomeric material. The elastomeric material 28 may be any polymeric material with suitable elasticity. For instance, in various embodiments, the elastomeric material 28 may be a thermoplastic elastomer (e.g., a fluorinated thermoplastic elastomer or any other thermoplastic elastomer) or a thermoset elastomer (e.g., a fluorinated thermoset elastomer or any other thermoset elastomer). In this example of implementation, the elastomeric material 28 is a rubber material. More specifically, in this example, the rubber material 28 is a butyl rubber. Any other suitable rubber compound may be used in other examples (e.g., natural rubber, butadiene rubber, styrene butadiene rubber, halogenated butyl rubber, etc.). In this example of implementation, the rubber material 28 is molded into the shape of the facepiece 12 by an injection molding process.

The facepiece 12 may be made of any other suitable material and/or using any other suitable process in other embodiments. For example, in other embodiments, the elastomeric material 28 may be another elastomer instead of rubber (e.g., a polyurethane elastomer, an ethylene elastomer, a propylene elastomer, a nitrile elastomer, an epichlorohydrin elastomer, a polychloroprene elastomer, an ethylene acrylic elastomer, a tetrafluoroethylene elastomer, a tetrafluoropropylene elastomer, a fluoroelastomer, a perfluoroelastomer, etc.). In yet other embodiments, the facepiece 12 may include a polymeric non-elastomeric material or any other suitable polymeric material (e.g., polyethylene, polyamide, polyvinyl chloride, chlorosulphonated polyethylene, chlorinated polyethylene, polyacrylate, polysulfide, silicone, fluorosilicone, etc.). As another example, in other embodiments, the facepiece 12 may be molded into shape by a compression molding process or any other suitable molding process.

Figure 4A:
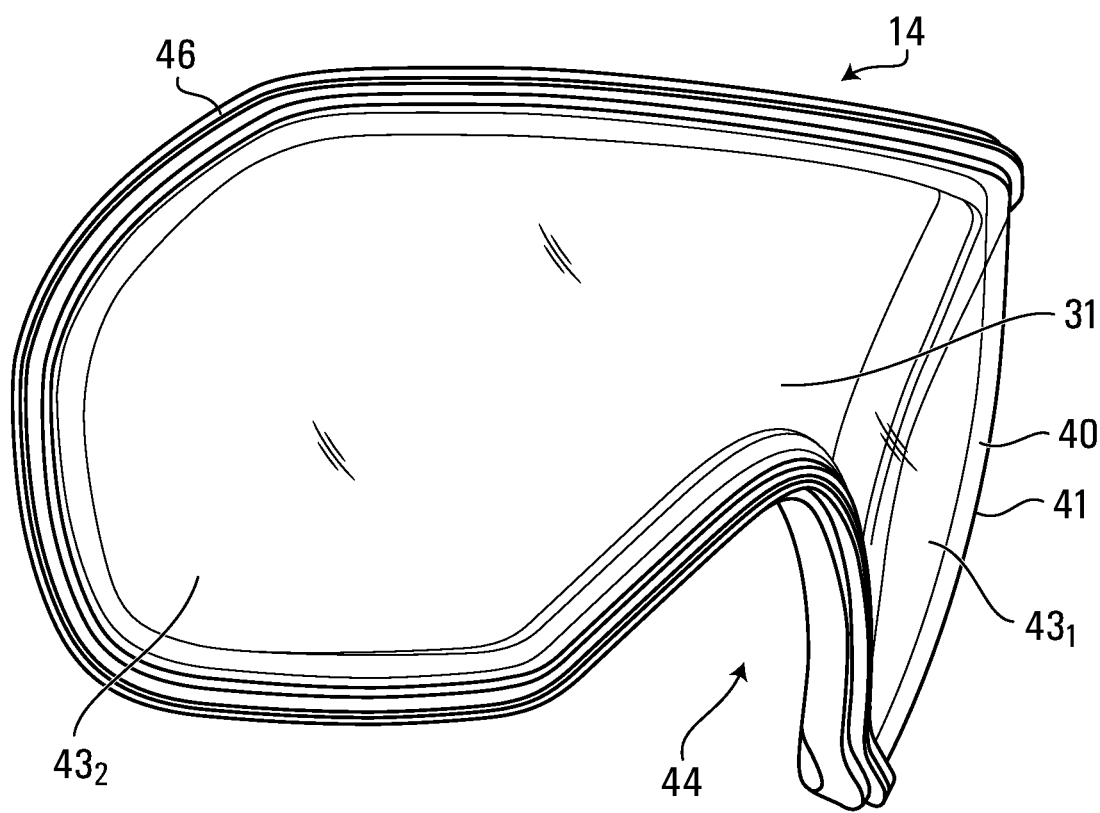
FIGS. 4A and 4B show a visor of the respirator mask and a lens of the visor.

The visor 14 comprises a lens 40 through which the wearer can see. In this embodiment, with additional reference to FIGS. 4A and 4B, the visor 14 is panoramic to enhance the wearer's field of view $F_v$. That is, the lens 40 extends across the mask 10 so as to cover both of the wearer's eyes. For example, in this embodiment, the field of view $F_v$ may span more than 90°, in some cases at least 100°, and in some cases even more (e.g., up to 109° or more). The wearer is thus capable of unobstructed visibility through the lens 40 over that wide angle. The field of view $F_v$ may have any other suitable value in other embodiments. Also, in other embodiments, the visor 14 may comprise two lenses that are separate from one another and cover respective ones of the wearer's eyes.

In this embodiment, the visor 14 provides ballistic protection. For example, in some embodiments, the visor 14 can withstand impacts from objects hitting it at speeds of at least 700 feet per second, in some cases at least 750 feet per second, in some cases 800 feet per second, in some cases at least 850 feet per second, and in some cases even higher speeds. The visor 14 may be able to withstand impacts from objects at any other speeds in other embodiments. For instance, in some embodiments, the visor 14 may meet a ballistic eyewear standard, such as MIL-PRF-31013 or MIL-STD-662.

To that end, in this embodiment, the visor 14 is rigid. More particularly, in this embodiment, the lens 40 is made of a rigid transparent polymeric material 41. For instance, in this example, the rigid polymeric material 41 is polycarbonate, namely an optical-grade polycarbonate. In other examples, the rigid polymeric material 41 may be any other suitable material with sufficient rigidity (e.g., optical-grade polyamide, boron nitride, etc.).

In addition, in this embodiment, outer and inner surfaces 42, 45 of the lens 40 may be coated to improve performance of the visor 14. For example, in this embodiment, the outer surface 42 of the lens 40 is coated with a protective coating, which has a protective effect, such as a hard coat for added mechanical and/or chemical resistance. Furthermore, in this embodiment, the inner surface 45 of the lens 40 is coated with an anti-fogging coating for providing fogging resistance. In this example of implementation, the inner surface 45 is coated with a polysiloxane base coat. In other embodiments, the outer surface 42 and/or the inner surface 45 may be coated with any other suitable coating or may not be coated with any coating.

The visor 14 is shaped to improve visibility and comfort of the wearer. For example, optical properties of the visor 14 may be improved by a curved shape of the visor 14. In this embodiment, the lens 40 has a curvature such that it is curved in a plurality of different directions. More particularly, in this embodiment, with reference to FIGS. 4B and 5B, the curvature of the lens 40 has a first curvature $C_1$ in a transversal direction of the mask 10, which can be referred to as a "transversal" curvature, and a second curvature $C_2$ in a vertical direction of the mask 10, which can be referred to as a "vertical" curvature.

In this example of implementation, the curvature of the lens 40, including its transversal curvature $C_1$ and vertical curvature $C_2$, is based on a polynomial function. This allows a rate of change in curvature of the lens 40 that may improve optical characteristics. For instance, in this case, the polynomial function on which is based the curvature of the lens 40 makes the lens 40 flatter in its front, which may help to reduce prismatic effects on the wearer's eyes when looking towards his/her nose. The polynomial function also results in the curvature increasing and maintaining better angles as the lens 40 turns about the wearer's eye, which may help to reduce prismatic effects on the outboard eye as well. The polynomial function may be more suitable for covering both of the wearer's eyes with less optical distortion effects. Physically, the polynomial function may help the lens 40 fit the wearer's face and eyes better than an arc that bows out in its center.

The polynomial function on which is based the curvature of the lens 40 may take on any suitable form. For example, in some embodiments, an order of the polynomial function may be at least three, in some cases at least six, in some cases at least ten, and in some cases even higher.

Figure 4B:
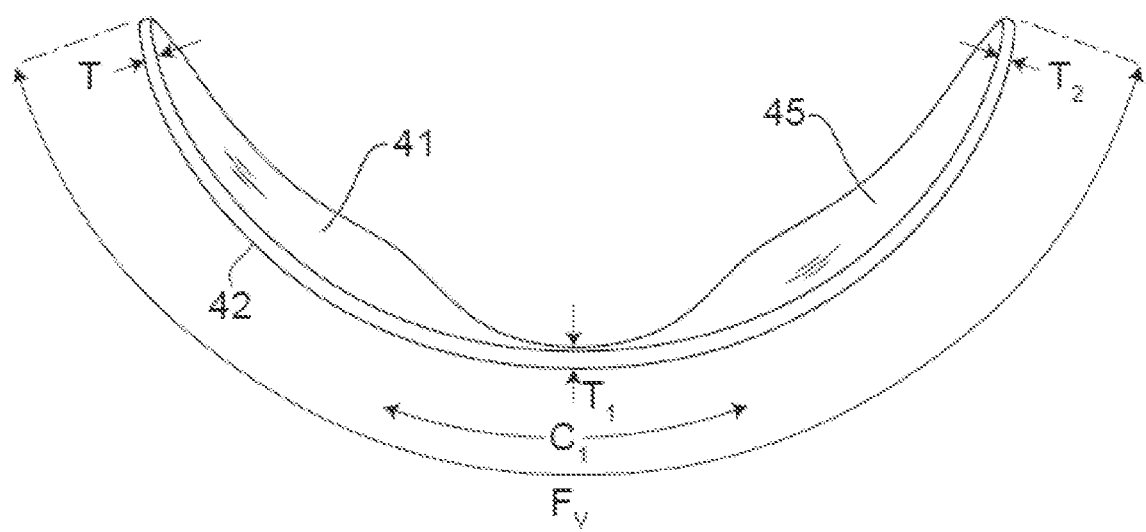

In this embodiment, with additional reference to FIG. 4B, the lens 40 has a variable thickness T, i.e, the thickness T of the lens 40 has different values in certain parts of the lens 40. This can help improve optical properties of the lens 40 by reducing optical aberrations. For example, in this embodiment, the thickness T of the lens 40 varies along a transversal direction of the lens 40. For instance, the thickness T of the lens 40 may have a given value $T_1$ at a first transversal position of the lens 40 and a different (i.e., greater or smaller) value $T_2$ at a second transversal position of the lens 40. In this example, the thickness T of the lens 40 decreases from a central region of the lens 40 towards a lateral end of the lens 40 in the transversal direction of the lens 40. The thickness $T_1$ of the lens 40 is thus greater than the thickness $T_2$ of the lens 40. In some embodiments, the thickness T of the lens 40 may also vary along a vertical direction of the lens 40. For instance, the thickness T of the lens 40 may have a given value $T_3$ at a first vertical position of the lens 40 and a different (i.e., greater or smaller) value $T_4$ at a second vertical position of the lens 40.

For example, in some embodiments, a ratio $T_{max}/T_{min}$ of a maximum value ($T_{max}$) of the thickness T of the lens 40 over a minimum value ($T_{min}$) of the thickness T of the lens 40 may be at least 1.1, in some cases at least 1.15, in some cases at least 1.2, in some cases at least 1.25, and in some cases even more. For instance, in this embodiment, the thickness T of the lens 40 may vary from 2.22 millimeters to 2.98 millimeters. In other embodiments, the range of the thickness T of the lens 40 may be less than or greater than this range. Alternatively or additionally, a mean value of the thickness T of the lens 40 may be different in other embodiments.

In this example of implementation, the lens 40 comprises a recess 44 in a nose region of the lens 40. The recess 44 generally follows a curvature of the wearer's nose and may thus provide a better fit and added comfort to the wearer. The lens 40 includes enlarged portions $43_1$, $43_2$ and a constricted portion 31 that is narrower than and interconnects the enlarged portions $43_1$, $43_2$. The recess 44 extends below the constricted portion 31 and between the enlarged portions $43_1$, $43_2$ of the lens 40.

The lens 40 may be shaped, constructed of any other suitable materials, and/or otherwise configured in any other suitable manner in other embodiments (e.g. an aspheric design or any other suitable design, no recess, etc.).

In this embodiment, the visor 14 is removable from the mask 10. That is, the visor 14 is mounted in the mask 10 such that it can be removed in order to be repaired or replaced by another visor, for example when it is scratched or otherwise damaged.

By "removable", it is meant that the lens 40 of the visor 14 can be removed from the mask 10 without damaging the mask 10 such that the mask 10 remains usable afterwards once the lens 40 is reinstalled in the mask 10 or a replacement lens is installed in the mask 10. In other words, removal of the visor 14 does not destroy or impair the mask 10 such that it can no longer be used afterwards.

More particularly, in this embodiment, the visor 14 comprises a frame 46 mounted to the facepiece 12 and receiving the lens 40. The lens 40 is adhesively bonded to the frame 46 by an adhesive 48 which can be softened and removed by heating it. The adhesive 48 can be softened and removed by heating it to a temperature above an operational temperature range of the mask 10, i.e., above a temperature range in which the mask 10 can be used. For example, in some embodiments, the adhesive 48 can be softened and removed by heating it to a temperature above 70° C., in some cases at least 80° C., in some cases at least 90° C., in some cases at least 100° C., in some cases at least 110° C., in some cases at least 120° C., and in some cases even more. In some situations, the temperature may be no more than 150° C., in some cases no more than 135° C., and in some cases no more than 120° C. The adhesive 48 may be heated to any other suitable temperature range in other embodiments.

In this example of implementation, the frame 46 comprises an inner frame member 47 and an outer frame member 49 which receive the lens 40 between them such that the lens 40 is sandwiched between them.

Figure 5A:
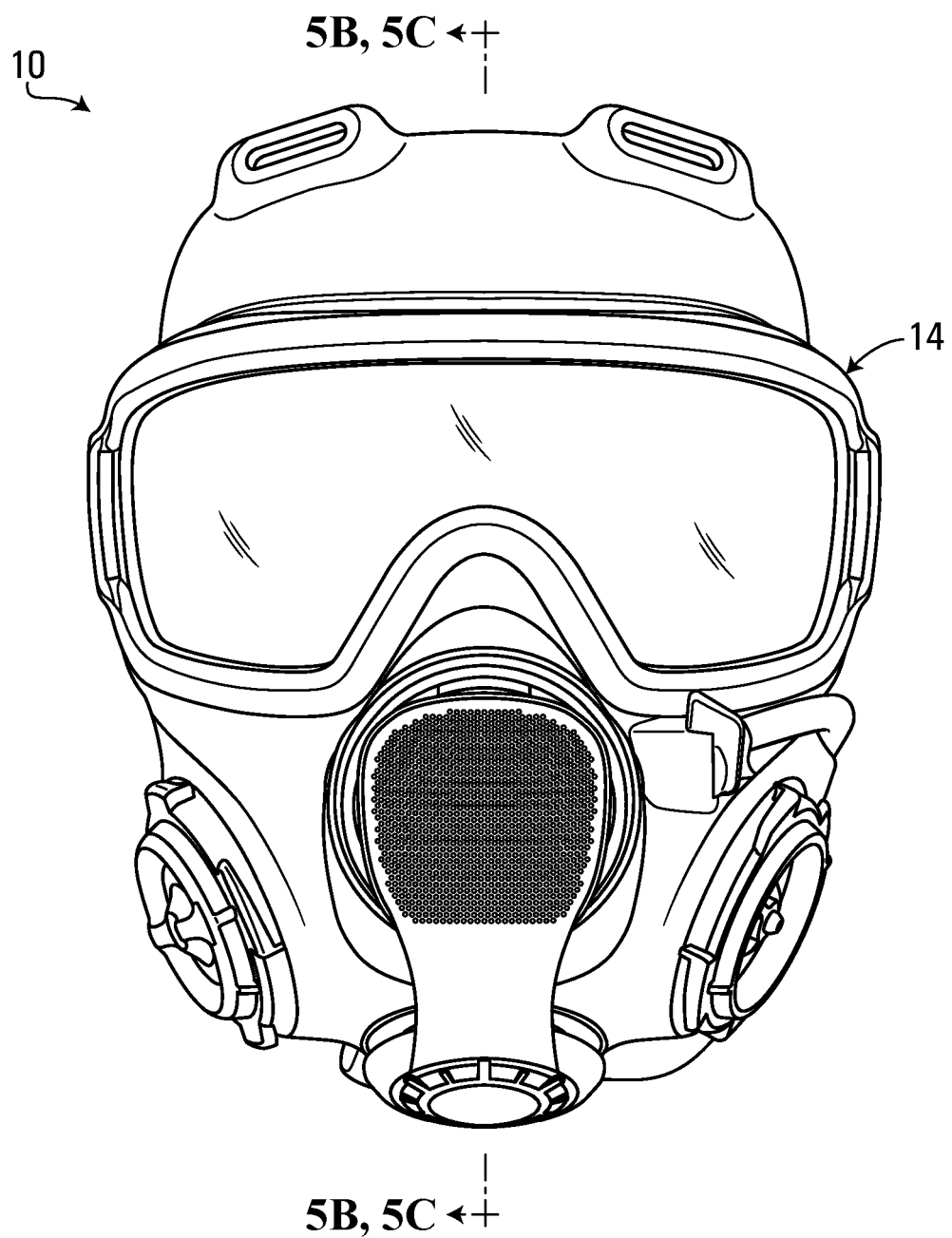
FIGS. 5A to 5D show the visor in the respirator mask.
Figure 5B:
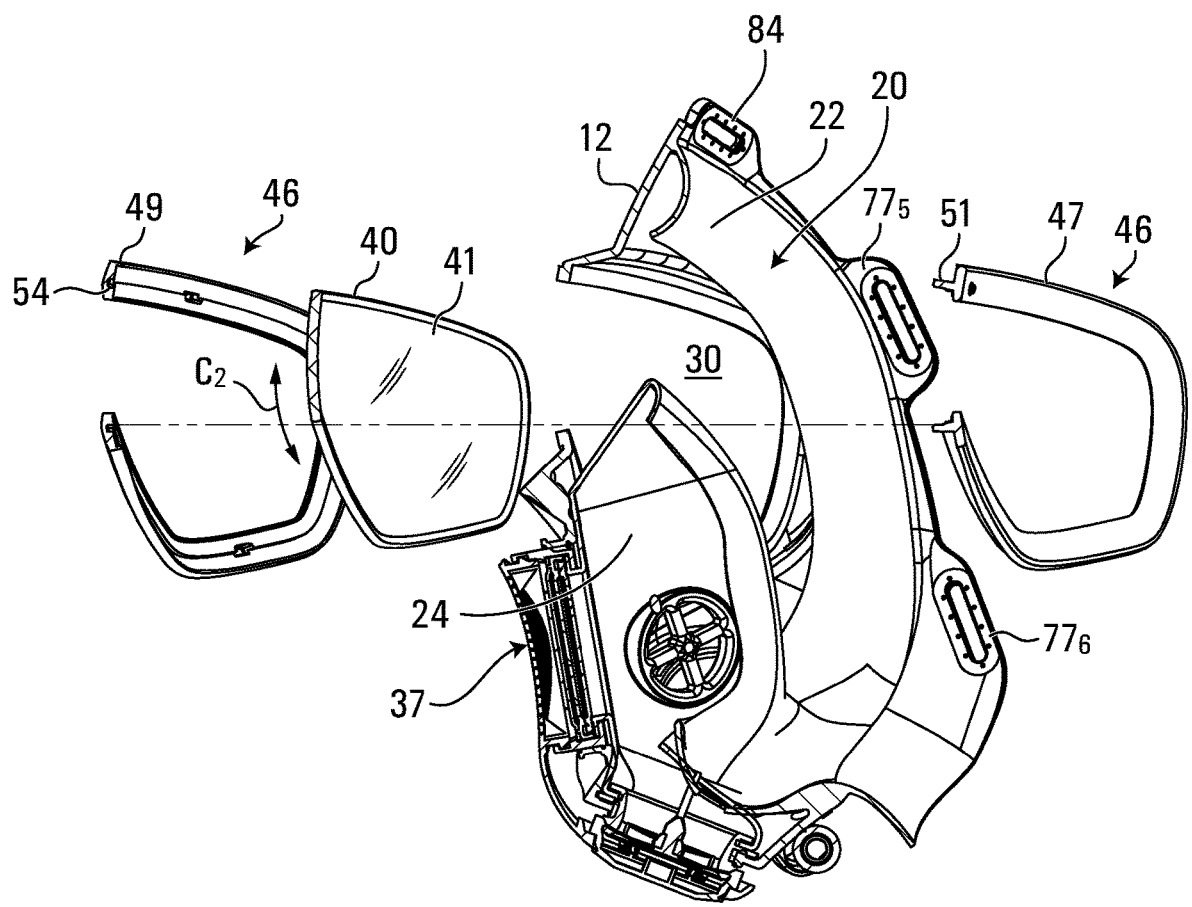
Figure 5D:
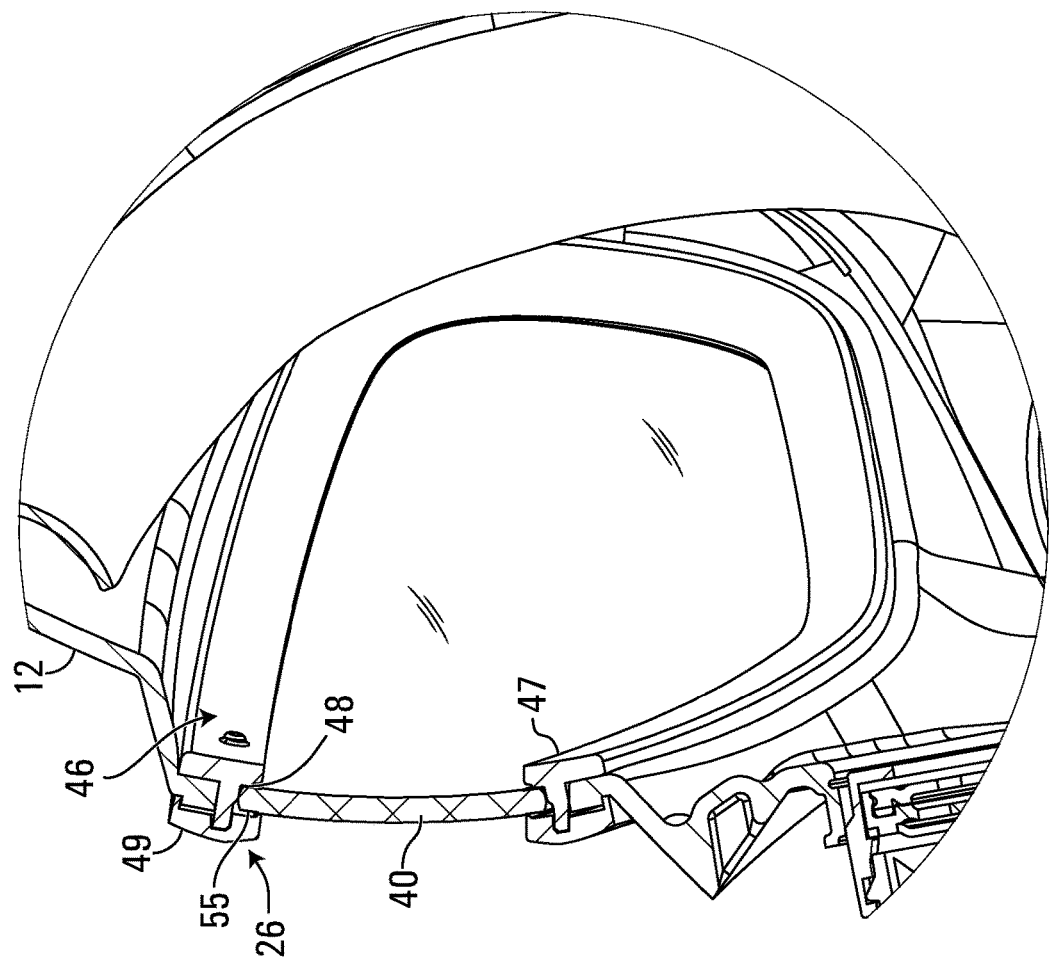
Figure 5C:
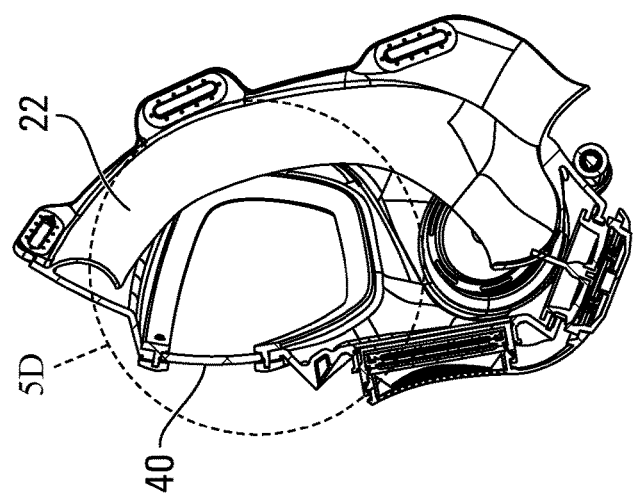

More particularly, in this example, the inner and outer frame members 47, 49 comprise an interlocking mechanism 26 for facilitating an assembly of the inner and outer frame members 47, 49 with the lens 40. As shown in FIGS. 5B and 5D, the interlocking mechanism 26 comprises an interlocking protrusion 51 located on the inner frame member 47, and an interlocking recess 54 located on the outer frame member 49. The interlocking protrusion 51 is directed outwardly towards the outer frame member 49. Conversely, the interlocking recess 54 faces inward towards the inner frame member 49 and is operable to receive therein the interlocking protrusion 51. When assembled, the inner and outer frame members 47, 49 form a recess 55 of appropriate dimensions to receive the lens 40. As shown in FIG. 5D, the lens 40 is placed in the recess 55, between the inner and outer frame members 47, 49.

The interlocking mechanism 26 may be configured in any other way in other embodiments. For instance, the interlocking protrusion 51 and the interlocking recess 54 may be located on the other of the inner and outer frame members 47, 49. Alternatively, in other embodiments, the inner and outer frame members 47, 49 may not comprise any interlocking mechanism at all. For instance, in some embodiments, a recess such as the recess 55 may be formed between the inner and outer frame members 47, 49 without there being an interlocking mechanism.

The adhesive 48 is used in order to bond the lens 40 with the inner and outer frame members 47, 49 of the frame 46. In this embodiment, the adhesive 48 is a reactive polyurethane hot-melt adhesive. The adhesive 48 may be any other suitable adhesive in other embodiments. The adhesive 48 may be applied manually or by a machine (e.g., a robot) for more precise application.

Figure 6:
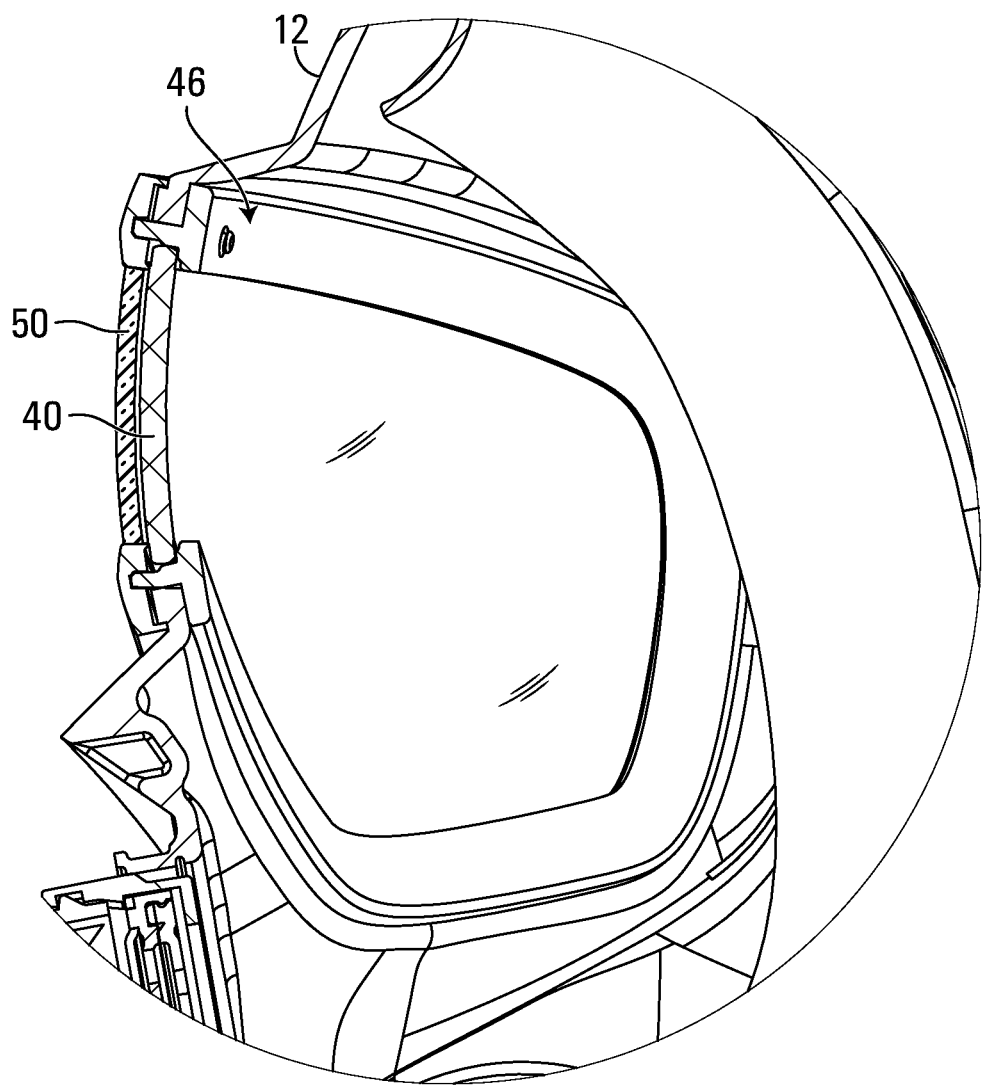
FIG. 6 shows an example of an outsert lens mounted over the visor in accordance with an embodiment of the invention.
Figure 7:
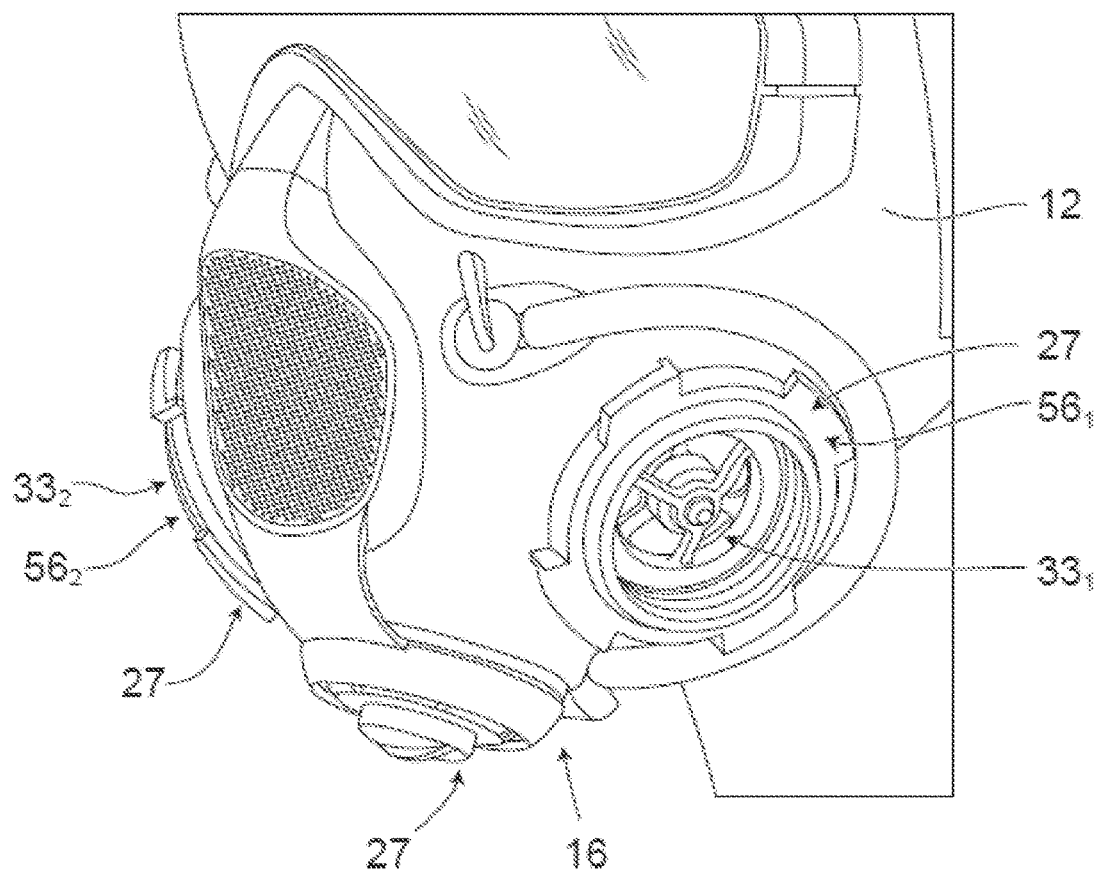
FIGS. 7, 8A to 8K and 9 show a mount of a breathing interface of the respirator mask and different types of air-providing devices mounted to the mount.

With additional reference to FIG. 6, in this embodiment, the visor 14 is configured such that optical properties are maintained when an outsert lens 50 is mounted over the lens 40 (e.g., for glance or laser protection). In this example, this may be achieved by designing curvatures of the lens 40 of the visor 14 and the outsert lens 50 taking into account respective thicknesses of these two lenses.

The visor 14 may be implemented (e.g., shaped, constructed, etc.) in various other ways in other embodiments.

The breathing interface 16 is configured to allow the wearer to breathe safely, despite noxious agents that may be present in the wearer's environment. To that end, with additional reference to FIGS. 7 to 10B, the breathing interface 16 is connectable to an air-providing device 29 configured to provide clean air for the wearer to breathe, i.e., air that is substantially free of noxious agents that may be present in the wearer's environment. In this embodiment, the air-providing device 29 is a filter 52 for filtering ambient air in the wearer's environment to remove noxious agents potentially contained therein so as to provide filtered (or "purified") air within the mask 10 for the wearer to breathe. The mask 10 may thus sometimes be referred to as an "air-filtering" or "air-purifying" mask.

Figure 10A:
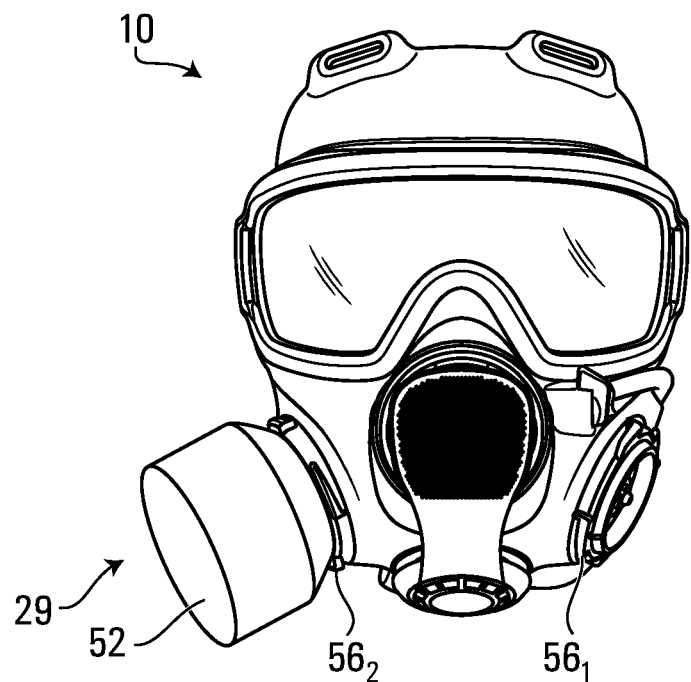
FIGS. 10A, 10B and 11 show different types of air-providing devices mounted to the respirator mask.
Figure 10B:
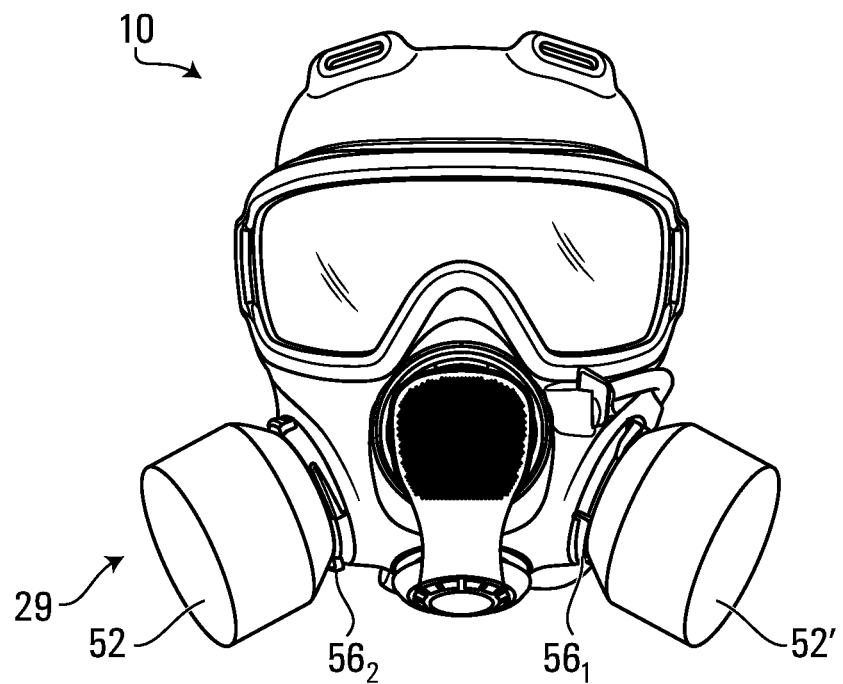

More particularly, in this embodiment, the breathing interface 16 comprises a plurality of mounts $56_1$, $56_2$ for mounting the air-providing device 29 to the mask 10. Since the air-providing device 29 is the filter 52 in this embodiment, the mounts $56_1$, $56_2$ can be referred to as "filter mounts". In this example, the filter mounts $56_1$, $56_2$ are disposed on respective sides of the mask 10. Specifically, in this example, the filter mounts $56_1$, $56_2$ provide the inhalation ports $33_1$, $33_2$ of the breathing interface 16 located in the openings $32_1$, $32_2$ of the facepiece 12. This can allow the filter 52 to be mounted on either side of the mask 10, for instance, according to the wearer's preference or task at hand. Also, in some cases, as shown in FIGS. 10A and 10B, the filter 52 can be mounted to a given one of the filter mounts $56_1$, $56_2$ while a similar filter 52' can be mounted to the other one of the filter mounts $56_1$, $56_2$. This can provide more filtering capacity or longer use of the mask 10.

In this embodiment, each filter mount $56_x$ comprises a valve 65 (e.g., a check valve) to regulate airflow within the mask 10, including air flowing into the mask 10 for breathing by the wearer. The valve 65 is operable in an open state allowing flow of air through the valve 65 for the wearer to inhale and in a closed state preventing flow of air through the valve 65. The valve 65, including its structure and operation, will be discussed further below.

Figure 8A:
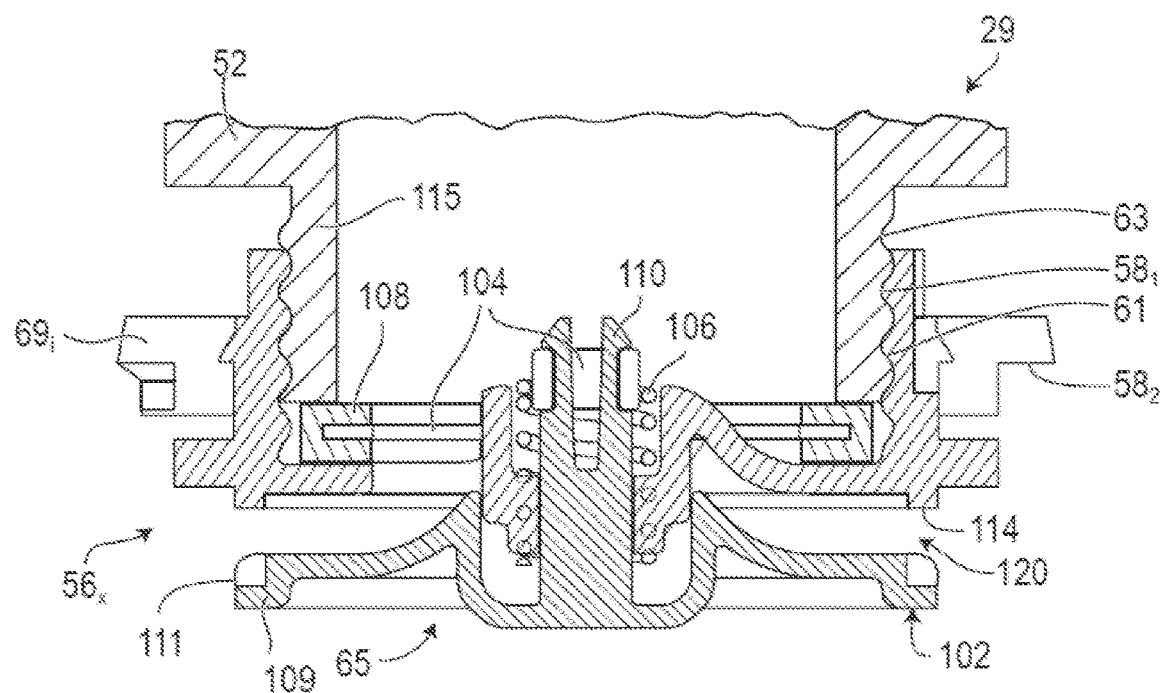
Figure 8B:
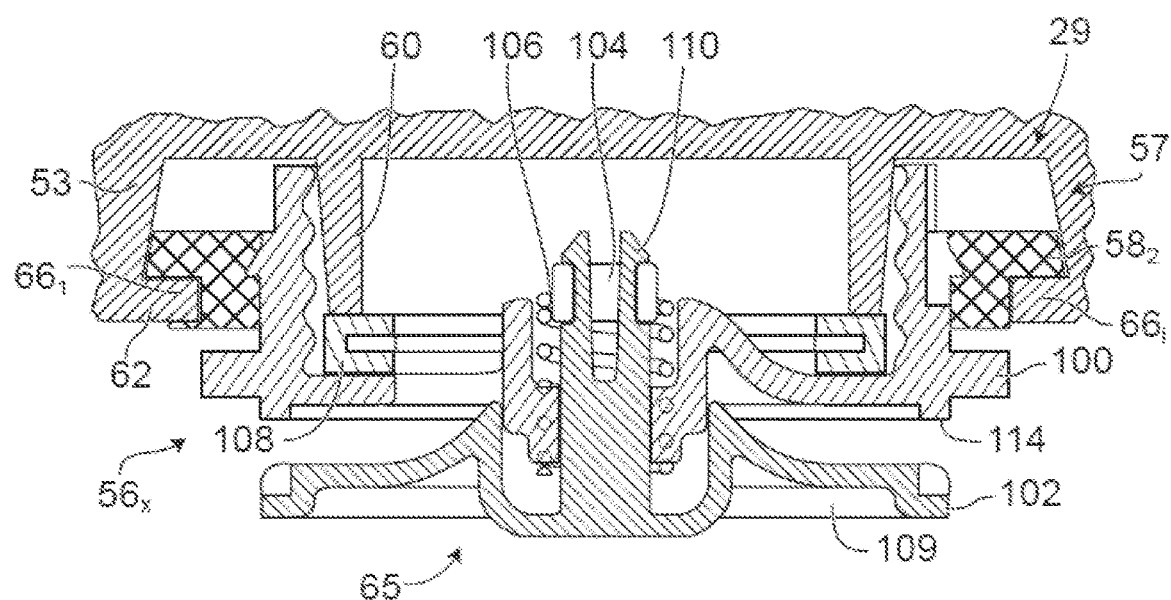
Figure 8C:
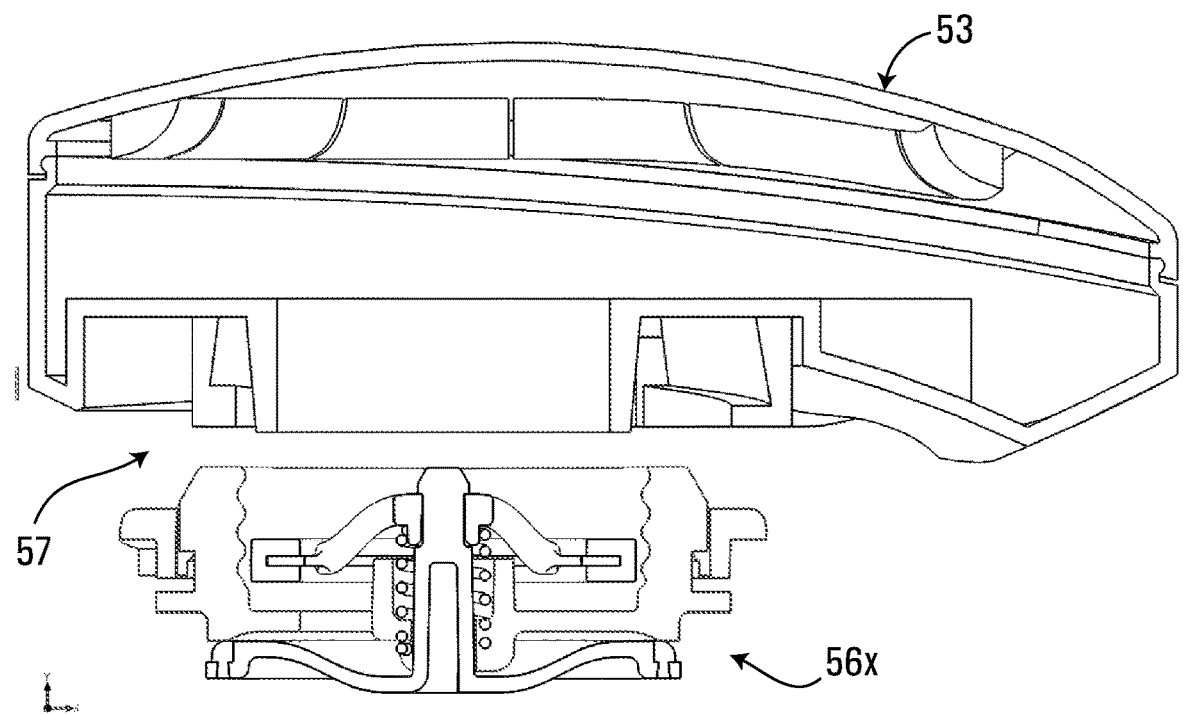

As shown in FIGS. 8A and 8B, in this embodiment, the filter mount $56_x$ is connectable to a plurality of different types of filters, including the filter 52, as shown in FIG. 8A, and another filter 53 of a different type than the filter 52, as shown in FIG. 8B. To that end, in this embodiment, the filter mount $56_x$ comprises a plurality of connectors $58_1$, $58_2$ that are different from one another to connect respective ones of the filters 52, 53. When any one of the filters 52, 53 is connected to a corresponding one of the connectors $58_1$, $58_2$ of the filter mount $56_x$, it interacts with the filter mount $56_x$ so as to operate the valve 65.

More particularly, in this embodiment, the filter 52 is a threaded filter which is securable to the filter mount $56_x$ by being screwed into the filter mount $56_x$. The connector $58_1$ of the filter mount $56_x$ is thus a threaded connector including a thread 61 that is complementary to a thread 63 of the filter 52. In this example, the threaded filter 52 is a standard NATO threaded filter (e.g., with a 40-mm NATO thread). Any other suitable thread may be used in other examples.

Also, in this embodiment, the filter 53 is a threadless filter which is securable to the filter mount $56_x$ without being screwed into the filter mount $56_x$. By "threadless", it is meant that the filter 53 does not have a thread required to retain the filter 53 on the mask 10. Rather, in this embodiment, the filter 53 is a "quick-connect" filter. More particularly, in this embodiment, the filter 53 is connectable to the filter mount $56_x$ by being pushed into the filter mount $56_x$ and subsequently secured thereto. To that end, the filter 53 comprises a mounting structure 57 operable to engage the connector $58_2$ of the filter mount $56_x$.

Figure 8D:
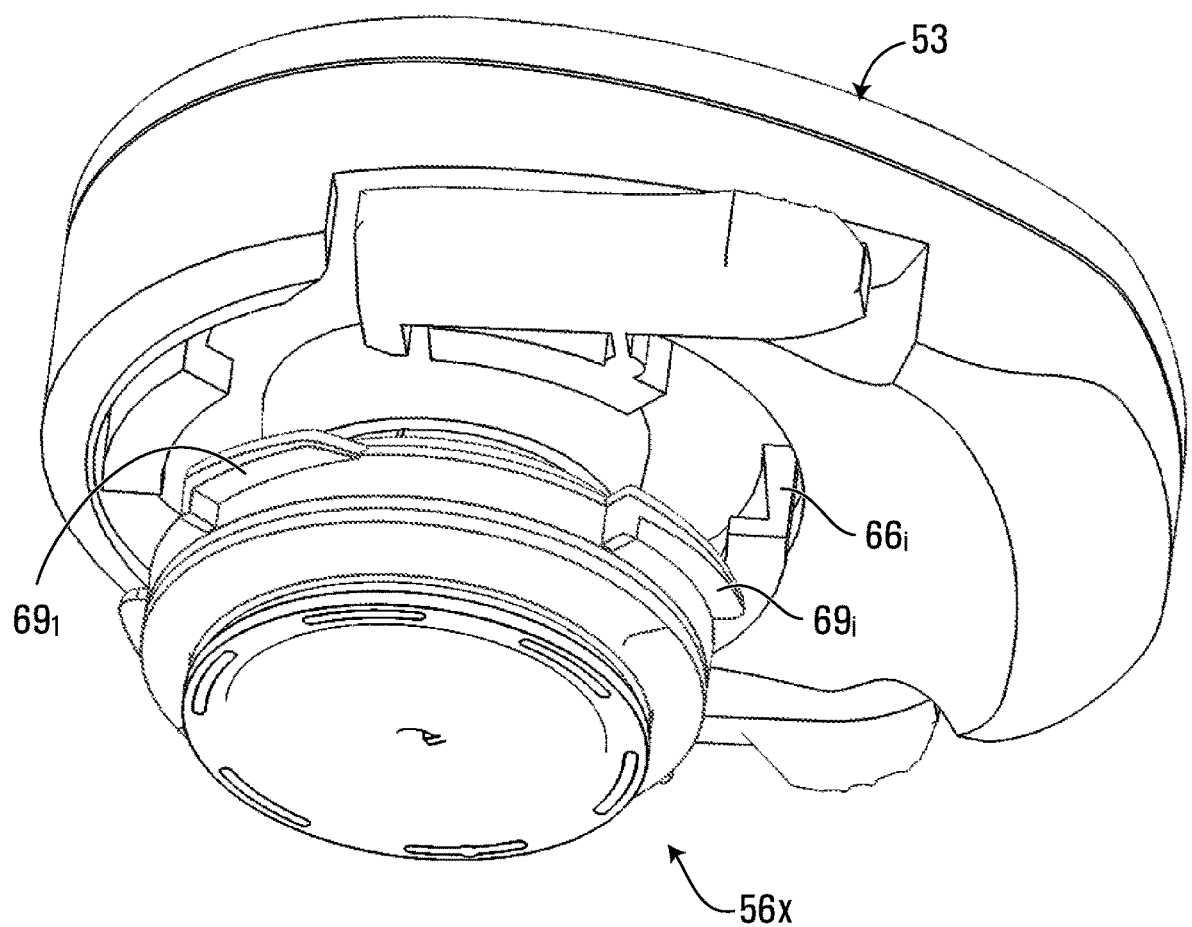
Figure 8E:
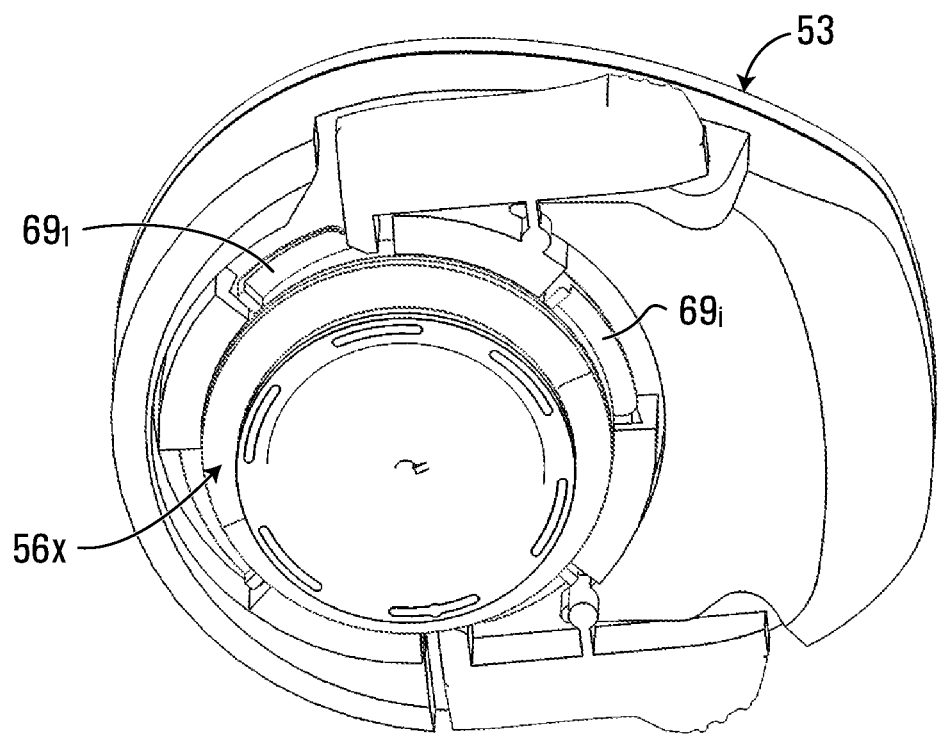
Figure 8F:
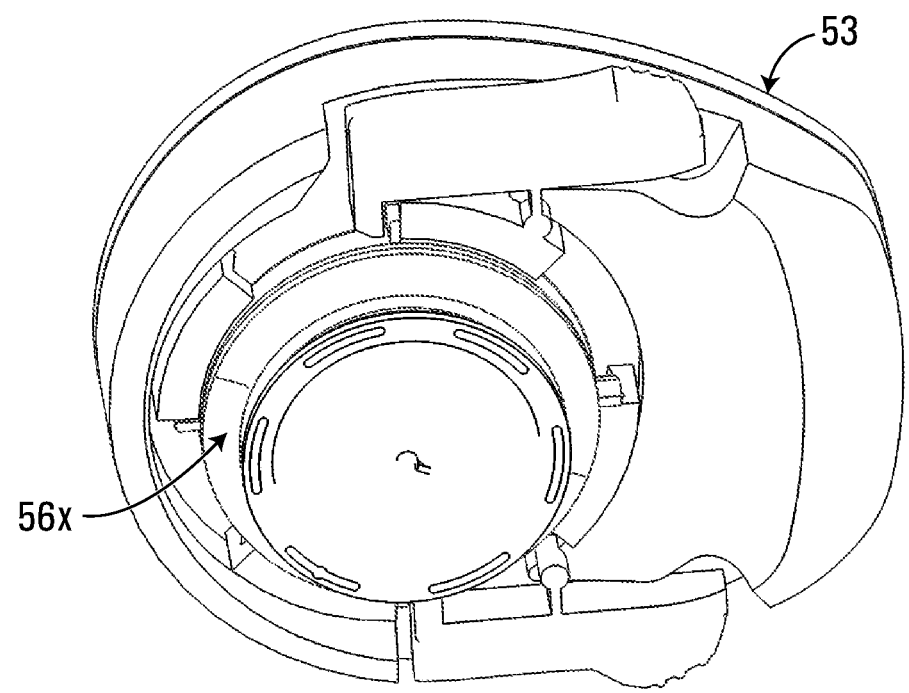
Figure 8G:
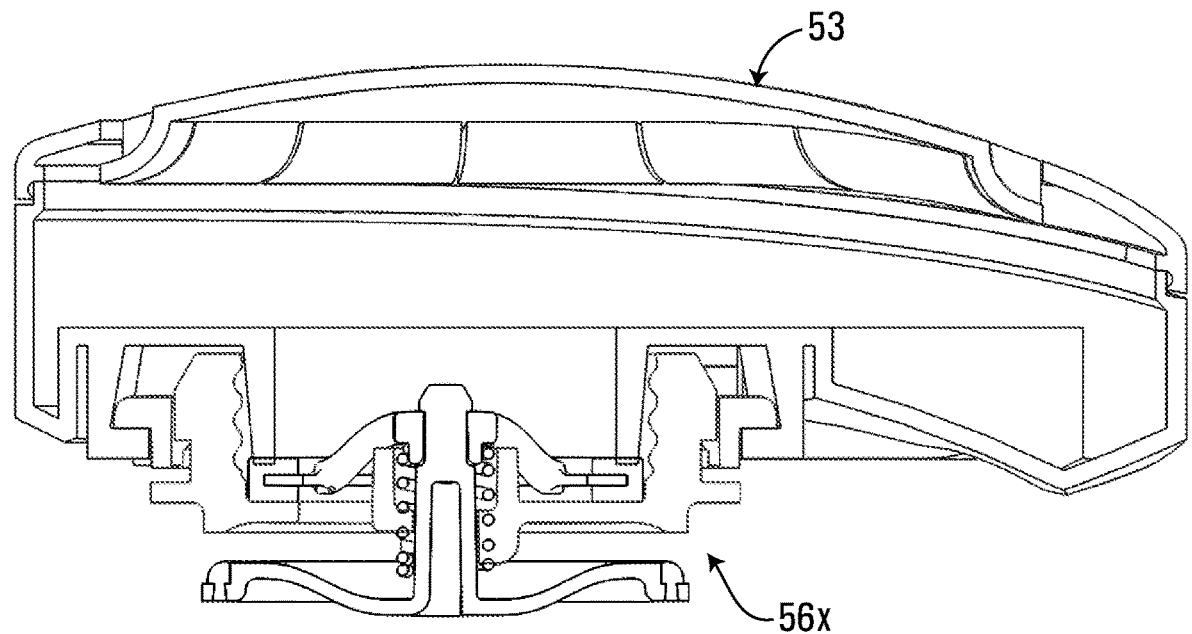
Figure 8H:
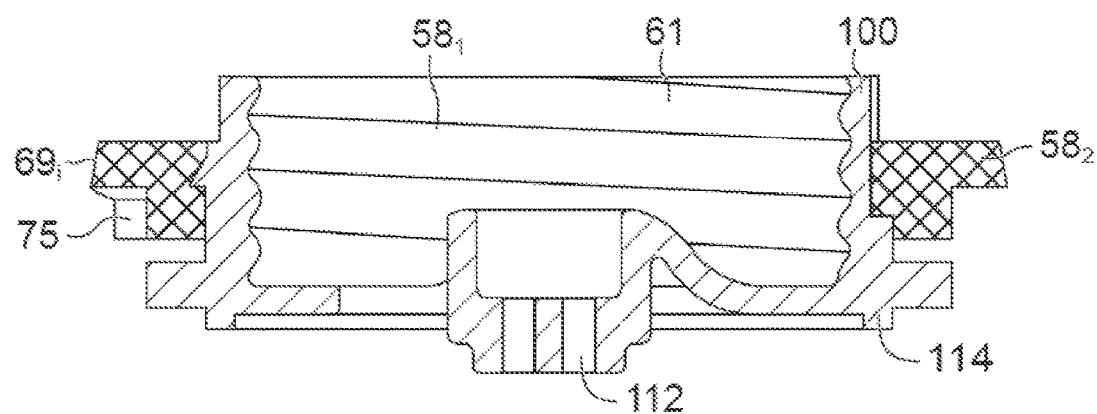
Figure 8I:
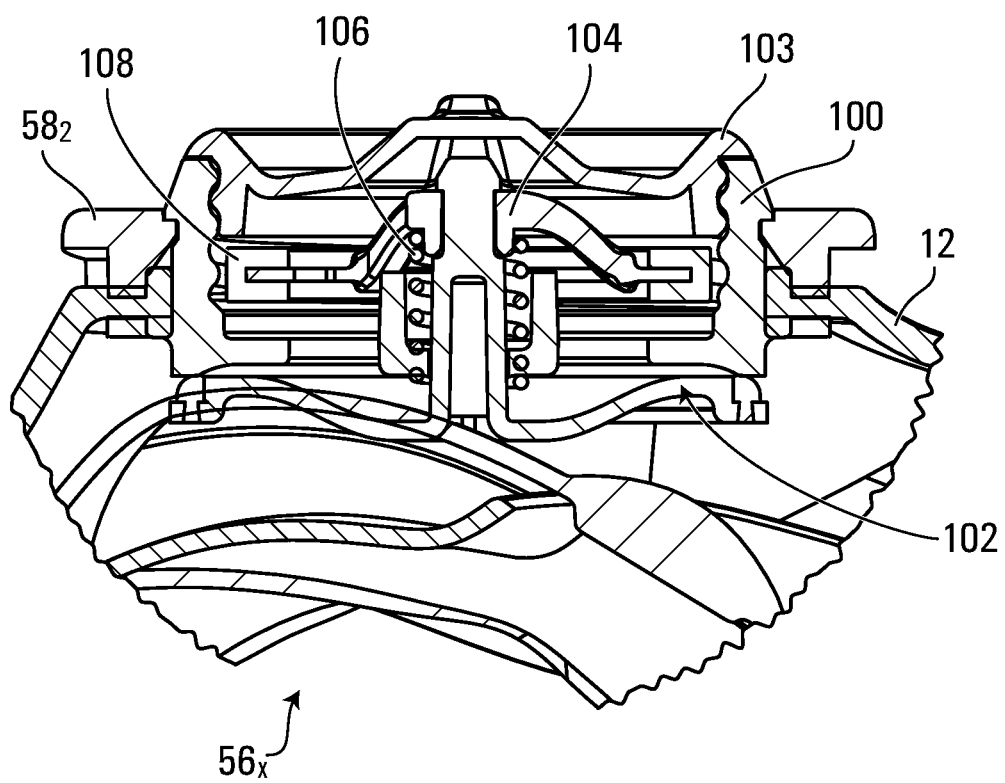
Figure 8K:
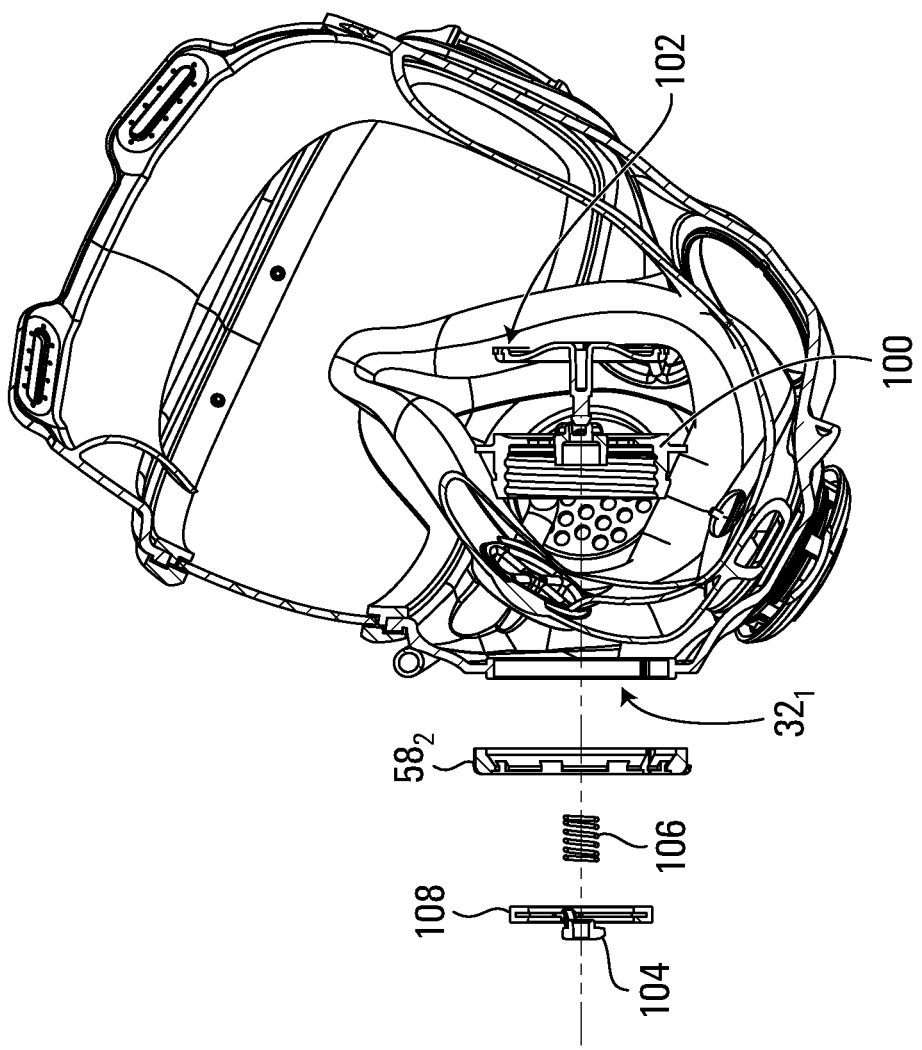
Figure 8J:
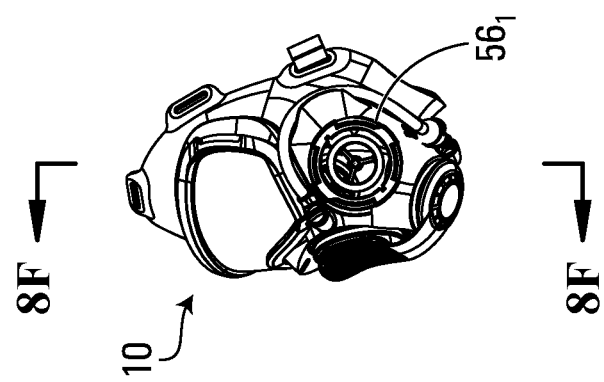
Figure 9:
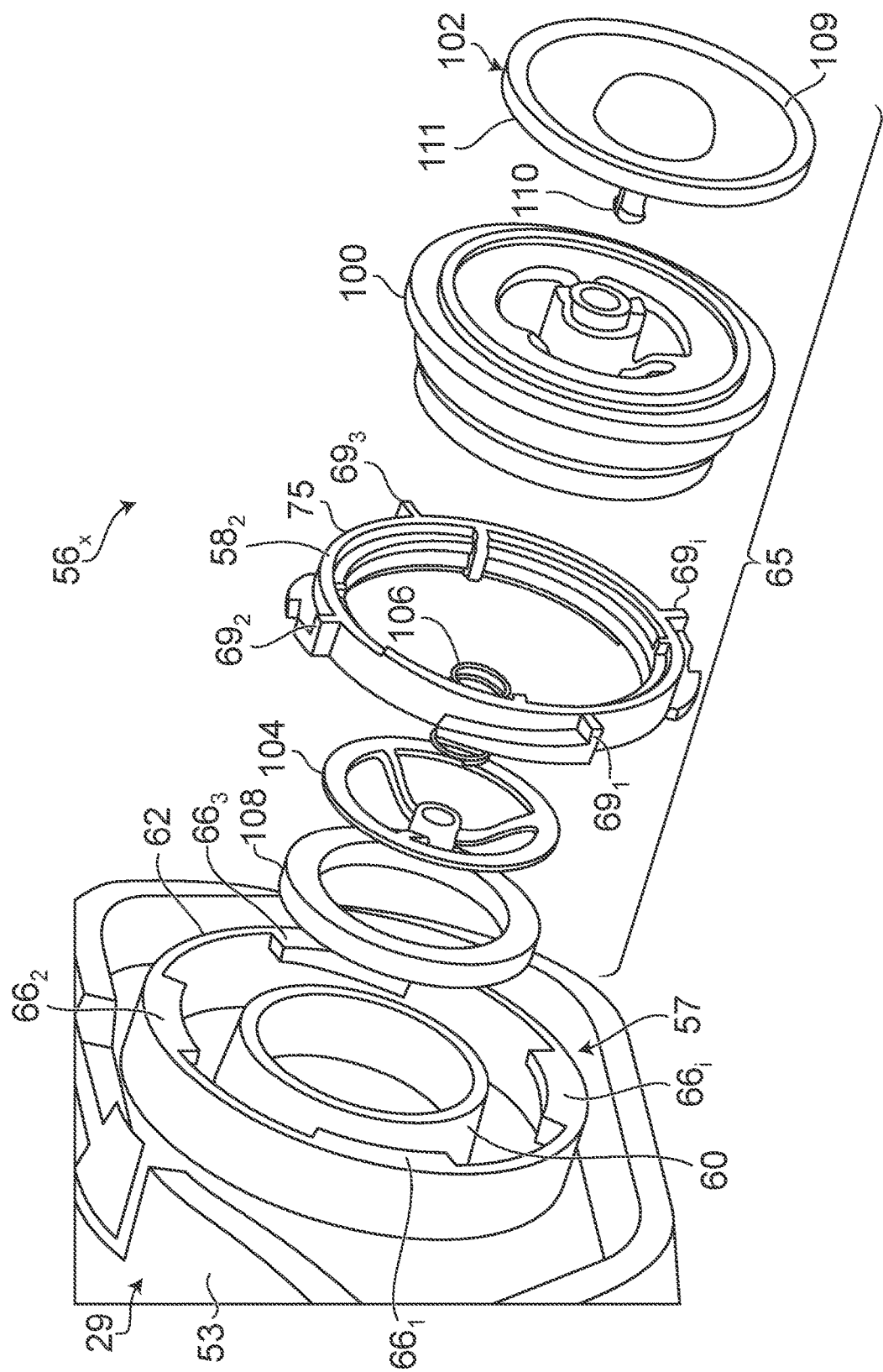

More specifically, in this embodiment, the mounting structure 57 of the filter 53 comprises an inner valve-engaging rim 60 for engaging the valve 65 of the filter mount $56_x$ and an outer securing rim 62 for engaging the connector $58_2$ of the filter mount $56_x$. The securing rim 62 is circular and has a diameter greater than a diameter of the connector $58_2$. In addition, the securing rim 62 comprises interlocking elements $66_1$-$66_i$ for meshing with the connector $58_2$ of the filter mount $56_x$. Accordingly, as shown in FIGS. 8D to 9, the connector $58_2$ of the filter mount $56_x$ comprises corresponding interlocking elements $69_1$-$69_i$ which are spaced apart from one another and are meshable with the interlocking elements $66_1$-$66_i$ of the securing rim 62. Each of the interlocking elements $69_1$-$69_i$ of the connector $58_2$ comprises an abutment 75 for abutting the interlocking elements $66_1$-$66_i$ of the securing rim 62.

Thus, in use, the wearer of the mask 10 (or another individual) wishing to mount the filter 53 to the filter mount $56_x$ first aligns the interlocking elements $66_1$-$66_i$ of the securing rim 62 with the connector $58_2$ such that the interlocking elements $69_1$-$69_i$ of the connector $58_2$ do not interfere with an inward movement of the securing rim 62. The filter 53 is then pushed inwardly towards the mask 10. Upon actuating the valve 65 by engagement of its valve-engaging rim 60 with the valve 65, the filter 53 is then turned (e.g., in a clockwise direction) such that the interlocking elements $66_1$-$66_i$ of the securing rim 62 slideably mesh with the interlocking elements $69_1$-$69_i$ of the connector $58_2$. This turn of the filter 53 is less than a complete rotation (i.e., less than 360°), which makes for a quick connection, in contrast to a screwing action requiring multiple full rotations. For instance, in some embodiments, a turn of less than 180°, in some cases less than 120°, in some cases less than 90° may be used to secure the filter 53 to the filter mount $56_x$ (e.g., a one-eighth turn, a quarter turn, or a half-turn). The abutment 75 of each of the interlocking elements $69_1$-$69_i$ then stops the sliding motion of the interlocking elements $66_1$-$66_i$. At this point, the filter 53 is safely secured to the filter mount $56_x$ and able to provide filtered air into the mask 10 for the wearer to breathe.

Referring to FIGS. 8A to 9, the valve 65 regulates airflow within the mask 10, including air flowing into the mask 10 for breathing by the wearer. More particularly, in this embodiment, the valve 65 is mounted within a frame 100 of the filter mount $56_x$. The frame 100 defines a passage for air to flow into the mask 10. In addition, the frame 100 includes the connector $58_1$ in its interior peripheral wall and securely receives the connector $58_2$ on its outer peripheral wall. Also, the frame 100 defines an opening 112 in a central position of the frame 100, and a sealing surface 114 at its bottom.

In this embodiment, the valve 65 comprises a movable closure 102, a support 104, a biasing member 106, and a seal 108. In this example, the movable closure 102 comprises: a base 109 operable to block the passage of air through the frame 100; a projection (e.g., a stem) 110 protruding from the base 109; and a sealing element 111 fixed on an upper surface of the base 109. In this case, the base 109 is disc-shaped. In other cases, the base 109 may have any other shape. The projection 110 is inserted into the opening 112 of the frame 100. The biasing member 106 is positioned around the projection 110, in a pocket of the frame 100. The support 104 is fixedly mounted onto an upper portion of the projection 110 and has a bottom surface abutting the biasing member 106 such that the biasing member 106 is compressed between the support 104 and the frame 100. Because the biasing member 106 is in compression, the support 104 and consequently the movable closure 102 are urged upwardly such that the sealing element 111 of the movable closure 102 is pressed against the sealing surface 114 of the frame 100. Furthermore, the seal 108 fixedly envelops the support member 104 such as to cover a peripheral surface, the top surface and the bottom surface of the support member 104.

In this example of implementation, the biasing member 106 is a spring, i.e., a resilient object that is deformable (i.e., changeable in configuration) such that it changes in configuration under load and recovers its initial configuration when the load is removed. More particularly, in this embodiment, the biasing member 106 is a coil spring (e.g., a metallic or polymeric coil spring). The biasing member 106 may be any other suitable type of spring in other embodiments. For example, in some embodiments, the biasing member 106 may be a leaf spring, an elastomeric spring (e.g., a rubber spring), a fluid spring (i.e., a spring including a liquid or gas contained in a container such as a cylinder or a bellows and variably compressed) such as a gas spring. Thus, deformation (i.e., change in configuration) of the biasing member 106 may be achieved in various ways in other embodiments.

In this embodiment, the valve 65 remains open while any one of the filters 52, 53 is connected to the filter mount $56_x$. That is, the valve 65 remains in its open state while the filter 52 is connected to the filter mount $56_x$ and, similarly, remains in its open state while the filter 53 is connected to the filter mount $56_x$ This lowers respiratory resistance compared to conventional masks in which valves repeatedly open and close as wearers inhale and exhale.

Also, in this embodiment, the valve 65 automatically closes when any one of the filters 52, 53 is disconnected from the filter mount $56_x$. That is, the valve 65 automatically acquires its closed state in response to the filter 52 being disconnected from the filter mount $56_x$ and, similarly, the valve 65 automatically acquires its closed state in response to the filter 53 being disconnected from the filter mount $56_x$. The valve 65 is thus a normally-closed valve such that its "normal" state is the closed state. This helps to seal the mask 10 against ingress of noxious agents through the filter mount $56_x$.

Interactions between the filters 52, 53 and the filter mount $56_x$ which allow the valve 65 to acquire one of its open and closed states in this embodiment will now be further described.

In this embodiment, the filter 52 comprises a valve-engaging rim 115 for engaging the valve 65 as well as the connector $58_1$ of the filter mount $56_x$. More specifically, as shown in FIG. 8A, the thread 63 of the filter 52 is provided on an outer peripheral surface of the valve-engaging rim 115. The thread 63 of the valve-engaging rim 115 is configured for engaging the matching thread 61 of the connector $58_1$ such that the valve-engaging rim 115 may be screwed into the connector $58_1$. This screwing action eventually leads to the valve-engaging rim 115 contacting the seal 108, after which further screwing causes the valve-engaging rim 115 to drive the seal 108, the support 104 and the movable closure 102 of the valve 65 inwards while the biasing member 106 is compressed. Consequently, a gap 120 opens between the movable closure 102 and the sealing surface 114 of the frame 100, thus allowing entry of air into the mask 10. Once the valve-engaging rim 115 has driven the support 104 to its bottom position within the frame 100, as illustrated in FIG. 8A, the gap 120 is at its greatest size and the filter 52 is fully locked into the filter mount $56_x$. At this point, the valve 65 is in its open state and remains open until the wearer of the mask 10 disengages the filter 52 from the filter mount $56_x$.

Conversely, to disengage the filter 52 from the filter mount $56_x$, the valve-engaging rim 115 is unscrewed from the connector $58_2$. As the valve-engaging rim 115 is unscrewed, the force exerted by the biasing member 106 on the bottom surface of the support 104 causes the support 104 and the movable closure 102 to be displaced upwardly. This in turn causes the gap 120 to reduce in size. Once the valve-engaging rim 115 has been sufficiently unscrewed from the connector $58_2$, the sealing element 111 of the movable closure 102 presses against the sealing surface 114 of the frame 100 such that the gap 120 is closed off (i.e., becomes substantially non-existent). The filter 52 is thus dismounted from the filter mount $56_x$ and the valve 65 is in its closed state.

A similar procedure occurs in this embodiment when mounting and dismounting the filter 53 from the filter mount $56_x$. In this case, however, the filter 53 is not provided with threads instead comprising the mounting structure 57 to engage the connector $58_2$ of the filter mount $56_x$.

In this embodiment, as shown in FIG. 8B, in order to mount the filter 53 to the filter mount $56_x$, the filter 53 is pushed into the filter mount $56_x$. If the interlocking elements $66_1$-$66_i$ of the securing rim 62 press against the interlocking elements $69_1$-$69_i$ of the connector $58_2$ and thus prevent pushing the filter 53 inwardly, a simple rotation of the filter 53 allows to correctly engage the connector $58_2$. If properly aligned, pushing the filter 53 into the filter mount $56_x$ causes the inner valve-engaging rim 60 of the filter 53 to inwardly push the seal 108 of the valve 65. In turn, this causes the support 104 and the movable closure 102 to be driven inwardly. Consequently, the gap 120 is opened between the movable closure 102 and the sealing surface 114 of the frame 100. Once the inner valve-engaging rim 60 has driven the support 104 to its bottom position within the frame 100, as illustrated in FIG. 8B, the gap 120 is at its greatest size. At this point, the filter 53 is turned (e.g., in a clockwise direction) in order for the interlocking elements $66_1$-$66_i$ to slideably mesh with the interlocking elements $69_1$-$69_i$ of the connector $58_2$. The abutments 75 of the interlocking elements $69_1$-$69_i$ stop the wearer from further rotating the filter 53. At this point, the filter 53 is secured to the filter mount $56_x$ and the valve 65 is in its open state. The valve 65 remains in its open state until the filter 53 is disengaged from the filter mount $56_x$.

In order to dismount the filter 53 from the filter mount $56_x$, the filter 53 is turned in an opposite direction (e.g., a counterclockwise direction) to cause the interlocking elements $66_1$-$66_i$ to disengage from the interlocking elements $69_1$-$69_i$. The filter 53 is then pulled outwardly from the filter mount $56_x$. As the filter 53 is pulled away, the force exerted by the biasing member 106 on the bottom surface of the support 104 causes the support 104 and the movable closure 102 to be displaced upwardly. This in turn causes the gap 120 to reduce in size. Once the inner rim 60 of the filter 53 is no longer in contact with the valve 65, the sealing element 111 of the movable closure 102 presses against the sealing surface 114 of the frame 100 such that the gap 120 is closed off. The filter 53 is thus dismounted from the filter mount $56_x$ and the valve 65 is in its closed state.

The filter mount $56_x$ may be implemented (e.g., shaped, constructed, etc.) in various other ways in other embodiments. For example, in some embodiments, as shown in FIG. 81, the filter mount $56_x$ may comprise a cap 103 for closing the filter mount $56_x$. In this embodiment, the cap 103 is threaded such that it interacts with the connector $58_1$ of the filter mount $56_x$ (i.e., the cap 103 is screwed into the filter mount $56_x$) but does not actuate the valve 65 of the filter mount $56_x$. In other embodiments, the cap 103 may instead comprise a structure similar to securing rim 62 in order engage the connector $58_2$ of the filter mount $56_w$.

The filters 52, 53 may be implemented in any suitable way. For example, the filters 52, 53 may provide protection against chemical substances (e.g., chemical weapon agents (CWA) and toxic industrial chemicals (TICs)) or other noxious agents. In some embodiments, a given one of the filters 52, 53 may comprise a filtering material including active particles. The active particles are "active" in that they have a property allowing them to induce a chemical and/or physical reaction in response to a stimulus at their surface. For example, the active particles may have an adsorptive property that causes them to adsorb contaminants or other noxious agents. For instance, the active particles may be microporous particles each including a multitude of pores (e.g., several thousands of pores) which can trap the contaminants or other noxious agents. The active particles may be implemented in any suitable way. For example, in some embodiments, the active particles may comprise activated carbon, alumina (aluminum oxide), silica gel, soda ash, aluminum trihydrate, baking soda, cinoxate (p-methoxy-2-ethoxyethyl ester cinnamic acid), zinc oxide, zeolites, titanium dioxide, or any other suitable material. The filtering material may be contained in a container (e.g., a canister). Such filters 52, 53 are well known and will thus not be described further herein. Also, the filtering material may be any other suitable material in other embodiments (e.g., the filtering material may not necessarily include active particles).

Figure 11:
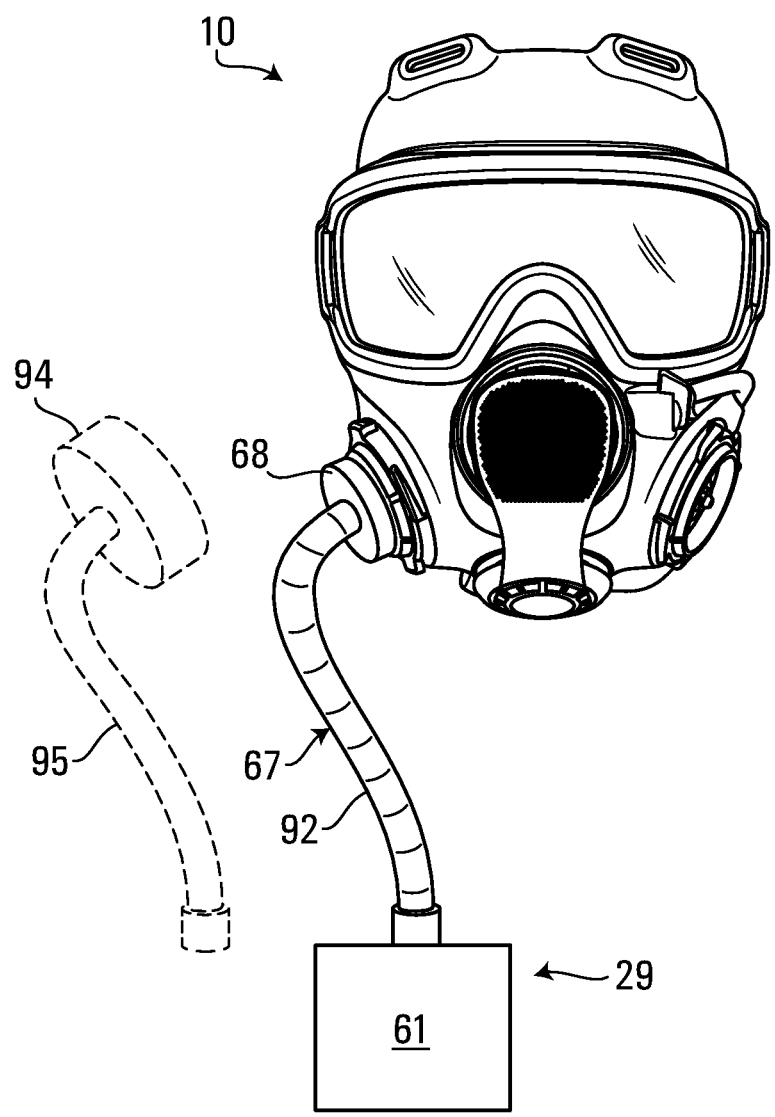

As shown in FIG. 11, in some embodiments, the air-providing device 29 may be, instead of the filter 52 or the filter 53, a conduit 67 of a remote air supply 61 that is supported remotely from the mask 10 (e.g., on a belt or on a back of the wearer) and supplies clean air which is deliverable to the mask 10 via the conduit 67. The remote air supply 61 may comprise a powered filtering apparatus (e.g., in which case the mask 10 and the remote air supply 61 may constitute a powered air-purifying respirator) or an air tank (e.g., in which case the mask 10 and the remote air supply 61 may constitute a self-contained breathing apparatus). Since pressure is used to deliver the air from the remote air supply 61 to the mask 10 via the conduit 67, the mask 10 can be viewed as operating in a "positive-pressure" mode, i.e., air pressure inside the mask 10 is greater than ambient air pressure during inhalation and exhalation of the wearer. In contrast, when it relies only on the filter 52 or the filter 53 to provide clean air, the mask 10 can be viewed as operating in a "negative-pressure" mode, i.e., air pressure inside the mask 10 becomes lower than ambient air pressure when the wearer inhales.

In this embodiment, the conduit 67 of the remote air supply device 61 comprises a tube 92 for conveying clean air and a connector 68 for connecting the conduit 67 to the mask 10. The connector 68 of the conduit 67 is connectable to either one of the mounts $56_1$, $56_2$.

More particularly, in this embodiment, each mount $56_x$ is connectable to a plurality of different types of conduits of remote air supplies, including the conduit 67 of the remote air supply 61 and another conduit 95 of different type than the conduit 67, similarly to that discussed above in respect of the different types of filters. When any one of the conduits 67, 95 is connected to a corresponding one of the connectors $58_1$, $58_2$ of the mount $56_x$, it interacts with the mount $56_x$ so as to operate the valve 65, as discussed above in respect of the different types of filters.

In this example of implementation, the connector 68 of the conduit 67 is a threaded connector (e.g., with a 40-mm NATO thread) which is securable to the mount $56_x$ by being screwed into the threaded connector $58_1$ of the mount $56_x$. The connector 94 of the conduit 95 is a threadless connector which is securable to the threadless connector $58_2$ of the mount $56_x$ without being screwed into the filter mount $56_x$ but rather by being pushed into the filter $56_x$ and turned by less than a complete rotation, as discussed above in respect of the filter 53. The connector 94 of the conduit 97 is thus similar to the mounting structure 57 of the filter 53.

In this embodiment, with additional reference to FIGS. 37A to 38B, the breathing interface 16 comprises an outlet assembly 175 providing an outlet for air exhaled by the wearer of the mask 10. In this example, the outlet assembly 175 comprises a selector 180, a connector 181, a positioning device 183, a movable closure 184, a biasing member 186, a valve member 188, and an outlet mount 190.

The selector 180 is operable to selectively change the mask 10 between the negative-pressure mode and the positive-pressure mode. In this example of implementation, the outlet assembly 175 has an activated mode and a deactivated mode which are selectable by the wearer through interaction with the selector 180.

Figure 39:
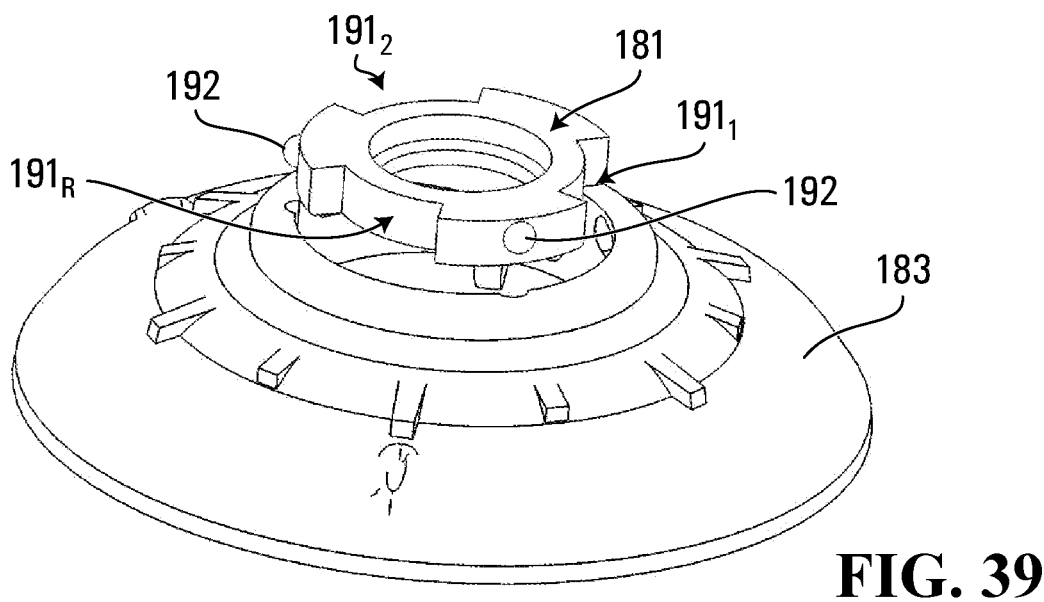
FIGS. 39 to 46 show multiple components of the outlet assembly.
Figure 40:
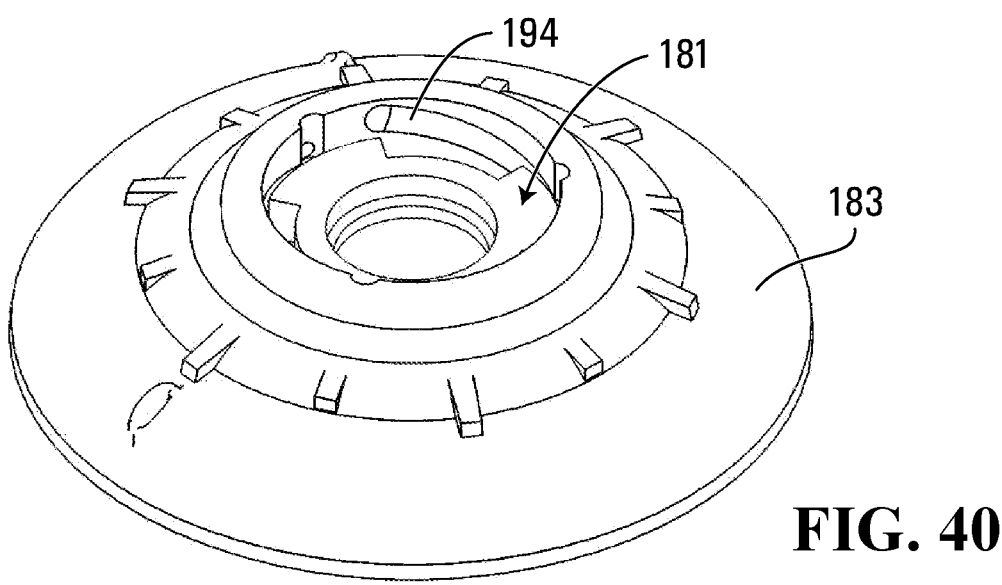
Figure 41:
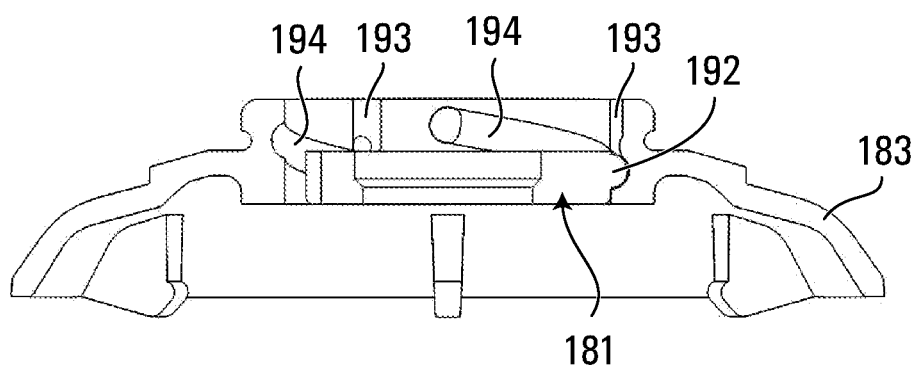
Figure 42:
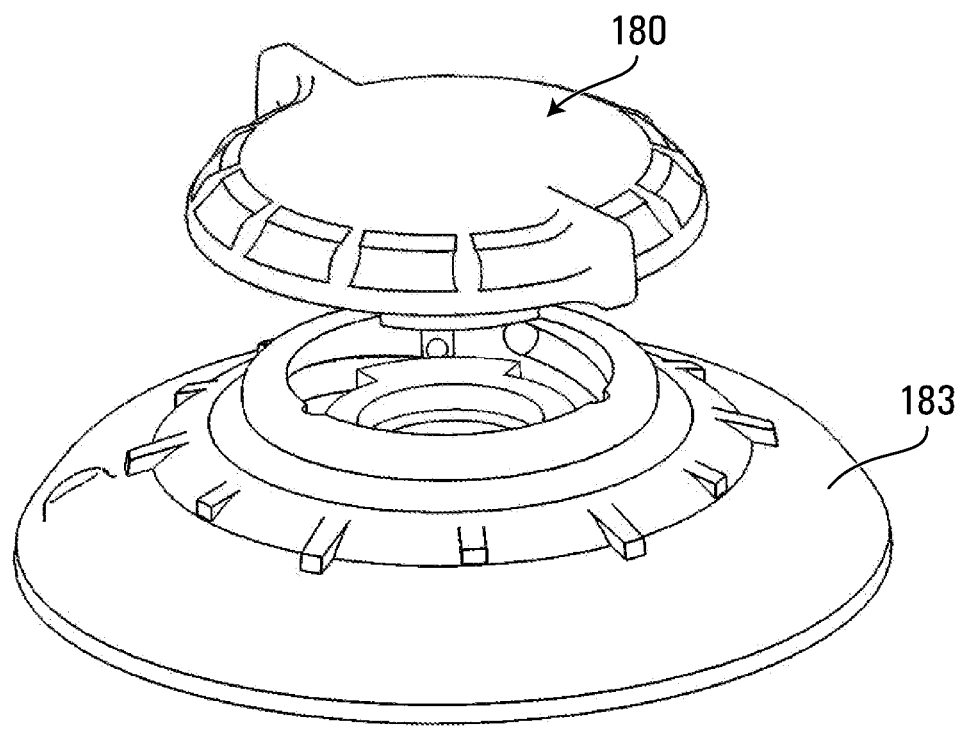
Figure 43:
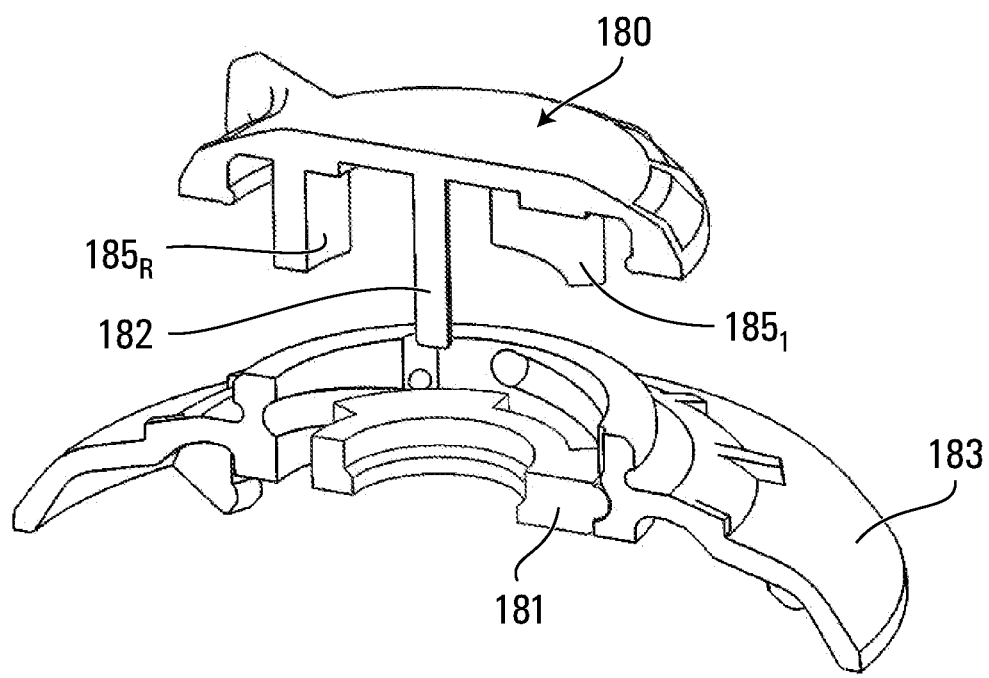
Figure 44:
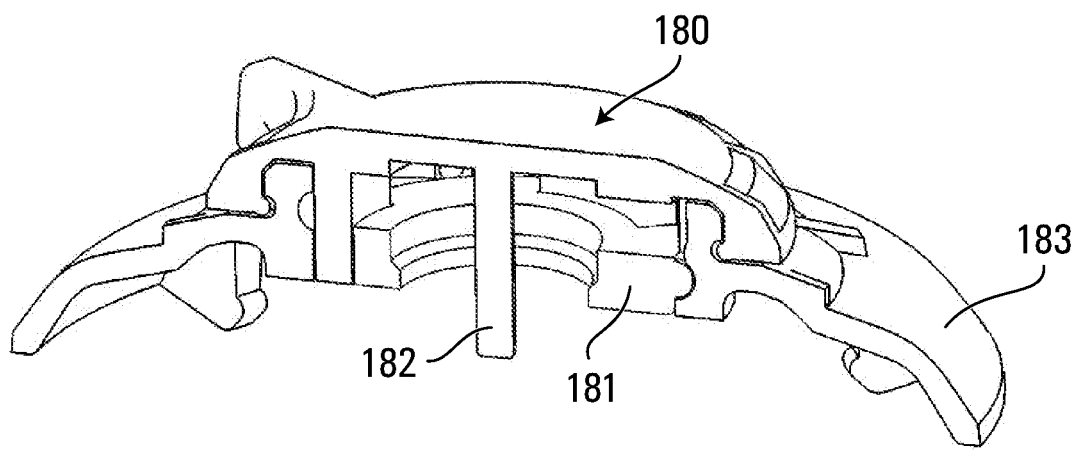
Figure 45:
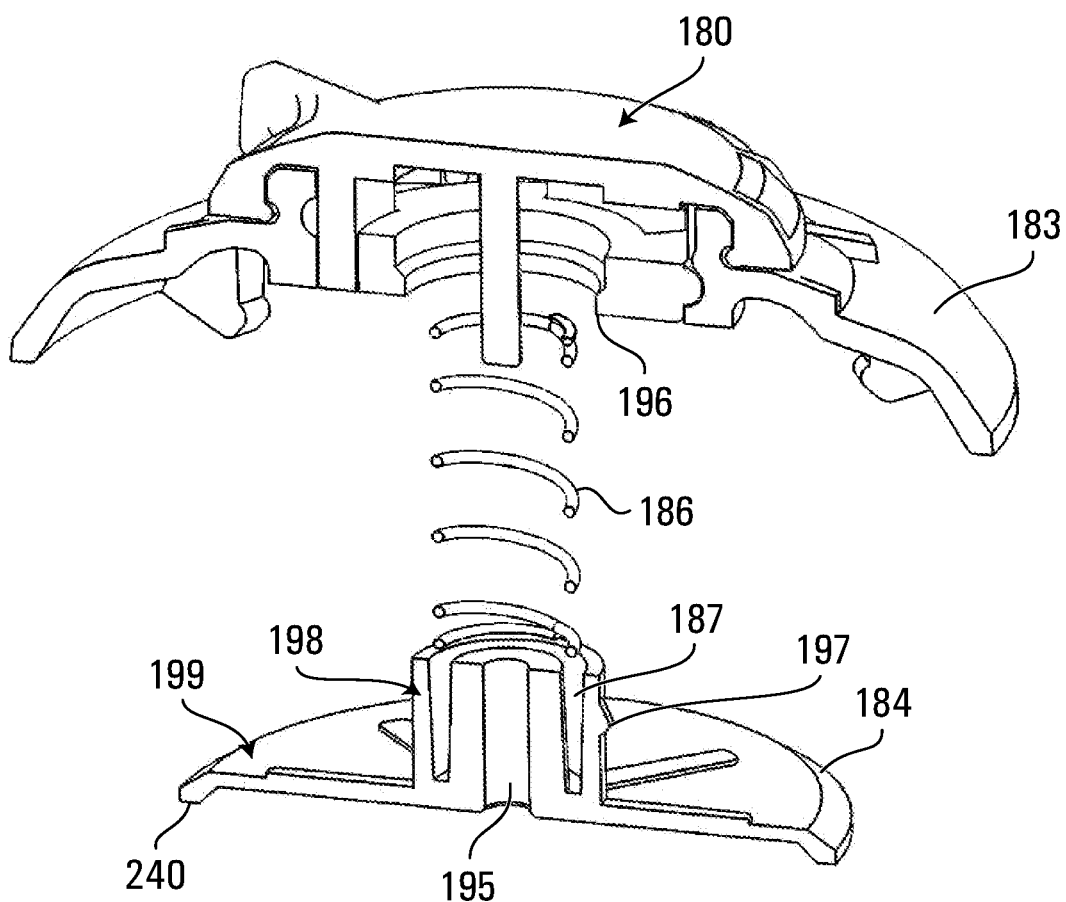
Figure 46:
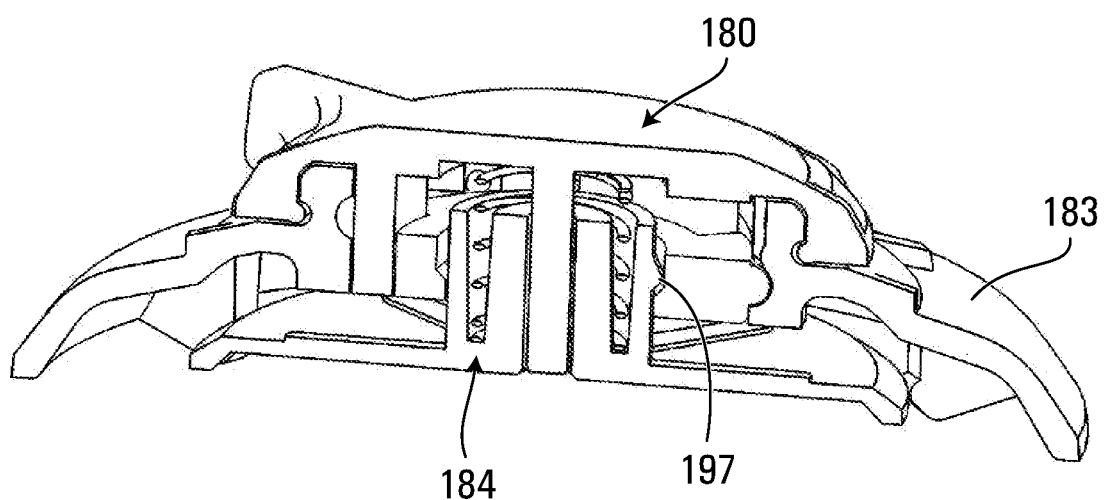

To that end, in this embodiment, with reference to FIGS. 39 to 46, the selector 180 comprises a projection 182 (e.g., a stem) for engaging the movable closure 184 and legs $185_1$-$185_R$ for engaging the connector 181. The connector 181 has a generally cylindrical shape with recesses $191_1$-$191_R$ along its outer periphery. The connector 181 comprises protrusions 192 along its outer peripheral surface for engaging the positioning device 183 and a lip 196 on its inner peripheral surface for engaging the movable closure 184. The positioning device 183 comprises apertures 193 which are interconnected to races 194 disposed on an inner peripheral surface of the positioning device 183. The races 194 spiral along a vertical length of the inner peripheral surface of the positioning device 183. As shown in FIGS. 39 to 41, the protrusions 192 of the connector 181 are inserted into the apertures 193 of the positioning device 183 from an outer side. The selector 180 is then inserted such that its legs $185_1$-$185_R$ mesh with the recesses $185_1$-$185_L$ of the connector 181.

Furthermore, in this embodiment, the movable closure 184 comprises a connecting portion 198 and a valve-engaging portion 199. The connecting portion 198 of the movable closure 184 comprises a pocket 187 in which the biasing member 186 is positioned and an opening 195 in which the projection 182 of the selector 180 is inserted. Thus, when assembled, the biasing member 186 is compressed between the selector 180 and the movable closure 184. Moreover, the connecting portion 198 comprises a lip 197 for engaging the lip 196 of the connector 181. The valve-engaging portion 199 of the movable closure 184 is operable to selectively engage and disengage the valve member 188. The outlet mount 190 comprises an opening 244 and an exhaust port 242 for allowing the passage of exhaled air out of the mask 10. In this embodiment, the outlet mount 190 is mounted onto the facepiece 12 of the mask 10 by being overmolded thereto. The outlet mount 190 may be mounted to the facepiece 12 in any other suitable way in other embodiments. The valve member 188 comprises a base portion 246 and a mounting portion 248. The base portion 246 is flexible thus allowing it to bend relative to the mounting portion 248. The mounting portion 248 comprises a projection configured for mounting onto the outlet mount 190. In its resting position, the base portion 246 sits generally perpendicularly relative to the mounting portion 248.

In this example of implementation, the biasing member 186 is a spring, i.e., a resilient object that is deformable (i.e., changeable in configuration) such that it changes in configuration under load and recovers its initial configuration when the load is removed. More particularly, in this embodiment, the biasing member 186 is a coil spring (e.g., a metallic or polymeric coil spring). The biasing member 186 may be any other suitable type of spring in other embodiments. For example, in some embodiments, the biasing member 186 may be a leaf spring, an elastomeric spring (e.g., a rubber spring), a fluid spring (i.e., a spring including a liquid or gas contained in a container such as a cylinder or a bellows and variably compressed) such as a gas spring. Thus, deformation (i.e., change in configuration) of the biasing member 186 may be achieved in various ways in other embodiments.

Figure 37A:
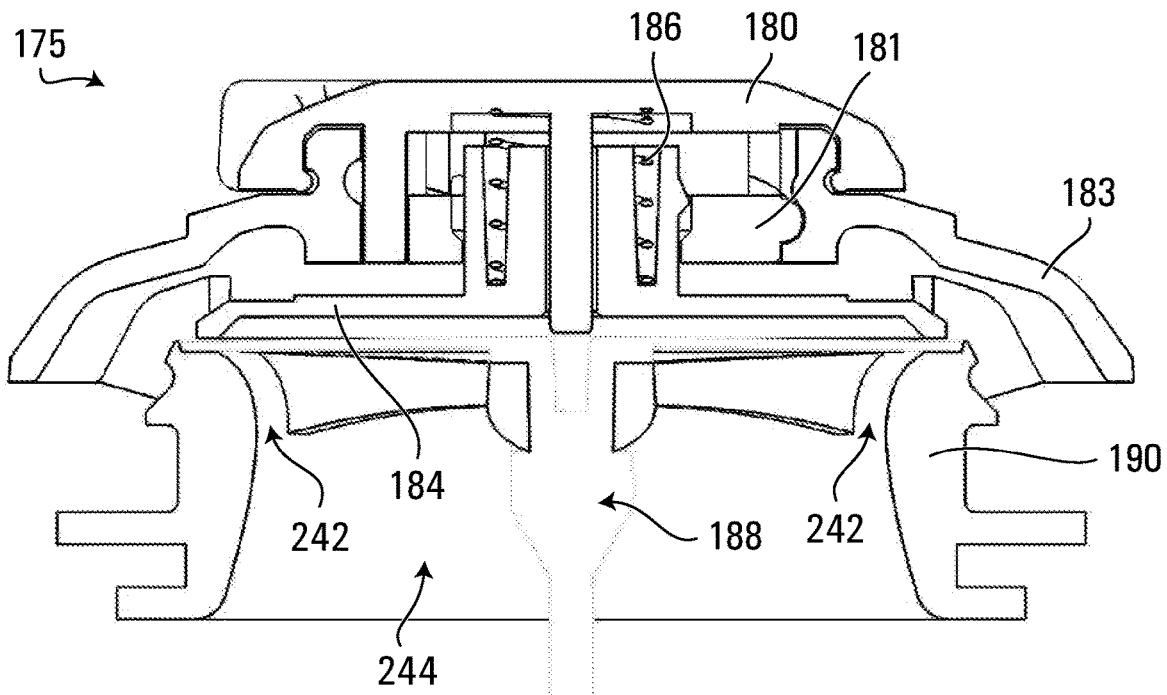
FIGS. 37A and 37B show an outlet assembly of the breathing interface in an activated mode.
Figure 37B:
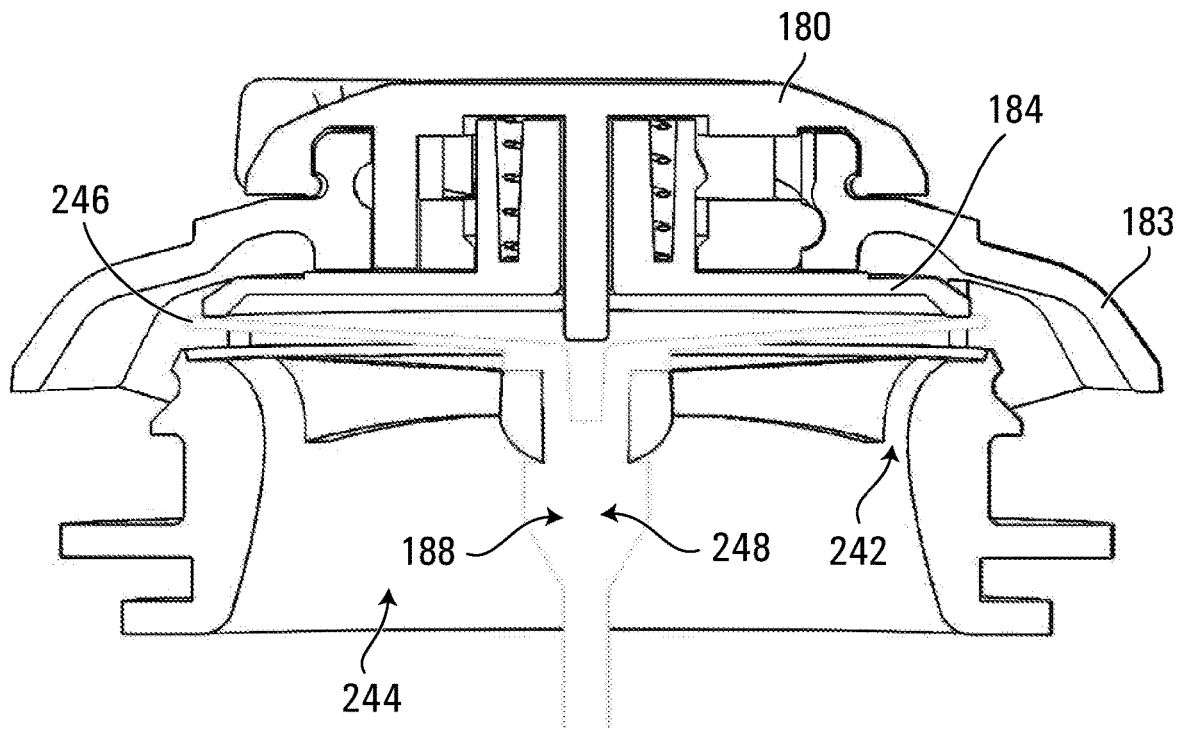
Figure 38A:
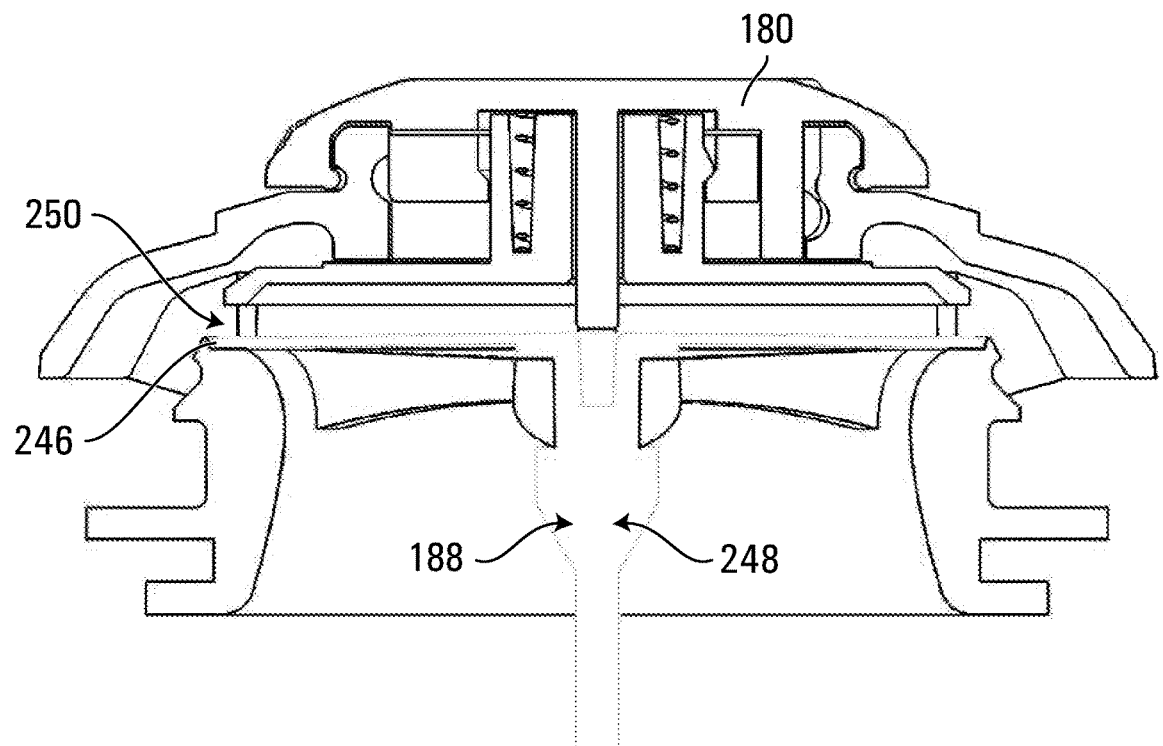
FIGS. 38A and 38B show the outlet assembly in a deactivated mode.

Assuming that the mask 10 is in the deactivated mode as illustrated in FIG. 38A, in this embodiment, the wearer (or another person) wishing to switch the outlet assembly 175 into the activated mode can turn the selector 180 (e.g., in a clockwise direction). Through the legs $185_1$-$185_R$, this turn of the selector 180 causes the connector 181 to rotate and thus the protrusions 192 to climb down the races 194 of the positioning device 183. In turn, this causes the biasing member 186 to extend itself and, since the selector 180 is vertically fixed, to push the movable closure 184 to a bottom position as shown in FIG. 37A. This causes a bottom surface 240 of the valve-engaging portion 199 of the movable closure 184 to contact the valve member 188. Thus, the biasing member 196 applies a downwards force on the valve member 188 such as to force it into contact with the outlet mount 190. Therefore, there is a resistance the valve member 188 has to overcome to allow the passage of air through the exhaust port 242. At this point, the outlet assembly 175 is in its activated mode and the mask 10 is thus in the positive-pressure mode. As the wearer of the mask 10 exhales, as shown in FIG. 37B, the pressure differential between the exhaled air and the air outside of the mask 10 causes the exhaled air to force a radial extent of the base portion 246 of the valve member 188 to bend and push against the movable closure 184. Consequently a passage is opened for the exhaled air to flow through to the outside of the mask 10. The valve member 88 then returns to its resting position and once against sits flat against the outlet mount 190.

Figure 38B:
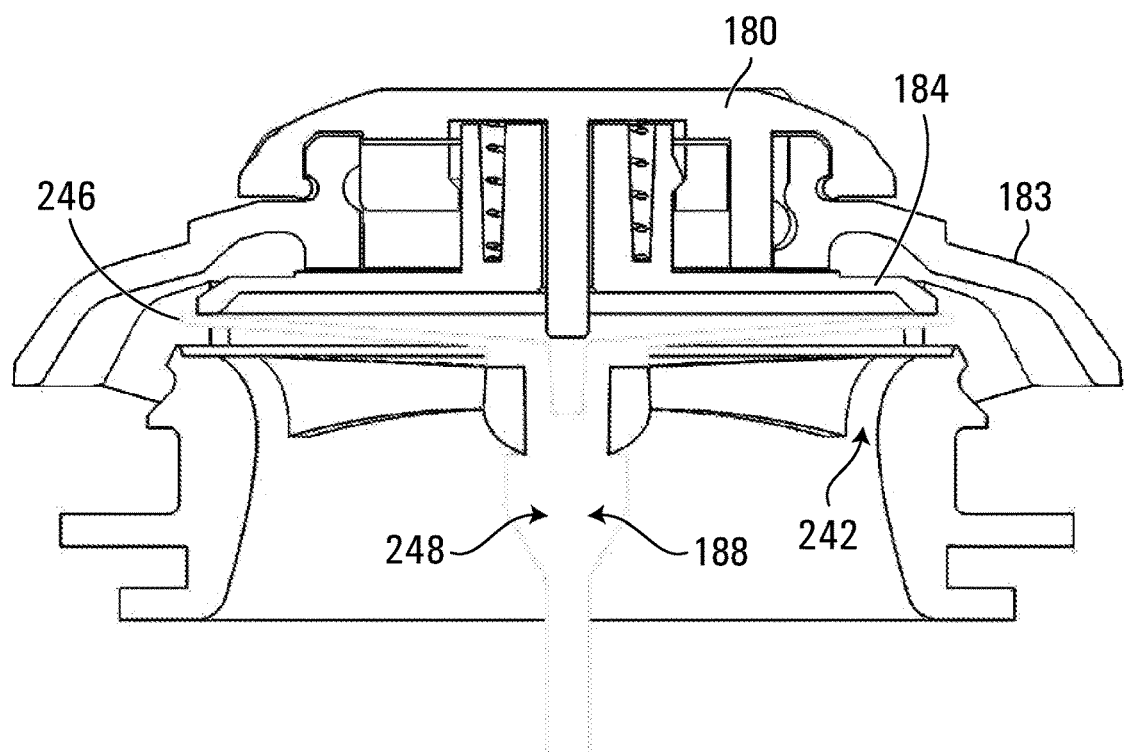

Conversely, the wearer of the mask 10 (or another person) wishing to switch the outlet assembly into the deactivated mode can turn the selector 180 in the opposite direction (e.g., a counter-clockwise direction). Again, through the legs $185_1$-$185_R$, this turn of the selector 180 causes the connector 181 to rotate and thus the protrusions 192 to climb up the races 194 of the positioning device 183. As the connector 181 moves outwards towards the selector 180, the lip 196 of the connector 181 engages the lip 197 of the movable closure 184 thus forcing the movable closure 184 outwards against the resistance applied by the biasing member 186. As a result of this displacement, a gap 250 opens up between the movable closure 184 and the base portion 246 of the valve member 188. At this point, the outlet assembly 175 is in its deactivated mode and the mask 10 is in the negative-pressure mode. The biasing member 186 does not apply any force on the base portion 246 of the valve member 188 and thus the wearer does not need to overcome its resistance when exhaling. As the wearer of the mask 10 exhales, as shown in FIG. 38B, the exhaled air forces a radial extent of the base portion 246 of the valve member 188 to bend until it touches the movable closure 184.

Consequently a passage is opened for the exhaled air to flow through the exhaust port 242 and to the outside of the mask 10. The valve member 88 then returns to its resting position and once again sits flat against the outlet mount 190.

The harness 18 is used to secure the mask 10 to the wearer's head. The harness 18 extends from the facepiece 12 towards a back of the wearer's head. In this embodiment, the harness 18 comprises a cap 70 to engage at least the back of the wearer's head and adjustment straps $72_1$, $72_2$ to adjust (i.e., tighten or loosen) a fit of the mask 10 on the wearer's head.

Figure 12A:
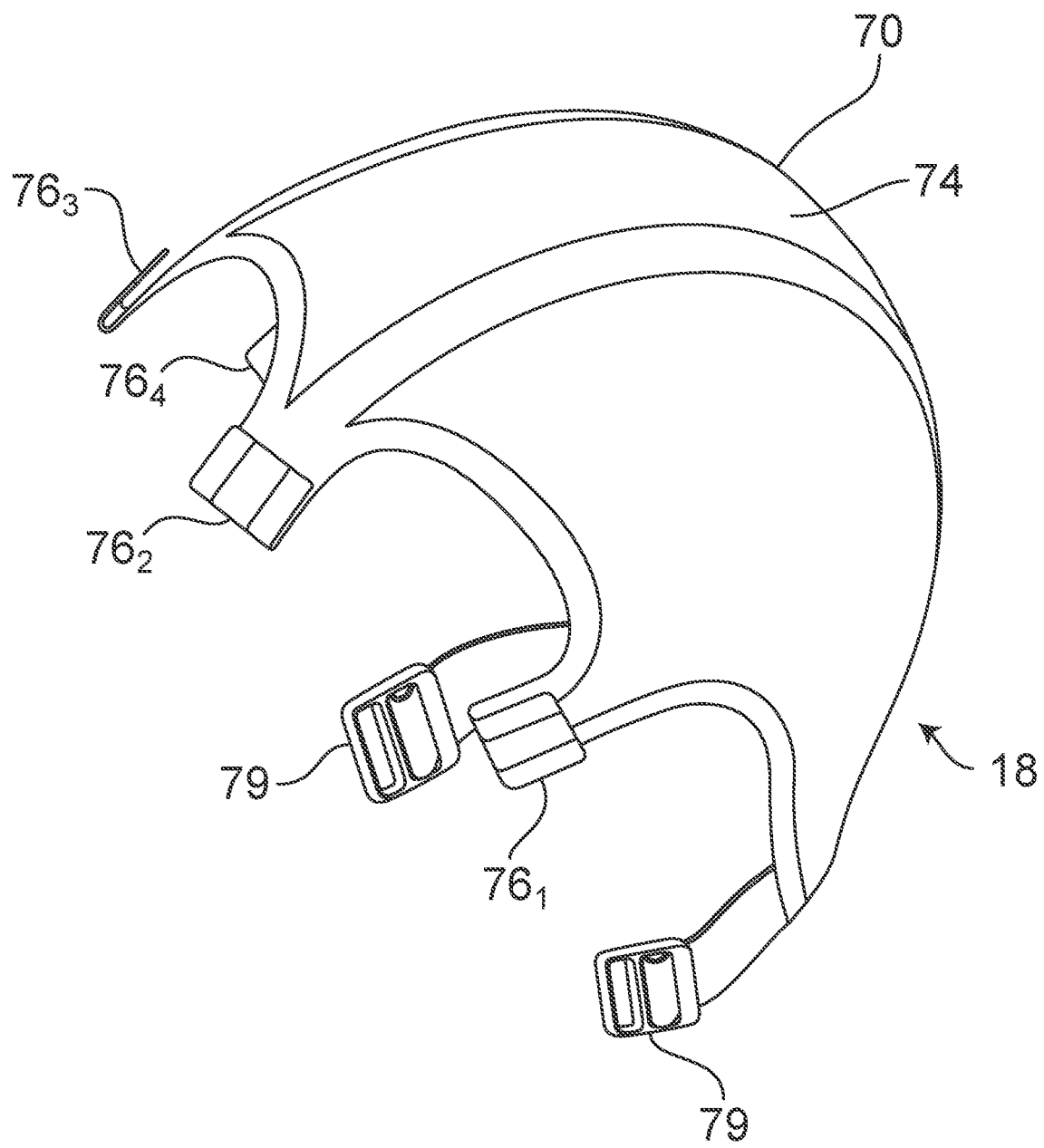
FIGS. 12A to 12C show a harness of the respirator mask.
Figure 12B:
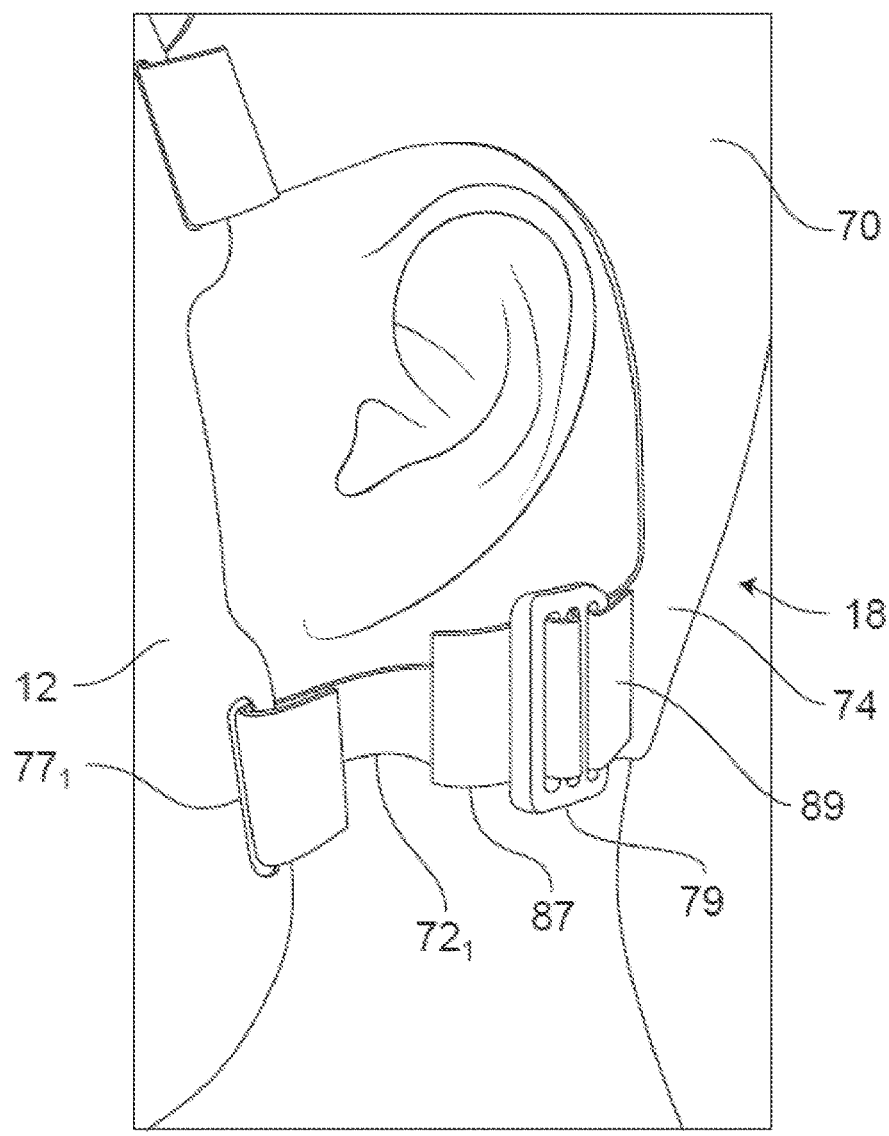

More particularly, in this embodiment, with additional reference to FIGS. 12A and 12B, the cap 70 engages a top and the back of the wearer's head. As such, the cap 70 extends from a front top portion of the wearer's head to a lower back portion of the wearer's head. This allows better distribution of a stress load on the wearer's head due to an increased surface contact with the wearer's head. Laterally, the cap 70 extends from a region below a right ear to a region below a left ear of the wearer. The cap 70 may comprise gaps, i.e. regions with no material, to accommodate the ears of the wearer. In this embodiment, the adjustment straps $72_1$, $72_2$ are positioned adjacent to lateral ends of the cap 70.

In this embodiment, the cap 70 comprises a fabric material 74. The fabric material 74, which may also be referred to as a textile material, is a thin pliable material comprising natural or synthetic fibers that may form elongated fabric/textile elements, such as filaments, strands or yarns, and that have been combined by weaving, knitting interlacing, felting, or otherwise crossing or entangling them. The fabric material 74 may include a woven fabric or a non-woven fabric. In this example, the fabric material 74 comprises a stretchable fabric (e.g., a PA-elastane blend). In other cases, the fabric material 74 may comprise any other suitable material (e.g., rubber or any other elastomeric material). In some embodiments, the harness 18 may be constructed as discussed in U.S. Pat. No. 5,038,776, which is hereby incorporated by reference herein.

In this embodiment, the adjustment straps $72_1$, $72_2$ are pullable frontwardly (i.e., towards a front of the wearer's head) to tighten the mask 10 when it is donned. This can make it easier to don the mask 10 (e.g., in contrast to conventional masks where adjustment straps are pulled rearwardly).

Figure 12C:
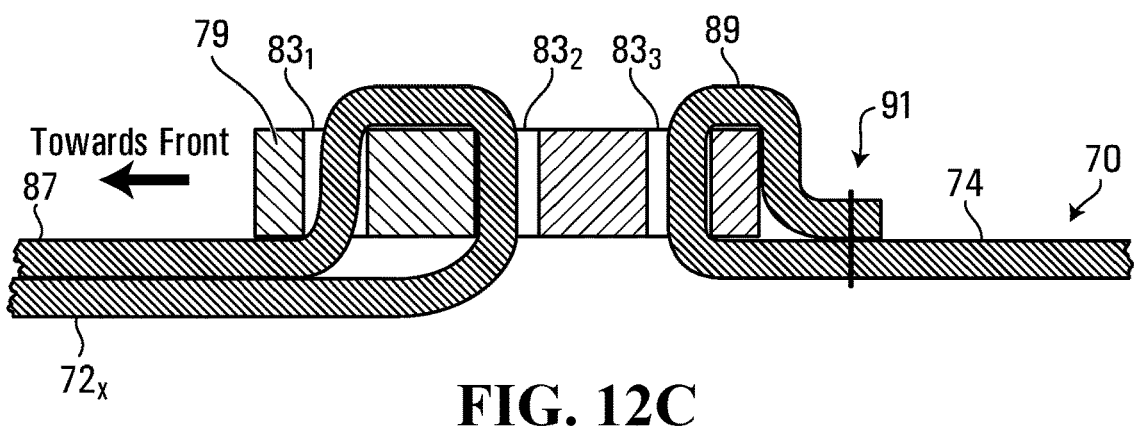

More particularly, in this embodiment, each adjustment strap $72_x$ interacts with a sliding buckle 79. The adjustment strap $72_x$ wraps about the sliding buckle 79 such that the adjustment strap $72_x$ is pullable frontwardly. More specifically, as shown in FIG. 12C, the sliding buckle 79 comprises a plurality of slots $83_1$-$83_3$ each of which is operable to receive therein a strap. At one end of the sliding buckle 79, an end of a strap 89 of the fabric material 74 is inserted into the slot $83_3$ and looped back around towards the back of the wearer's head. A joint 91 is formed between the end of the strap 89 and a portion of fabric material 74 that is not wrapped about the sliding buckle 79. In this embodiment, the joint 91 is a stitching. In other embodiments, the joint 91 may be implemented in any other suitable manner (e.g., an ultrasonic weld or adhesive bond). In some cases, the slots of the sliding buckle 79 may be provided with protrusions (e.g., teeth) such as to provide better retaining surfaces.

At the other end of the sliding buckle 79 there is provided the adjustment strap 72$_x$. One end portion of the adjustment strap 72$_x$ is attached to the facepiece 12 of the mask 10 as will be further described below. An opposite end portion 87 of the adjustment strap 72$_x$ is first inserted from the bottom into the slot 83$_2$ and looped back around and inserted from the top into the slot 83$_1$. Through this arrangement of the adjustment strap 72$_x$, the end portion 87 of the adjustment strap 72$_x$ can be pulled frontwardly (i.e. as indicated by the arrow in FIG. 12C) in order to adjust a length between a lower portion of the cap 70 and the facepiece 12, thereby tightening or loosening the mask 10 on the wearer's head.

In other embodiments, an inverse configuration may be used such that the adjustment straps 72$_1$, 72$_2$ may be pullable backwardly (i.e., towards a back of the wearer's head) to tighten the mask 10 when it is donned.

The harness 18 may be connected to the facepiece 12 in any suitable way. In this embodiment, besides the adjustment straps 72$_1$, 72$_2$, the harness 18 is connected to the facepiece 12 via a plurality of connecting straps 76$_1$-76$_4$ extending between the cap 70 and the facepiece 12. Anchors 77$_1$-77$_6$ are provided on a periphery of the facepiece 12 for receiving the connecting straps 76$_1$-76$_4$ and the adjustment straps 72$_1$, 72$_2$. In this embodiment, each of the anchors 77$_1$-77$_6$ comprises an opening 81 on the periphery of the facepiece 12. The connecting straps 76$_1$-76$_4$ and the adjustment straps 72$_1$, 72$_2$ are thus looped around the openings 81 of the anchors 77$_1$-77$_6$ and stitched to themselves or alternatively joined to themselves through any other suitable process (e.g., ultrasonic welding or adhesive bonding). In this embodiment, each anchor 77$_x$ comprises an anchoring element 84 (e.g., a grommet) embedded within the rubber material 28 of the facepiece 12 about the opening 81 of the anchor 77$_x$ (e.g., the rubber material 28 may be overmolded onto the anchoring element 84). The anchoring element 84 is stiffer than the rubber material 28 of the facepiece 12 to reinforce the anchor 77$_x$, but, as it is embedded in the rubber material 28, this may help to reduce or eliminate pressure points on the head of the wearer by avoiding direct contact with hard parts.

Thus the connecting straps 76$_1$-76$_4$ and the adjustment straps 72$_1$, 72$_2$ may be attached to the anchors 77$_1$-77$_6$ in a manner similar to that described regarding attachment between the strap 89 and the buckle 79. For instance, each connecting strap 76$_x$ may be inserted into an anchor 77$_x$, looped back around and joined to a remainder of the strap 76$_x$ in any suitable manner (e.g., stitching, ultrasonic welding or adhesive bonding).

Figure 13A:
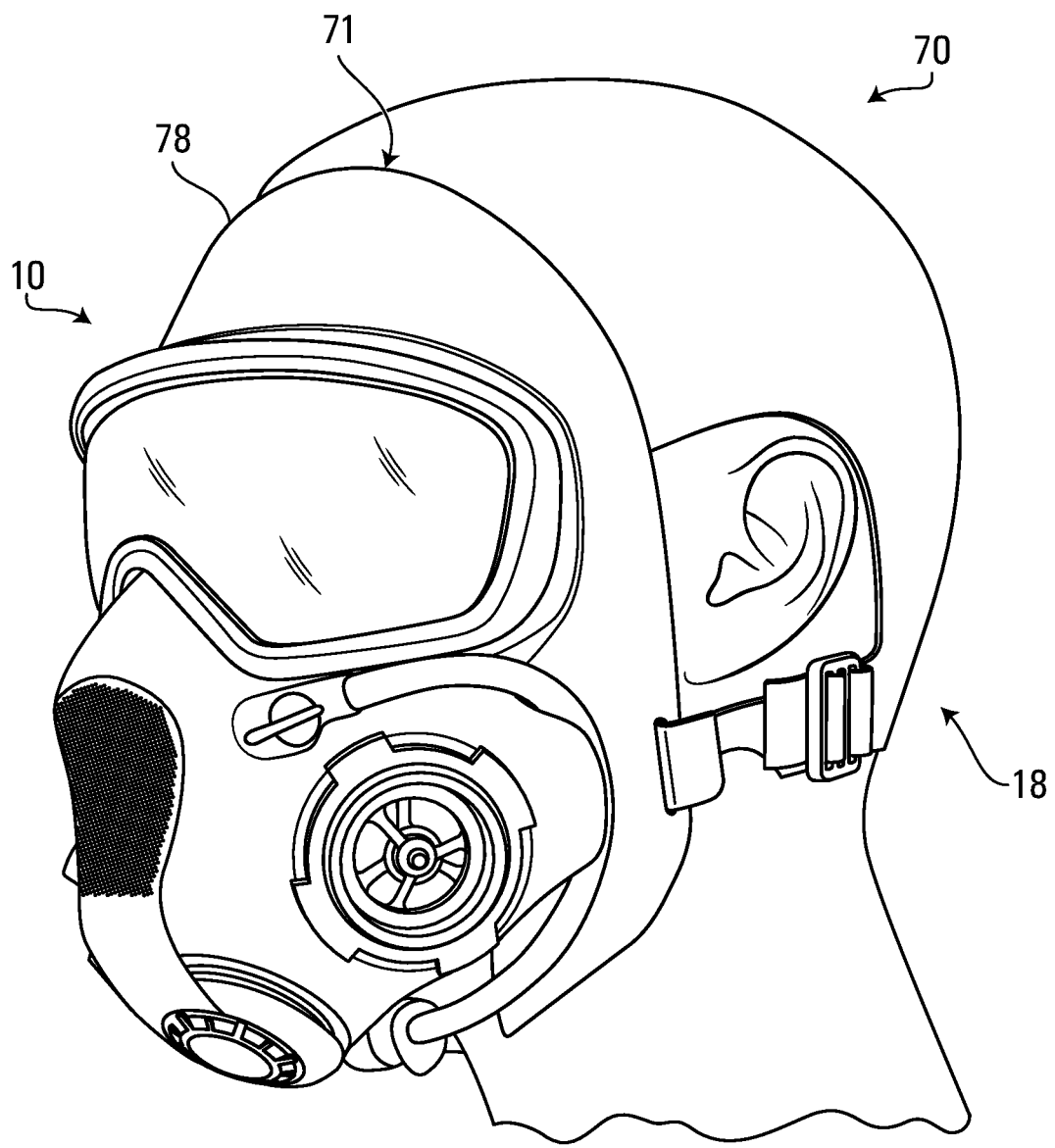
FIGS. 13A, 13B and 14 to 16 show variants of the harness in accordance with other embodiments of the invention.
Figure 13B:
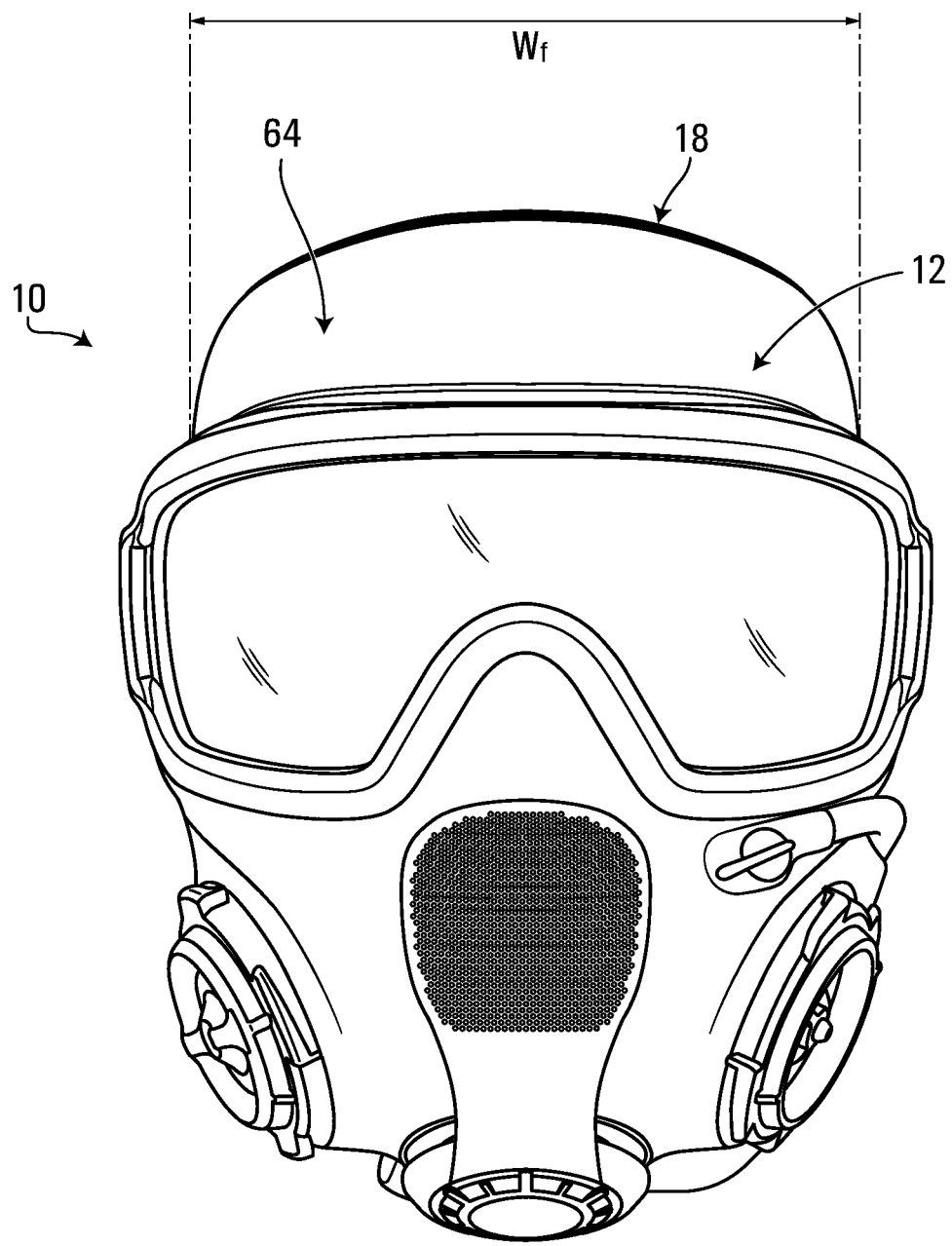

In other embodiments, as shown in FIGS. 13A and 13B, there may be a continuous connection between the harness 18 and a top edge portion 78 of the facepiece 12. This may facilitate wearing of the mask 10 under a helmet or a hood and/or eliminate or reduce any gap between the top edge portion 78 of the facepiece 12 and the harness 18 (e.g., to better protect the wearer's head).

More particularly, in this embodiment, the harness 18 extends to the facepiece 12 along at least a majority of a width W$_f$ of a forehead portion 64 of the facepiece 12. The forehead portion 64 of the facepiece 12 is that portion of the facepiece 12 that overlies the wearer's forehead when the mask 10 is worn. In this example of implementation, the harness 18 extends to the facepiece 12 along at least three-quarters of, in this case along an entirety of, the width W$_f$ of the forehead portion 64 of the facepiece 12. Thus, in this embodiment, there is no gap between the harness 18 and the forehead portion 64 of the facepiece 12.

Figure 14:
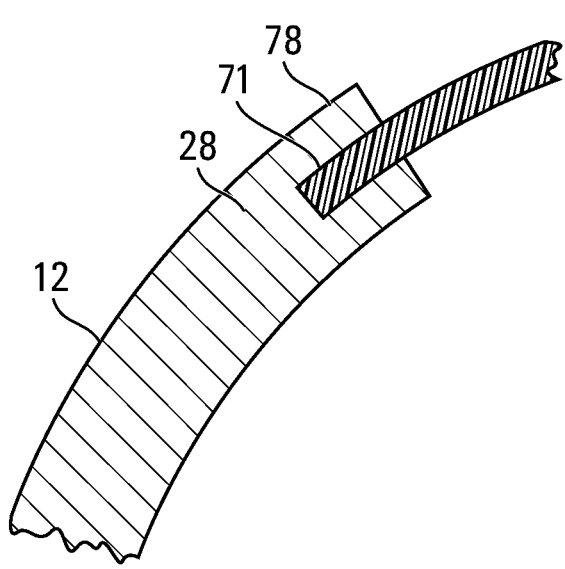
Figure 15:
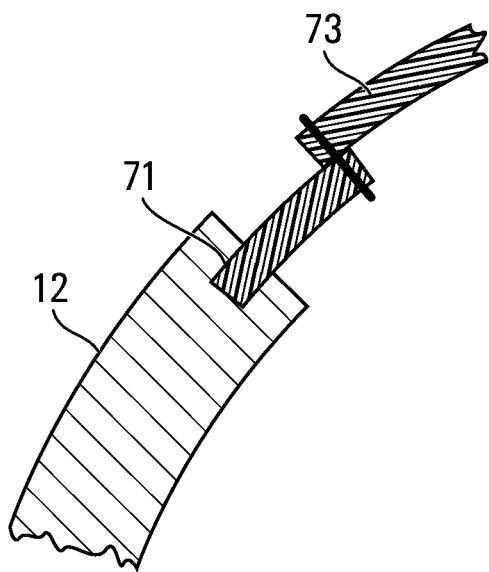
Figure 16:
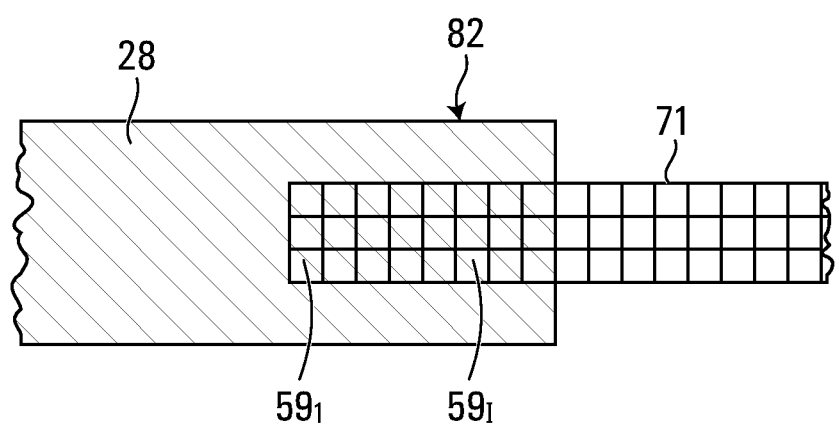

For example, in some embodiments, as shown in FIGS. 14 to 16, the rubber material 28 of the top edge portion 78 of the facepiece 12 may be overmolded onto a fabric member 71 of the cap 70. The rubber material 28 flows into interstices 59$_1$-59$_I$ of the fabric member 71 (i.e., spaces between fibers, which may be spaces between fibers of adjacent strands, yarns, or other elongated fabric elements, of the fabric member 71) where it is captured to mechanically interlock the rubber material 28 and the fabric member 71 at an overmolded joint 82.

In some examples, as shown in FIG. 14, the fabric member 71 of the cap 70 may constitute at least a bulk (i.e., a bulk or an entirety) of the cap 70. Alternatively, in other examples, as shown in FIG. 15, the fabric member 71 of the cap 70 may be separate from and stitched or otherwise joined to another fabric member 73 of the cap 70 which constitutes a bulk of the cap 70.

The harness 18 may be implemented (e.g., shaped, constructed, etc.) in various other ways in other embodiments.

In this embodiment, a weight distribution of the mask 10 makes it easier to wear and reduce its burden on the wearer. Notably, in this example, a weight of the mask 10 is distributed such that there is less of a tendency for the mask 10 to drag the wearer's head forward than conventional masks.

More particularly, in this embodiment, with additional reference to FIG. 17A, a center of gravity CG$_M$ of the mask 10 is closer to a center of gravity CG$_H$ of the wearer's head when the mask 10 is worn than conventional masks. For example, a distance D$_{cg}$ between the center of gravity CG$_M$ of the mask 10 and the center of gravity CG$_H$ of the wearer's head represented by a standard headform according to ISO/TS 16976-2:2010 of the International Organization for Standardization (ISO) may be no more than 85 mm, in some cases no more than 83 mm, in some cases no more than 81 mm, and in some cases even less (e.g., 80 mm or less). In this example of implementation, the distance D$_{cg}$ between the center of gravity CG$_M$ of the mask 10 and the center of gravity CG$_H$ of the wearer's head is about 79.8 mm.

Also, in this embodiment, with additional reference to FIGS. 17B and 17C, a profile of the mask 10 is closer to the center of gravity CG$_H$ of the wearer's head or the wearer's face when the mask 10 is worn than conventional masks. For example, as shown in FIG. 17B, a greatest distance D$_{p1}$ from the mask 10 to the center of gravity CG$_H$ of the wearer's head represented by a standard headform according to ISO/TS 16976-2:2010 (i.e., that distance from the center of gravity CG$_H$ of the wearer's head to a point F$_M$ of the mask 10 that is farthest from the center of gravity CG$_H$ of the wearer's head) may be no more than 175 mm, in some cases no more than 170 mm, in some cases no more than 165 mm, and in some cases even less. As another example, as shown in FIG. 17C, a horizontal distance D$_{p2}$ between a frontmost point P$_M$ of the mask 10 and a frontmost point P$_H$ of the wearer's head represented by a standard headform according to ISO/TS 16976-2:2010 may be no more than 27 mm, in some cases no more than 25 mm, in some cases no more than 23 mm, and in some cases even less (e.g., no more than 21 mm).

Figure 18:
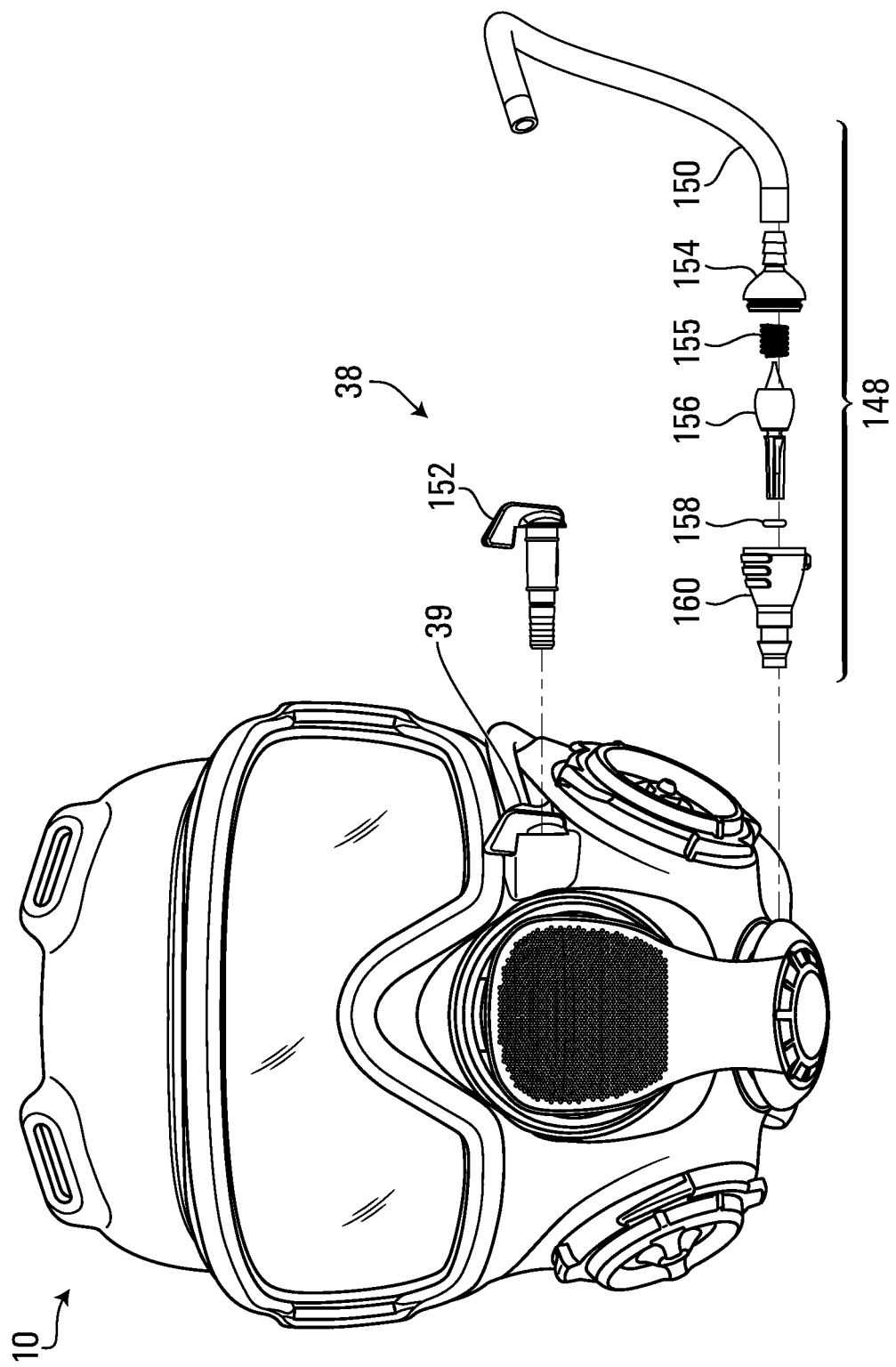
FIGS. 18 and 19 show a hydration interface of the respirator mask.
Figure 19:
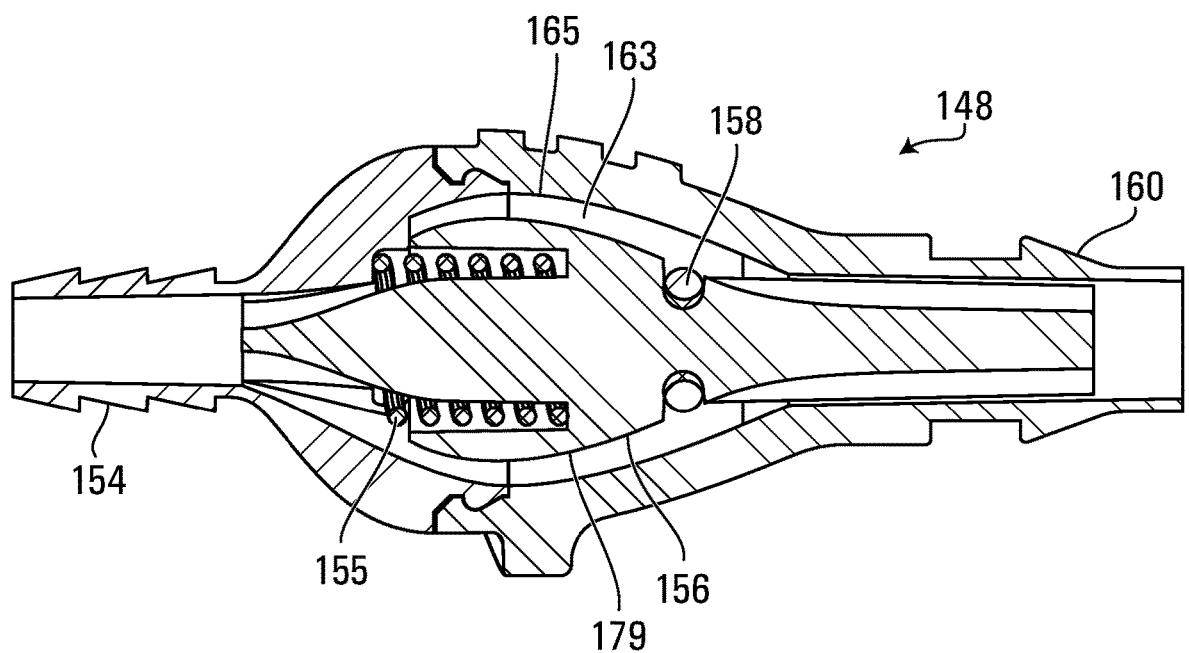

The hydration interface 38 is configured to provide potable water or other liquid to the wearer. In this embodiment, with additional reference to FIGS. 18 and 19, the hydration interface 38 comprises a liquid port 39, a straw 150, a valve 152 and an actuating mechanism 148. The actuating mechanism 148 comprises: a straw connector 154, a biasing member 155, a movable member 156, a sealing element 158 and a suction member 160. In this embodiment, a channel 163 of the hydration interface 38 has a curved, i.e., streamlined, configuration in a direction of liquid flow through the hydration interface 38 that may help to enhance liquid flow or reduce liquid flow resistance when the wearer drinks. An outer surface 179 of the movable member 156 and an inner surface 165 of the suction member 160 are curved in the direction of liquid flow. More particularly, in this embodiment, the outer surface 179 of the movable member 156 and the inner surface 165 of the suction member 160 are streamlined.

The hydration interface 38 may be implemented (e.g., configured, constructed, etc.) in various other ways in other embodiments.

Figure 20A:
FIGS. 20A, 20B and 21 show a speech transmitter of the respirator mask.
Figure 20B:
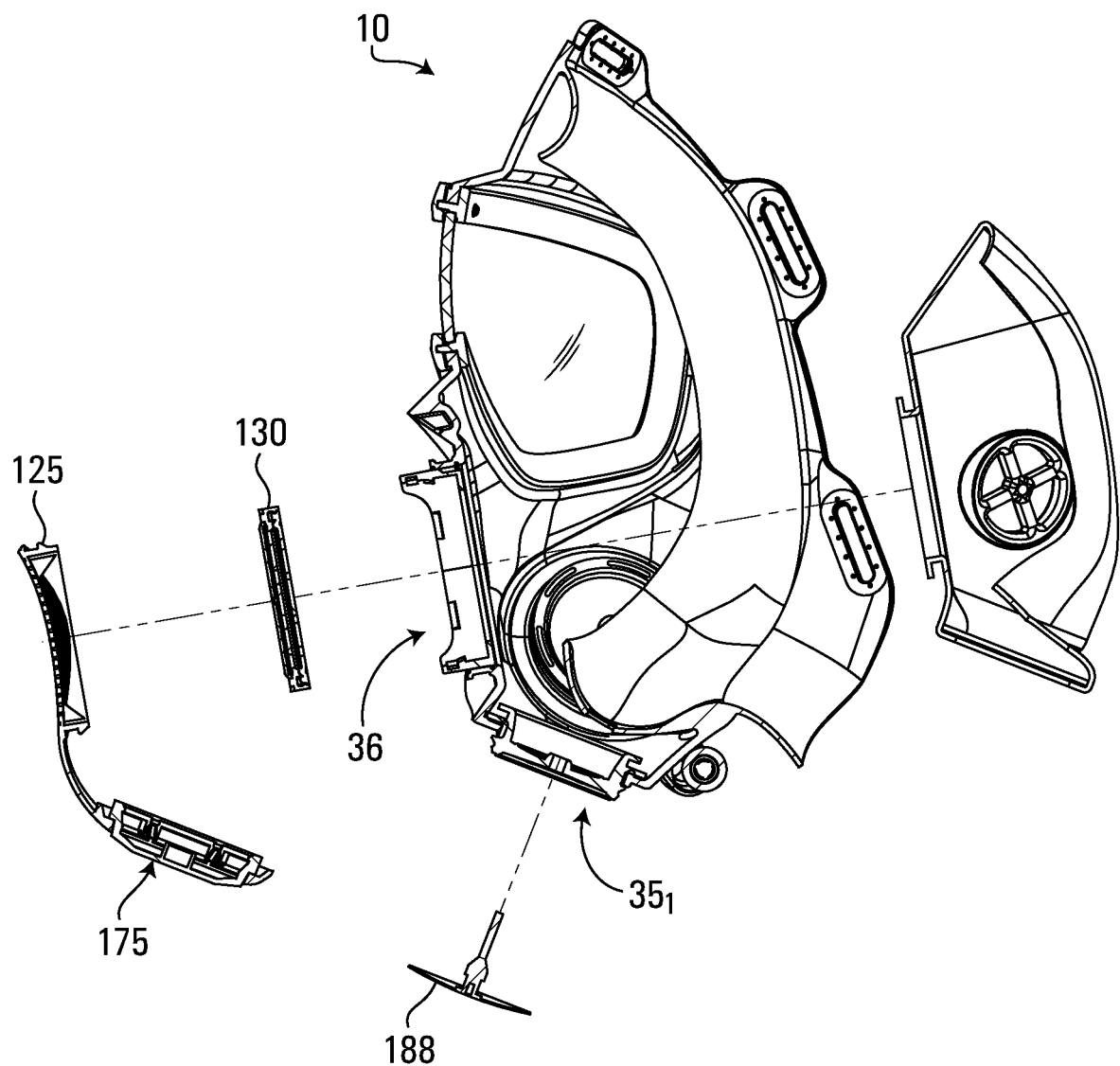
Figure 21:
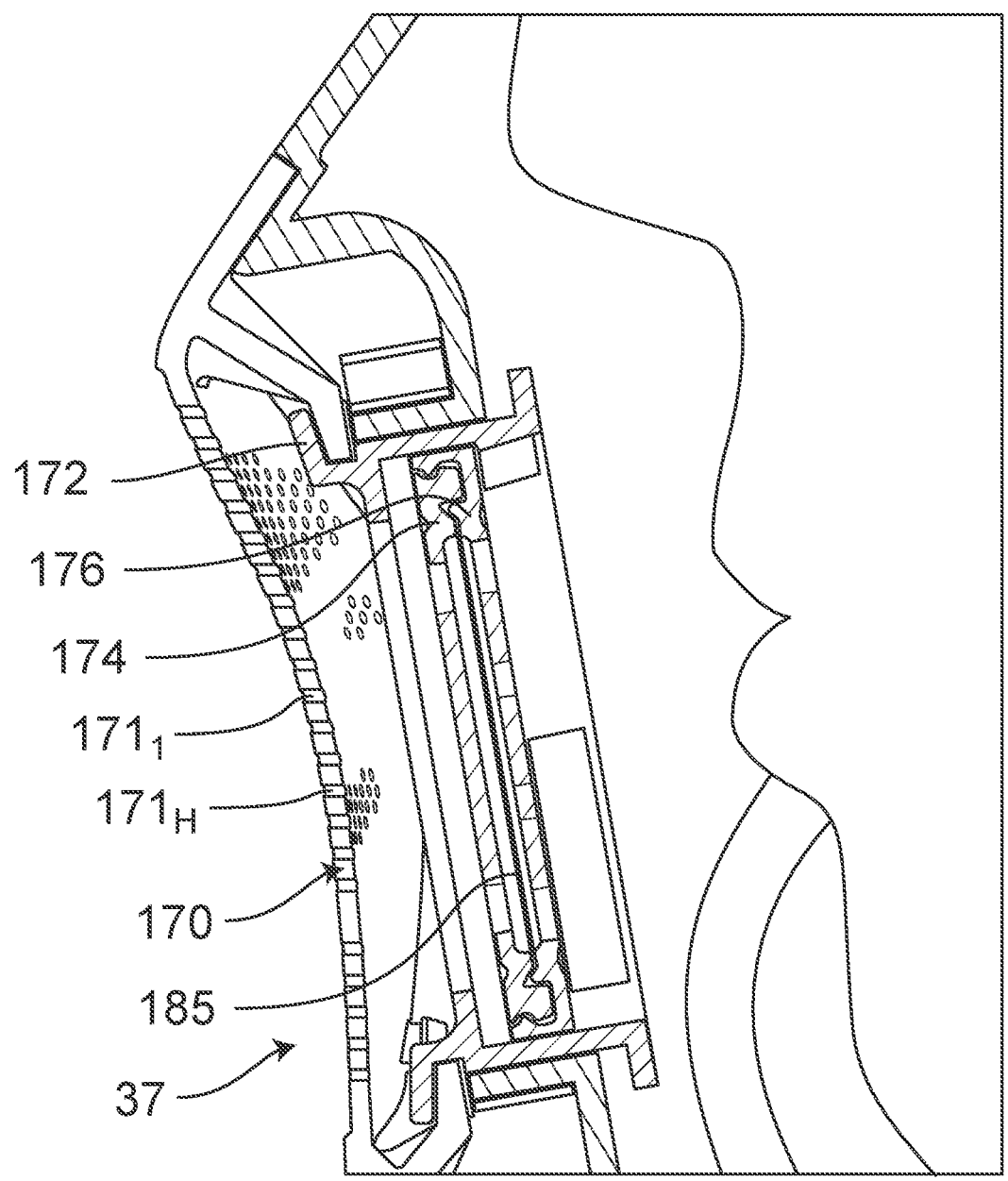

The speech transmitter 37 is configured to transmit the wearer's speech. To this end, in this embodiment, with additional reference to FIGS. 20A to 21, the speech transmitter 37 comprises a speech-transmission unit 130 and a cover 125 disposed within the opening 36 of the mask 10. In this example of implementation, the speech-transmission unit 130 comprises a membrane 185 configured to vibrate in response to vocal sound emitted by the wearer in order to transmit the vocal sound. In this case, the membrane 185 is made of a polyimide material (e.g., A Kapton™ film). The membrane 185 may be made of any other suitable material in other cases. The membrane 185 is mounted to a support 186 of the speech-transmission unit 130. In this case, the support 186 comprises a first support member 174 and a second support member 176 between which the membrane 185 is mounted. The cover 125 enables transmission of sound through a sound-transmitting portion 170 comprising a set of small holes $171_1$-$171_H$. The holes $171_1$-$171_H$ thus allow the transmission of the wearer's speech into the wearer's environment.

The speech transmitter 37 may be implemented (e.g., configured, constructed, etc.) in various other ways in other embodiments. For example, in some embodiments, the speech transmitter 37 may comprise a speech amplifier for amplifying a speech of the wearer, thus providing a greater range of communication to the wearer. In some embodiments where speech transmission is not a priority or silence is preferred, the mask 10 may not comprise any speech transmitter at all.

As shown in FIGS. 34 to 37C, in some embodiments, the mask 10 may comprise a speech transmitter 137 that is attachable to and detachable from the mask 10. That is, the mask 10 and the speech transmitter 137 are designed such that the speech transmitter 137 can be readily attached to and detached from the mask 10 by the wearer (or another individual). In this example, the speech transmitter 137 may be attached to the mask 10 in addition to the speech transmitter 37 to enhance transmission of the wearer's speech.

In this embodiment, the speech transmitter 137 is attachable to and detachable from either of the mounts $56_1$, $56_2$ of the breathing interface 16. For instance, in this example, the speech transmitter 137 is attached to the mount $56_2$ while the filter 52 is mounted to the mount $56_1$.

To that end, in this embodiment, the speech transmitter 137 comprises a connector 140 connectable to a given one of the connectors $58_1$, $58_2$ of the mount $56_2$. More particularly, in this embodiment, the connector 140 is connectable to the connector $58_2$ of the mount $56_2$. In this example, the connector 140 comprises interlocking elements $310_1$-$310_i$ which are meshable with the interlocking elements $69_1$-$69_i$ of the connector $58_2$. The speech transmitter 137 may thus be connected to the filter mount $56_2$ by pushing the speech transmitter 137 into the mount $56_2$ and subsequently turning the speech transmitter 137 in a similar manner to that described above in regard of mounting the filter 53 to the mount $56_x$. In order to actuate the valve 65 of the mount $56_2$, the speech transmitter 137 comprises a valve-engaging member 380 configured for engaging the seal 108 and thus the movable closure 102 of the valve 65 of the mount $56_2$. In this embodiment, the valve-engaging member 380 is generally cylindrical and comprises a recess in a central portion of its outer peripheral surface.

Figure 35:
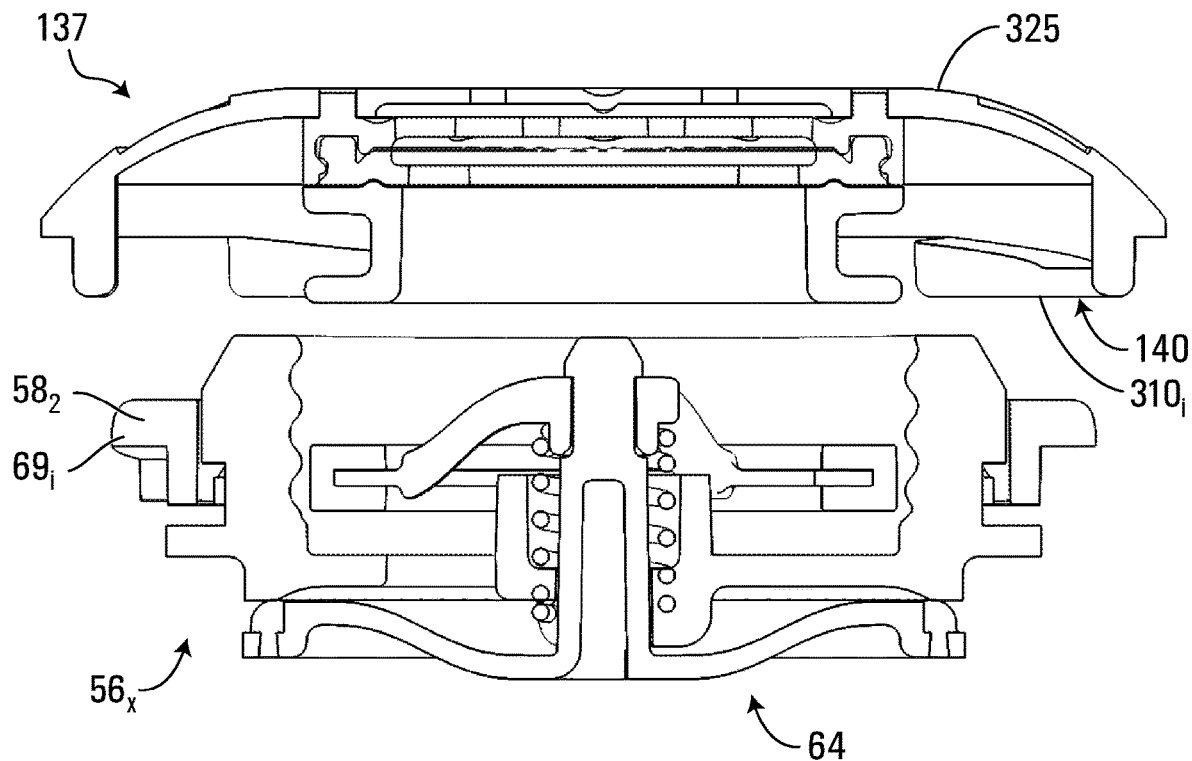
FIGS. 35 and 36A to 36C show the speech transmitter being mounted to the mount of the breathing interface.
Figure 36A:
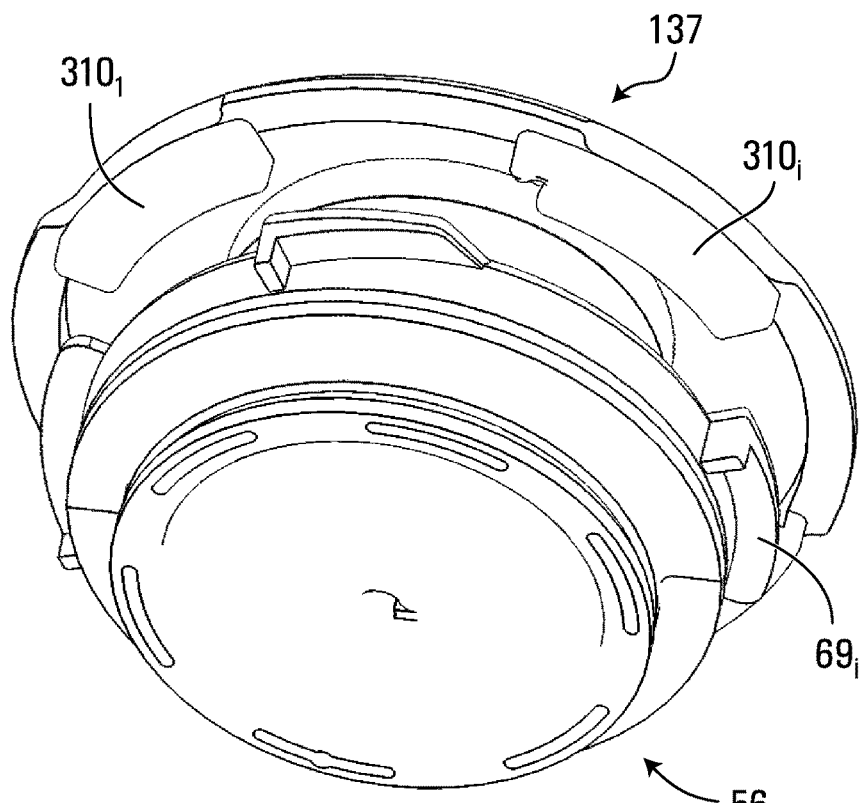
Figure 36B:
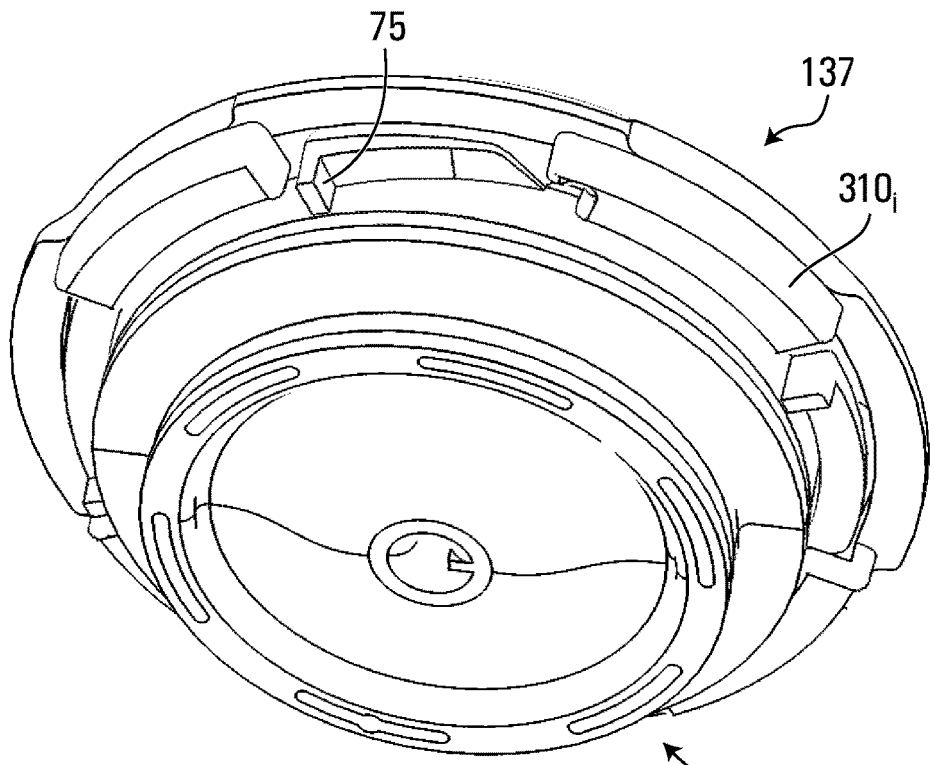
Figure 36C:
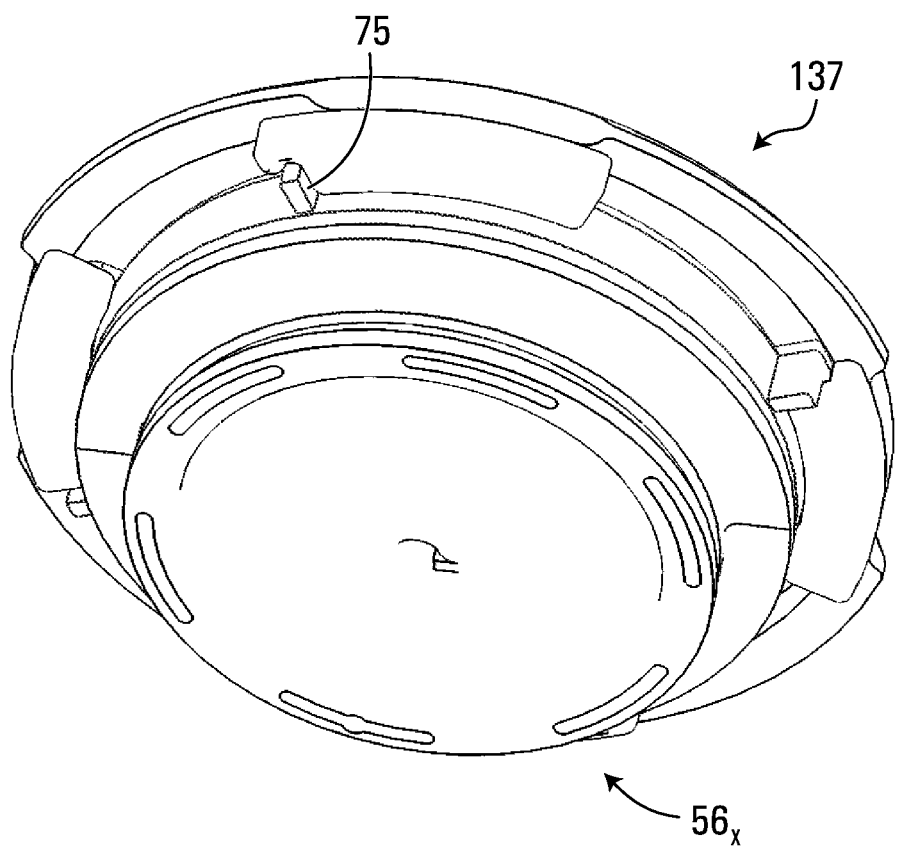

Thus, in use, with additional reference to FIGS. 35 to 36C, the wearer of the mask 10 (or another individual) wishing to mount the speech transmitter 137 to the mount $56_2$ first aligns the interlocking elements $310_1$-$310_i$ of the connector 140 with the connector $58_2$ such that the interlocking elements $69_1$-$69_i$ of the connector $58_2$ do not interfere with an inward movement of the connector 140. The speech transmitter 137 is then pushed inwardly towards the mask 10. Upon actuating the valve 65 by engagement of its valve-engaging member 380 with the valve 65, the speech transmitter 137 is then turned (e.g., in a clockwise direction) such that the interlocking elements $310_1$-$310_i$ of the connector 140 slideably mesh with the interlocking elements $69_1$-$69_i$ of the connector $58_2$. This turn of the speech transmitter 137 is less than a complete rotation (i.e., less than 360°), which makes for a quick connection, in contrast to a screwing action requiring multiple full rotations. For instance, in some embodiments, a turn of less than 180°, in some cases less than 120°, in some cases less than 90° may be used to secure the speech transmitter 137 to the filter mount $56_2$ (e.g., a one-eighth turn, a quarter turn, or a half-turn). As shown in FIG. 36C, the abutment 75 of each of the interlocking elements $69_1$-$69_i$ then stops the sliding motion of the interlocking elements $310_1$-$310_i$. At this point, the speech transmitter 137 is safely secured to the mount $56_2$ and the valve 65 is in its open state. As such, speech transmission is enabled through the speech transmitter 137.

In order to dismount the speech transmitter 137 from the mount $56_2$, the speech transmitter 137 is turned in an opposite direction (e.g., a counterclockwise direction) to cause the interlocking elements $310_1$-$310_i$ to disengage from the interlocking elements $69_1$-$69_i$. The speech transmitter 137 is then pulled outwardly from the mount $56_2$. As the speech transmitter 137 is pulled away, the valve 65 acquires its closed state.

In a variant, the connector 140 of the speech transmitter 137 may be configured differently such as to be connectable to the connector $58_1$ of the mount $56_2$. For instance, instead of comprising the interlocking elements $310_1$-$310_i$, the connector 140 may comprise a thread disposed on the outer peripheral surface of the valve-engaging member 380 and complementary to the thread 61 of the connector $58_1$. The thread of the connector 140 of the valve-engaging member 380 is thus operable to engage the thread 61 of the connector $58_1$. In such an instance, the outer peripheral surface of the valve-engaging member 380 may not comprise a recess. In this variant, the speech transmitter 137 is mounted to the mount $56_2$ by being screwed into the mount $56_2$. More specifically, the threaded connector 140 is screwed into the connector $58_1$. This screwing action eventually leads to the valve-engaging member 380 contacting the seal 108, after which further screwing causes the valve-engaging member 380 to drive the seal 108, the support 104 and the movable closure 102 of the valve 65 inwards while the biasing member 106 is compressed. Once the valve-engaging rim 115 has driven the support 104 to its bottom position within the frame 100, the speech transmitter 137 is fully locked into the filter mount $56_2$. At this point, the valve 65 is in its open state and the transmission of speech is enabled through the speech transmitter 137.

In this variant, in order to dismount the speech transmitter 137 from the filter mount $56_2$, the valve-engaging member 380 is unscrewed from the connector $58_2$. As the valve-engaging member 380 is unscrewed, the valve 65 acquires its closed state.

Figure 33:
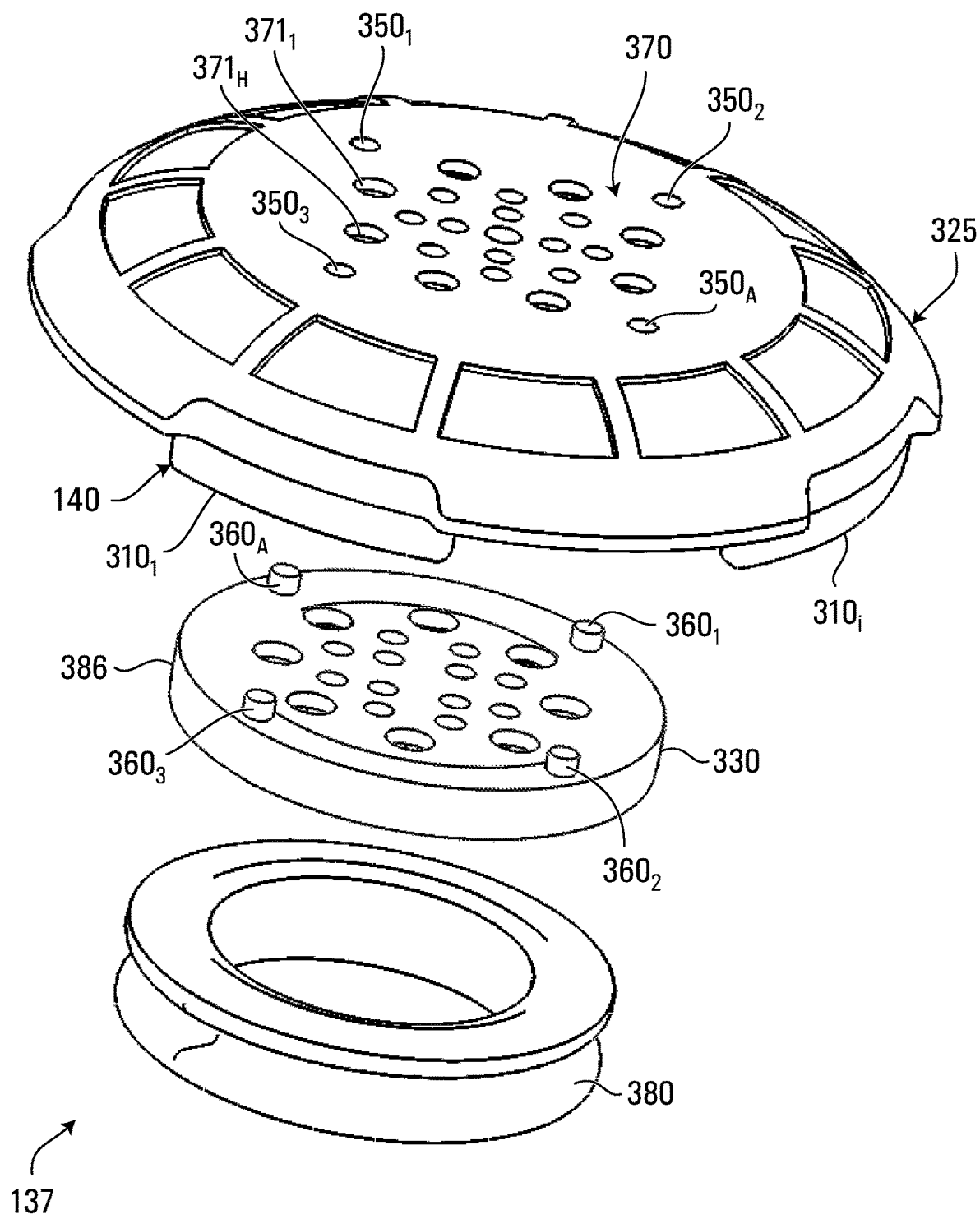
FIGS. 33 and 34 show a speech transmitter mountable to the mount of the breathing interface.
Figure 34:
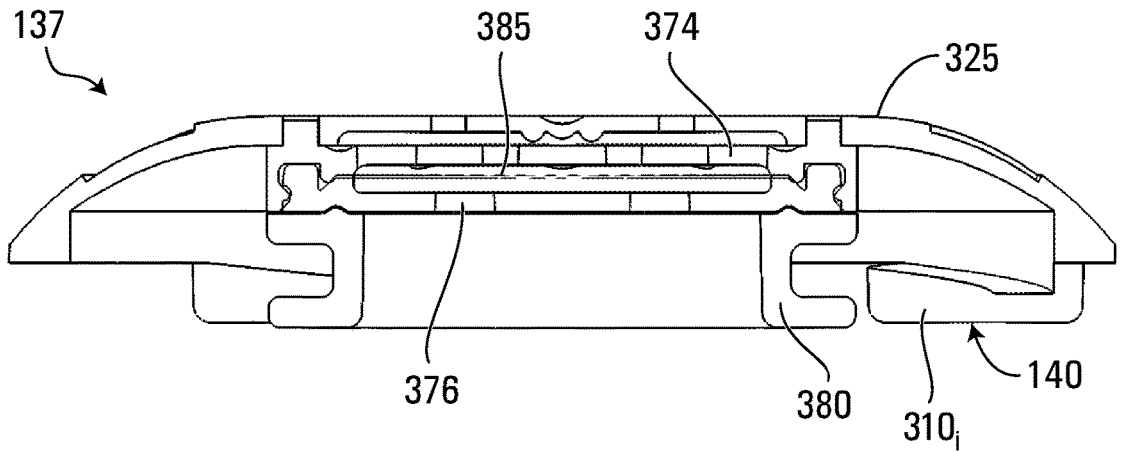

In this embodiment, with additional reference to FIGS. 33 and 34, additional to the connector 140 and the valve-engaging member 380, the speech transmitter 137 comprises a speech-transmission unit 330 and a cover 325. In this example of implementation, the speech-transmission unit 330 comprises a membrane 385 configured to vibrate in response to vocal sound emitted by the wearer in order to transmit the vocal sound. In this case, the membrane 385 is made of a polyimide material (e.g., a Kapton™ film). The membrane 385 may be made of any other suitable material in other cases. The membrane 385 is mounted to a support 386 of the speech-transmission unit 330. In this case, the support 386 comprises a first support member 374 and a second support member 376 between which the membrane 385 is mounted. Furthermore, the support 386 comprises protrusions $360_1$-$360_A$ for engaging the cover 325. The cover 325 enables transmission of sound through a sound-transmitting portion 370 comprising a set of holes $371_1$-$371_H$. The holes $371_1$-$371_H$ thus allow the transmission of the wearer's speech into the wearer's environment. In addition, the cover 325 comprises apertures $350_1$-$350_A$ for receiving and engaging the protrusions $360_1$-$360_A$ of the support 386. Moreover, the speech-transmission unit 330 is disposed between the cover 325 and the valve-engaging member 380.

The speech transmitter 137 may be implemented (e.g., configured, constructed, etc.) in various other ways in other embodiments. For example, in some embodiments, the speech transmitter 137 may comprise a speech amplifier for amplifying a speech of the wearer, thus providing a greater range of communication to the wearer.

In this embodiment in which the facepiece 12 comprises the rubber material 28 molded into shape, certain functional components $80_1$-$80_R$ of the mask 10, including a conduit (e.g., the liquid port 39) of the hydration interface 38, the anchoring element 84 of each of the anchors $77_1$-$77_6$ and/or another part (e.g., the cap 70) of the harness 18, a part (e.g., the frame 100) of each of the filter mounts $56_1$, $56_2$, a part (e.g., the frame 190) of the outlet assembly 175, a part (e.g., the frame) of the speech transmitter 37, etc., are provided and secured to the facepiece 12 during molding of the facepiece 12. More particularly, in this embodiment, the rubber material 28 of the facepiece 12 is overmolded onto the functional components $80_1$-$80_R$ of the mask 10. This may create a better hermetic joint and seal for these functional components $80_1$-$80_R$.

Figure 22:
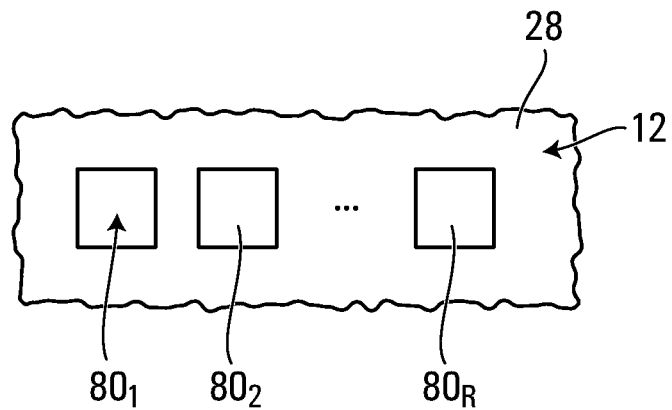
FIGS. 22 and 23 show a polymeric material of the facepiece overmolded onto functional components of the respirator mask.
Figure 23:
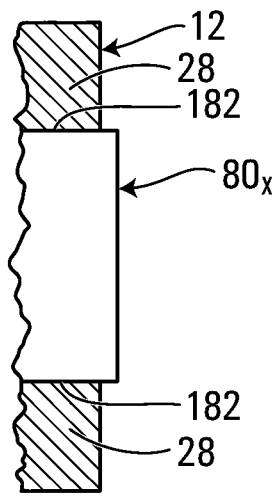

With additional reference to FIGS. 22 and 23, overmolding the rubber material 28 of the facepiece 12 onto a functional component $80_x$ of the mask 10 forms an overmolded joint 182 between the rubber material 28 and the functional component $80_x$. The overmolded joint 182 is a mechanical interlock in which the rubber material 28 and the functional component $80_x$ are mechanically interlocked. That is, the rubber material 28 and the functional component $80_x$ are interconnected via the rubber material 28 extending into one or more hollow spaces (e.g., apertures, recesses, interstices, etc.) and/or around one or more parts (e.g., a perimeter, one or more ridges or other projections, etc.) of the functional component $80_x$ during molding to create the overmolded joint 182. In some cases, a surface treatment (e.g., a primer, a corona plasma treatment, etc.) may be applied to the functional component $80_x$ to enhance bonding with the rubber material 28 when it is overmolded.

In embodiments discussed above where the rubber material 28 of the mask's top edge portion is overmolded onto a fabric member 71 of the cap 70 of the harness 18, as shown in FIG. 16, during the overmolding process, the rubber material 28 flows into the interstices $59_1$-$59_I$ of the fabric member 71 where it is captured to mechanically interlock the rubber material 28 and the fabric member 71 at the overmolded joint 82, which is an example of the overmolded joint 182.

One or more of the functional components $80_1$-$80_R$ of the mask 10 may be secured to the facepiece 12 in any other suitable way in other embodiments. For example, in other embodiments, one or more of the functional components $80_1$-$80_R$ of the mask 10 may be adhesively bonded to the facepiece 12 by a suitable adhesive, welded (e.g., ultrasonically) to the facepiece 12, or fastened by one or more mechanical fasteners (e.g., screws, bolts, etc.)

The mask 10 may be configured and/or made in any other suitable way in other embodiments.

Figure 24:
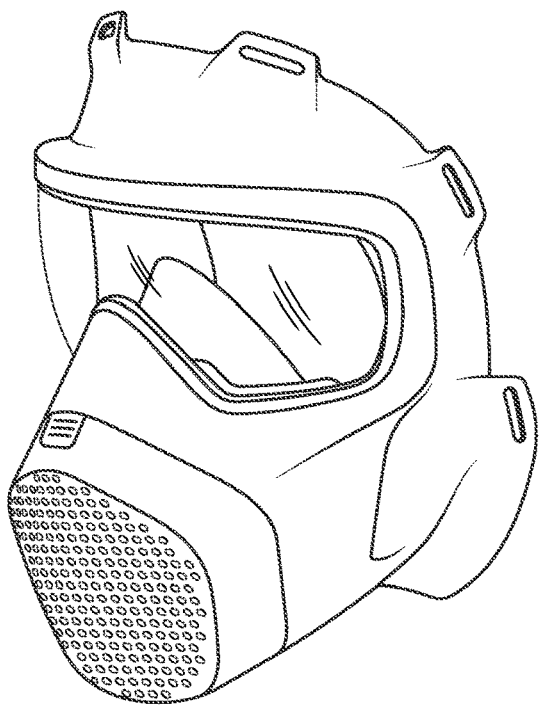
FIGS. 24 and 25 show a variant of the respirator mask having a conforming filter in accordance with another embodiment of the invention.
Figure 25:

For example, FIGS. 24 and 25 show another embodiment of the mask 10. In this embodiment, some aspects of the mask 10 are designed similarly to that of other embodiments described previously, including the visor 14, the harness 18, the hydration interface 38, and the mask's weight distribution. Other aspects of the mask 10 are designed differently in this embodiment, including the facepiece 12 and the breathing interface 16.

Figure 26A:
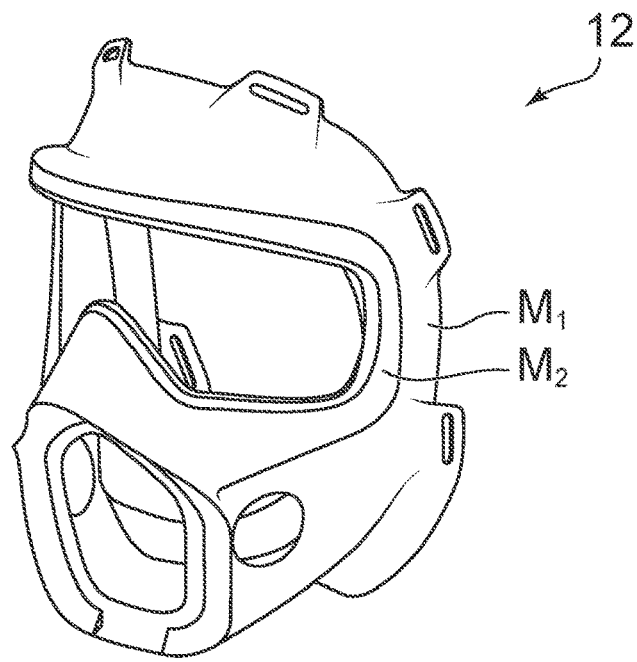
FIGS. 26A to 26C show the facepiece of the respirator mask of FIGS. 24 and 25 and portions of the facepiece made of different materials.
Figure 26B:
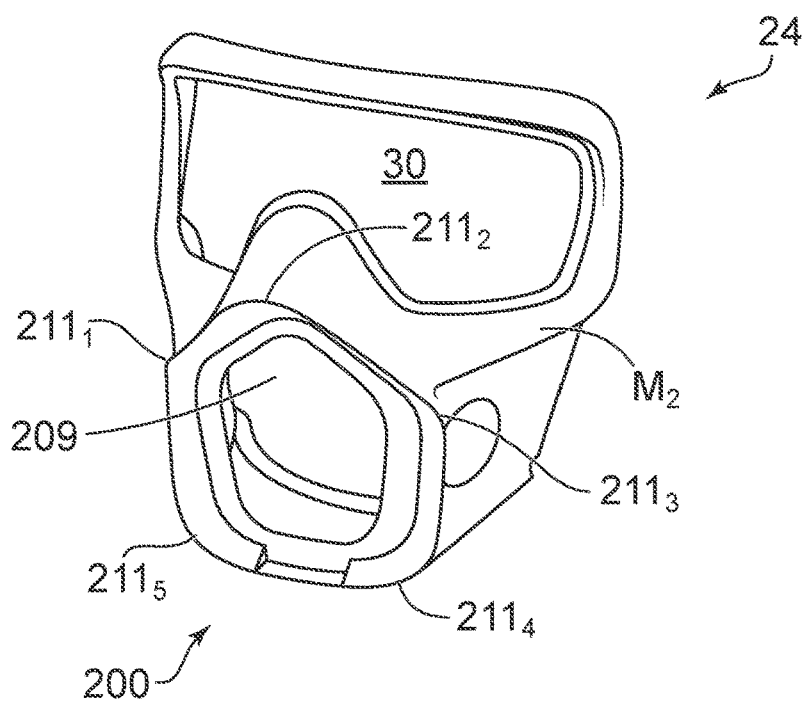
Figure 26C:
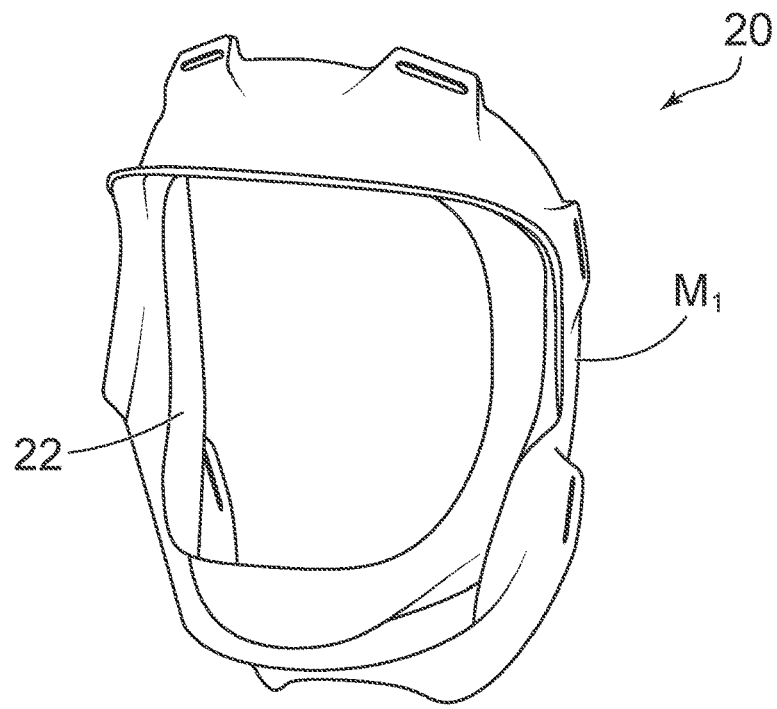

In this embodiment, with additional reference to FIGS. 26A to 26C, the facepiece 12 is made of a plurality of different materials $M_1$, $M_2$ having different properties. This may help to reduce the weight of the mask 10 and/or tailor protection, comfort, and other performance characteristics of the mask 10. The different materials $M_1$, $M_2$ may belong to different classes or types of materials (e.g., elastomers, non-elastomeric polymers, textiles or other fabrics, metals, composites, etc.) and/or may exhibit substantially different values of a given property (e.g., modulus of elasticity, hardness, density, noxious fluid penetration resistance, heat loss capability, breathability, etc.).

More particularly, in this embodiment, the face-engaging portion 20 of the facepiece 12, which engages the wearer's face, is made of the material $M_1$, while the support portion 24 of the facepiece 12, which supports the visor 14, the breathing interface 16, and the hydration interface 38, is made of the material $M_2$. In this example, the material $M_1$ is (1) softer and/or more elastic and (2) denser than the material $M_2$. This allows the face-engaging portion 20 to comfortably engage the wearer's face, while the support portion 24 can reduce the weight of the mask 10.

For instance, in some embodiments, a ratio $H_1/H_2$ of a hardness $H_1$ of the material $M_1$ over a hardness $H_2$ of the material $M_2$ may be no more than 0.95, in some cases no more than 0.9, and in some case no more than 0.85. As another example, in some embodiments, a ratio $E_1/E_2$ of a modulus of elasticity $E_1$ of the material $M_1$ over a modulus of elasticity $E_2$ of the material $M_2$ may be no more than 0.95, in some cases no more than 0.9, and in some case no more than 0.85. As yet another example, in some embodiments, a ratio $\rho_1/\rho_2$ of a density $\rho_1$ of the material $M_1$ over a density $\rho_2$ of the material $M_2$ may be at least 1.05, in some cases at least 1.1, and in some case at least 1.15. Differences in these properties of the materials $M_1$, $M_2$ may take on any other suitable value in other embodiments.

In this example of implementation, the material $M_1$ making up the face-engaging portion 20 is an elastomeric material, while the material $M_2$ making up the support portion 24 is a non-elastomeric polymeric material. More particularly, in this example, the elastomeric material $M_1$ is a rubber material and the non-elastomeric polymeric material $M_2$ is a non-elastomeric thermoplastic material. In this case, the rubber material $M_1$ is bromobutyl rubber (e.g., BIIR TSE) and the non-elastomeric thermoplastic material $M_2$ is high-density polyethylene (HDPE). Any other suitable materials may be used in other examples (e.g., the material $M_1$ may be any other suitable rubber compound, the material $M_2$ may be polybutylene terephthalate or any other suitable material).

The different materials $M_1$, $M_2$ of the facepiece 12 are hermetically joined. More particularly, in this embodiment, the different materials $M_1$, $M_2$ may be bonded by an adhesive such as, for example, a reactive hot-melt polyurethane adhesive or any other suitable adhesive (e.g., a polyolefin reactive hot-melt or cyanoacrylate adhesive). In other embodiments, the materials $M_1$, $M_2$ may be joined through other joining processes such as, for example, by overmolding the materials $M_1$, $M_2$, by ultrasonic welding the materials $M_1$, $M_2$ or by any other suitable joining process.

In this embodiment, at least part of the facepiece 12, including the HDPE material $M_2$, is surface treated to make it resistant to ingress of noxious agents. More particularly, in this embodiment, at least part of the facepiece 12 is surface treated by a surface fluorination process which may impart a higher level of resistance to chemicals. Other surface treatments (e.g., coatings, plasma deposition, etc.) may be used in other embodiments.

Although the facepiece 12 is made of two different materials $M_1$, $M_2$ in this embodiment, the facepiece 12 may be made of three or more different materials in other embodiments.

Figure 27:
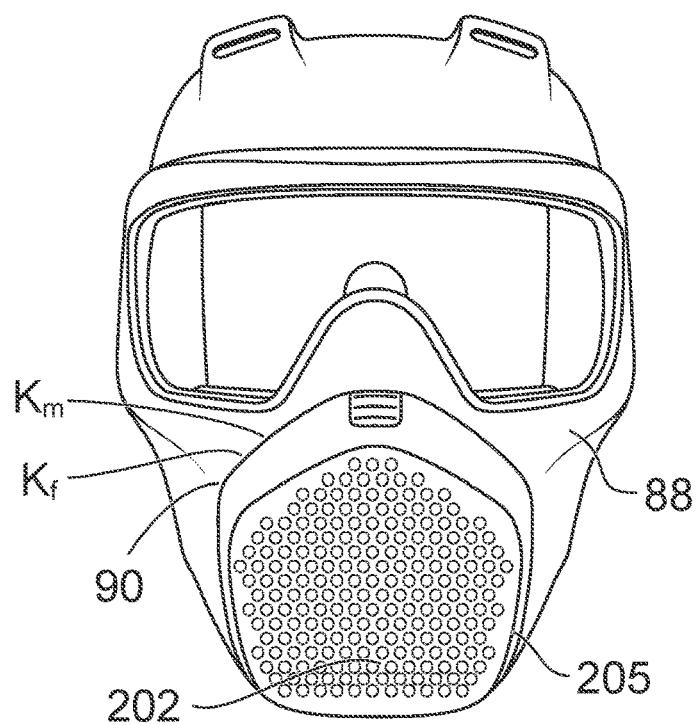
FIGS. 27 to 29 show the conforming filter in relation to the facepiece of the respirator mask of FIGS. 24 and 25.
Figure 28:
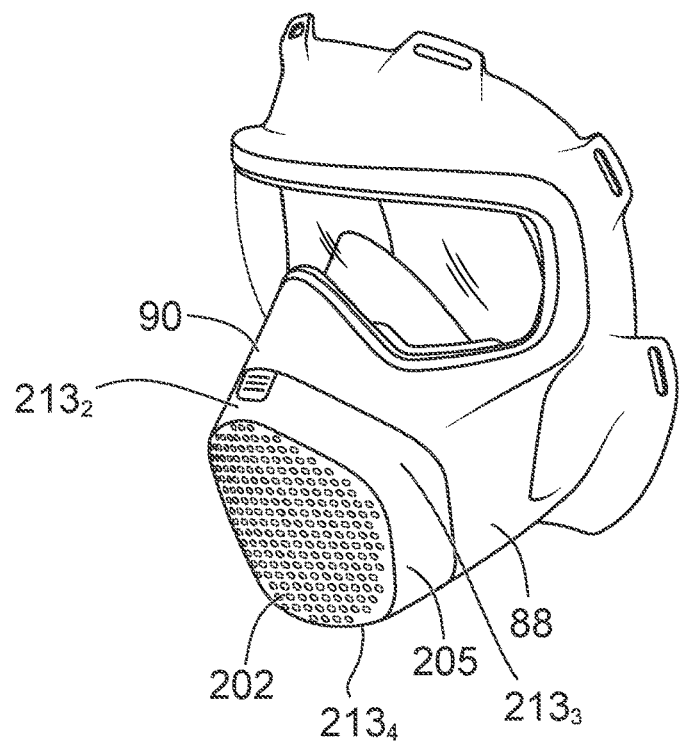
Figure 29:
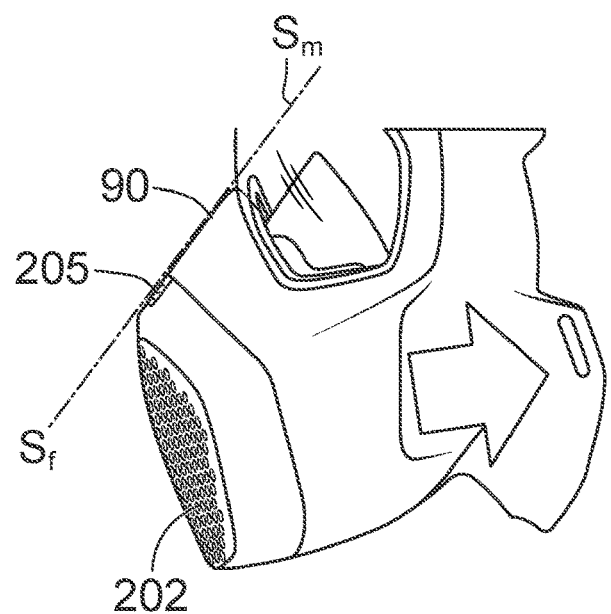
Figure 30A:
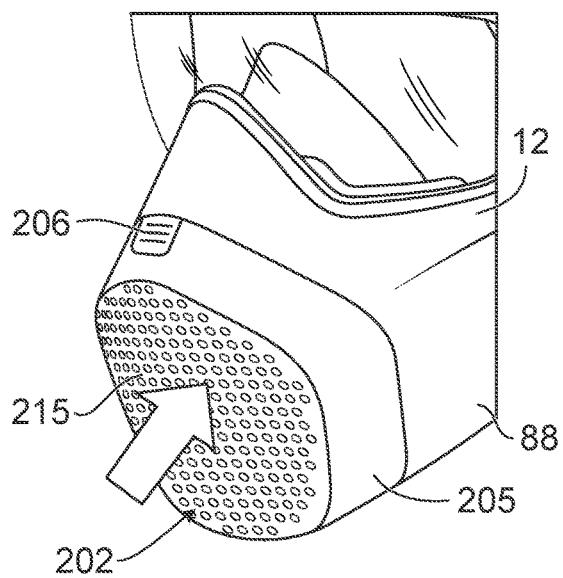
Figure 30B:
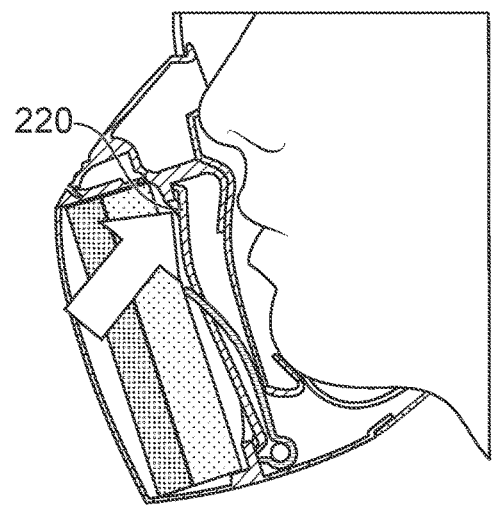
Figure 30C:
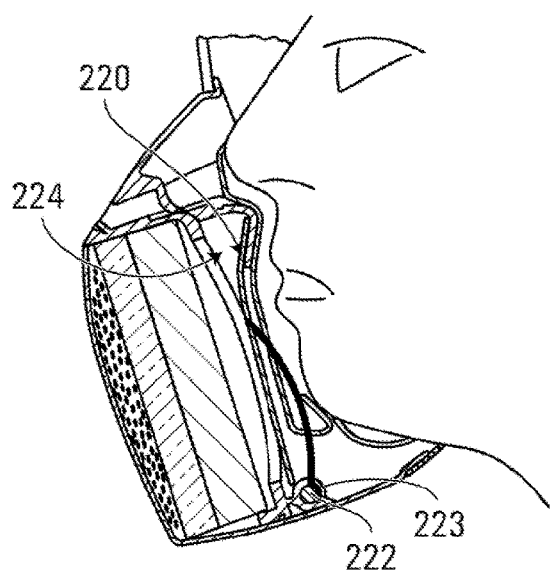
Figure 30D:
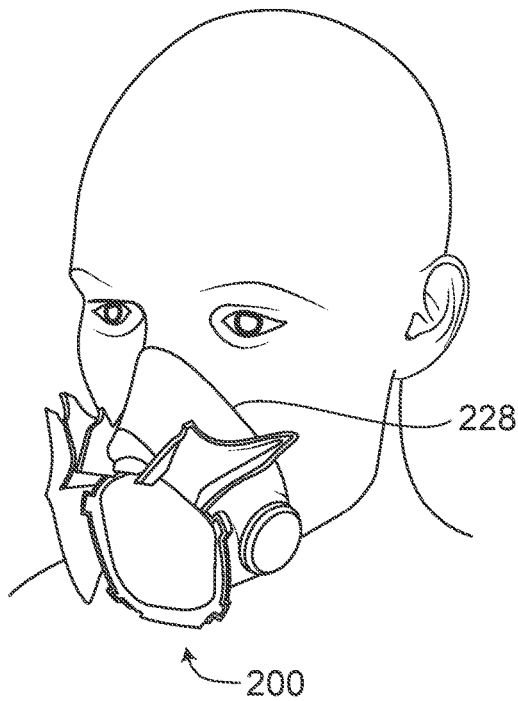
Figure 30I:
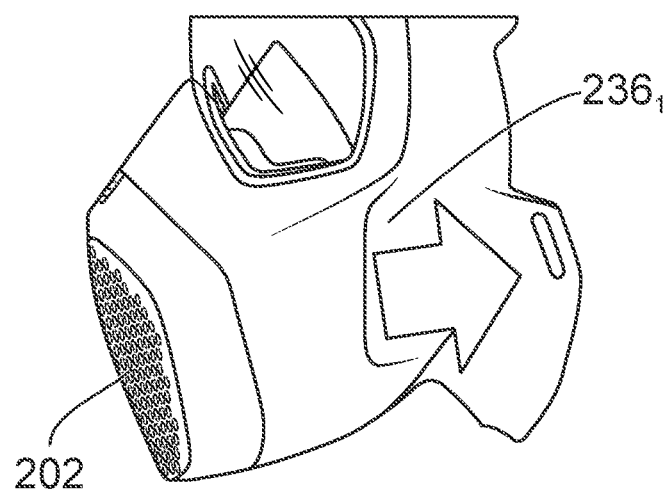
Figure 31:
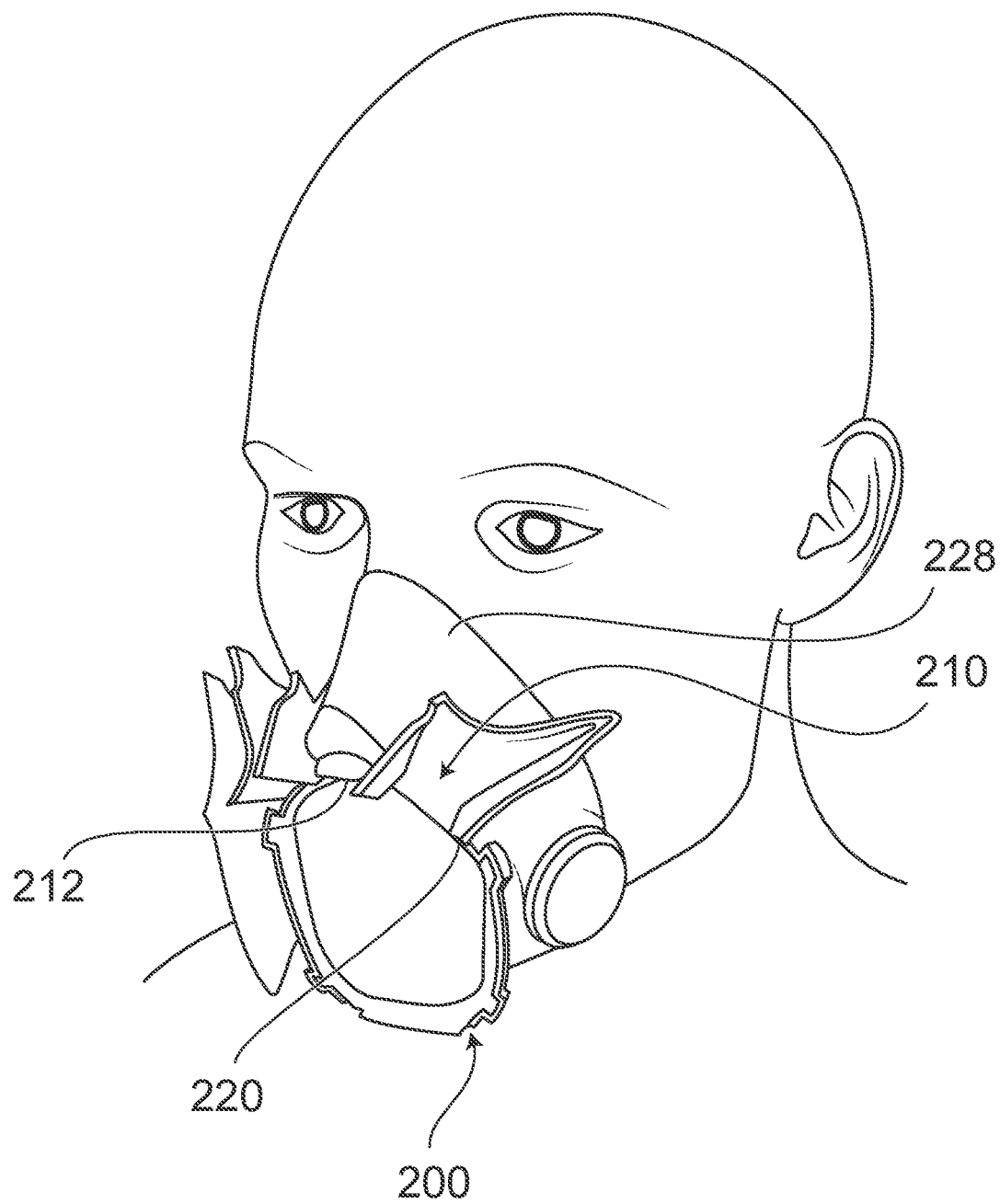
FIG. 31 shows a filter mount of the respirator mask of FIGS. 24 and 25.
Figure 32:
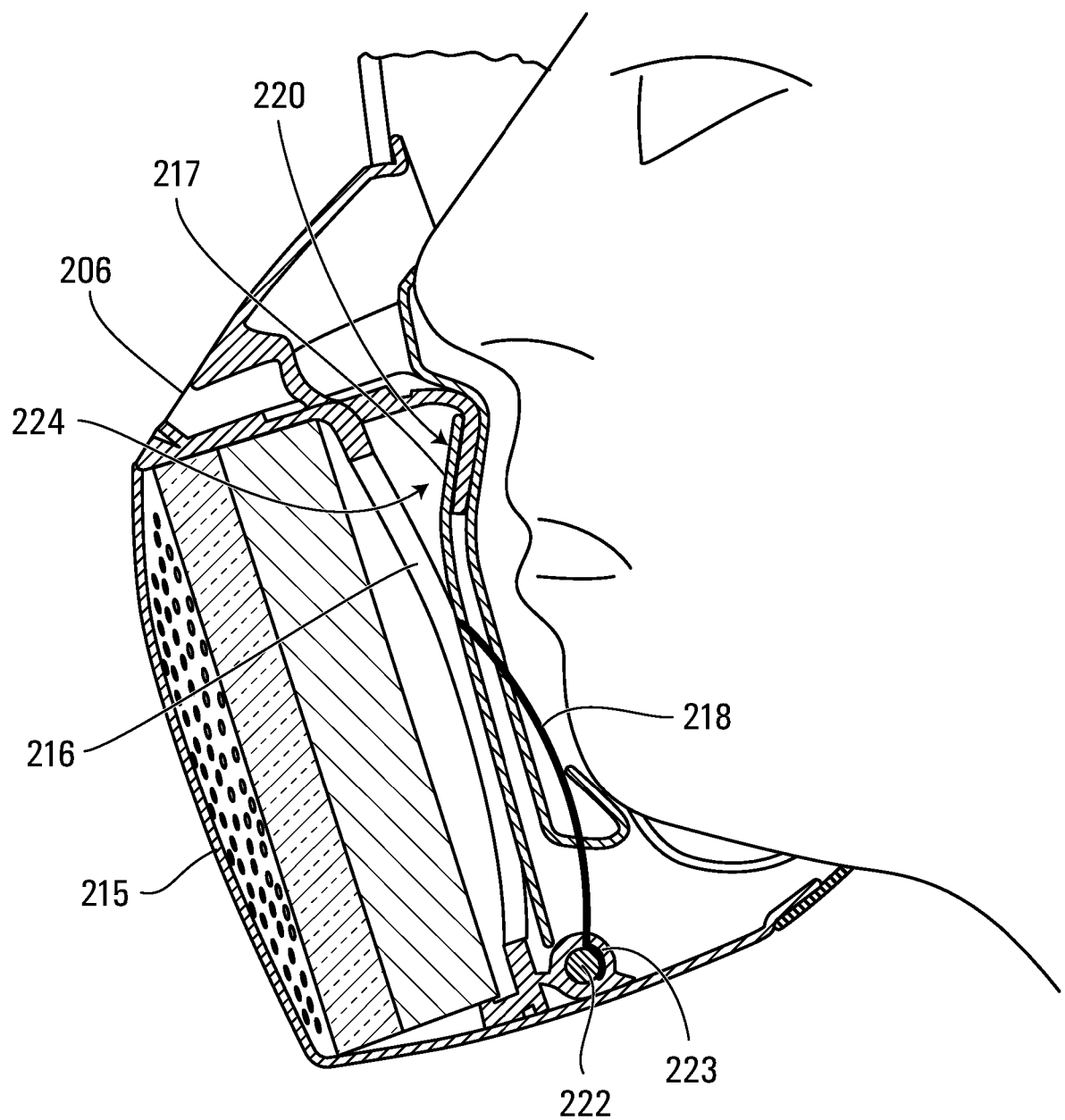
FIG. 32 shows a cross-sectional side view of the conforming filter mounted to the filter mount of the respirator masks of FIGS. 24 and 25.

In this embodiment, with additional reference to FIGS. 27 to 29, the breathing interface 16 comprises a filter mount 200 for mounting a conforming filter 202 to the mask 10. The conforming filter 202 is "conforming" in that it conforms to part of an external surface 88 of the facepiece 12 when mounted to the filter mount 200. That is, the conforming filter 202 comprises an external surface 205 facing outwardly away from the wearer and aligning with an adjacent portion 90 of the external surface 88 of the facepiece 12 when mounted to the filter mount 200. For example, in this embodiment, a tangent $S_f$ to the external surface 205 of the conforming filter 202 and a tangent $S_m$ to the adjacent portion 90 of the external surface 88 of the facepiece 12 are substantially parallel to one another when the conforming filter 202 is mounted to the filter mount 200.

More particularly, in this embodiment, the filter mount 200 is centered on the mask 10 such that the conforming filter 202 is mountable in a central region of the mask 10. The filter mount 200 comprises a cavity 209 that overlaps the wearer's nose and mouth when the mask 10 is worn. When mounted to the filter mount 200, the conforming filter 202 therefore also overlaps the wearer's nose and mouth.

Also, in this embodiment, the external surface 205 of the conforming filter 202 substantially merges with the adjacent portion 90 of the external surface 88 of the facepiece 12 to visually form a continuity of the external surface 88 of the facepiece 12.

For example, in this embodiment, the external surface 205 of the conforming filter 202 is contiguous with the adjacent portion 90 of the external surface 88 of the facepiece 12. Furthermore, a curvature of the external surface 205 substantially matches a curvature of the adjacent portion 90 of the external surface 88 of the facepiece 12 at the filter mount 200. Also, as shown in FIG. 27, a perimeter $K_f$ of the external surface 205 of the conforming filter 202 substantially matches a perimeter $K_m$ of the external surface 88 of the facepiece 12 at the filter mount 200. In this embodiment, the perimeter $K_m$ of the external surface 88 of the facepiece 12 is generally polygonal, extending rectangularly in a lateral direction and forming an apex at a nose region of the facepiece 12. Accordingly, the perimeter $K_1$ of the conforming filter 202 defines a similar shape. Thus, bends $211_1$-$211_5$ in the perimeter $K_m$ of the external surface 88 of the facepiece 12 at the filter mount 200 are aligned with bends $213_1$-$213_5$ in the perimeter $K_f$ of the conforming filter 202 at the filter mount 200.

As another example, in this embodiment, the external surface 205 of the conforming filter 202 continues a surface "trend" of the external surface 88 of the facepiece 12. For example, in this embodiment, a tapering trend of the external surface 88 of the facepiece 12 is continued by the external surface 205 of the conforming filter 202. More specifically, in this embodiment, the external surface 88 of the facepiece 12 has a centrally tapering trend, i.e. tapers towards a central point of the filter mount 200. Thus, accordingly, the external surface 205 of the conforming filter 202 continues the centrally tapering trend of the external surface 88 of the facepiece 12 such that there are no disruptions in the trend of a combined surface comprising the external surface 88 of the facepiece 12 and the external surface 205 of the conforming filter 202.

In this embodiment, the conforming filter 202 is mountable to the filter mount 200 by being pushed into the filter mount 200. More particularly, the conforming filter 202 is a "quick-connect" filter that can be easily and quickly mounted onto the filter mount 200. To this end, the conforming filter 202 is a clip-on filter equipped with a push-button 206.

The conforming filter 202 is operable to engage a connector 210 of the filter mount 200. In this embodiment, the connector 210 comprises a protrusion 212 and a valve 220. In this example, the valve 220 comprises a sealing member 217, a lip 218, a hinge 222 about which the valve 220 rotates, and a torsion spring 223 connected to the lip 218 for providing a torsional force to the sealing member 217. To mount the conforming filter 202 to the filter mount 200, a slot at the bottom of the conforming filter 202 is first aligned with the facepiece 12 and the conforming filter 202 is pushed against the filter mount 200 such that its inner surface 216 engages the sealing member 217 of the valve 220. The push-button 206 engages the protrusion 212 while the inner surface 216 of the conforming filter 202 pushes the sealing member 217 inwards causing the sealing member 217 to rotate about the hinge 222 against a resistance applied by the torsion spring 223. Consequently, this produces a gap 224 which allows the entry of air into the mask 210. The push-button 206 engages the protrusion 212 of the connector 210 such as to lock the conforming filter 202 in place while at a bottom of the conforming filter 202, the slot provided therein assures secure engagement to the facepiece 12. At this point, the conforming filter 202 is securely mounted to the filter mount 200 and the valve 220 is in an open position. To disengage the conforming filter 202 from the filter mount 200, the push-button 206 is pressed downwards. This causes the conforming filter 202 to release the connector 210 which allows for retraction of the conforming filter 202 from the filter mount 200.

The connector 210 of the filter mount 200 and the conforming filter 202 may be configured in any other suitable way in other embodiments to allow connection and disconnection of the conforming filter 202 to and from the filter mount 200.

The conforming filter 202 may be implemented in any suitable way. For example, in some embodiments, the conforming filter 202 may comprise a filtering material including active particles (e.g., activated carbon) or any other suitable material, as discussed previously in connection with the filters 52, 53. Any other suitable construction may be used for the conforming filter 202 in other embodiments.

With additional reference to FIGS. 30A to 30I, in this embodiment, airflow within the mask 10 can be directed in a controlled path to reduce resistance to air ingress and egress and reduce humidity inside the mask 10. More particularly, in this embodiment, air circulation within the mask 10 occurs according to a sequence of steps as follows.

First, air enters the conforming filter 202 through a holed surface 215 of the conforming filter 202. Upon travelling through the conforming filter 202, the now filtered air flows through the gap 224 which was created by the valve 220 of the filter mount 200. The filtered air enters the facepiece 12 and is subsequently directed into an upper portion of an inner cavity 230 of the facepiece 12. The filtered air then circulates within the inner cavity 230, going around a secondary seal 228 (e.g., a nosecup) and finally enters the secondary seal 228 via apertures 232 located beneath the secondary seal 228. The wearer then breathes in the filtered air. Once the wearer exhales, the exhaled air is expulsed through outlet ports $234_1$, $234_2$ located on each lateral side of the secondary seal 228. Finally, the exhaled air is led through cavities $236_1$, $236_2$ positioned on each lateral side of the facepiece 12 and out into the environment.

The circulation of the air within the facepiece 12 may help to freshen the wearer's skin and consequently reduce the thermal burden on the wearer. In addition, circulation of the air within the cavity 230 may help to mitigate fogging of the visor 214.

While in this embodiment the filter mount 200 is centered on the mask 10 such that the conforming filter 202 is mountable in the central region of the mask 10, the filter mount 200 may be located elsewhere on the mask 10, such as on a lateral side of the mask 10 (e.g., similar to where either of the filter mounts $56_1$, $56_2$ is located in embodiments previously considered), and the conforming filter 202 may be configured to conform to that other region of the facepiece 12. Also, in some embodiments, there may be an additional filter mount similar to the filter mount 156 for mounting an additional conforming filter similar to the conforming filter 202. For instance, in some embodiments, the filter mount 200 and the additional similar filter mount may be located on opposite lateral sides of the mask 10 (e.g., similar to where the filter mounts $56_1$, $56_2$ are located in embodiments previously considered), and the conforming filter 202 and the additional similar filter may be configured to conform to these regions of the facepiece 12.

Any feature of any embodiment discussed herein may be combined with any feature of any other embodiment discussed herein in some examples of implementation.

Certain additional elements that may be needed for operation of certain embodiments have not been described or illustrated as they are assumed to be within the purview of those of ordinary skill in the art. Moreover, certain embodiments may be free of, may lack and/or may function without any element that is not specifically disclosed herein.

Although various embodiments and examples have been presented, this was for the purpose of describing, but not limiting, the invention. Various modifications and enhancements will become apparent to those of ordinary skill in the art and are within the scope of the invention, which is defined by the appended claims.

The invention claimed is:

1. A method of manufacturing a respirator mask for protecting a wearer against inhalation of noxious agents, the method comprising:
providing a facepiece;
connecting a visor to the facepiece; and
attaching a filter mount to the facepiece, the filter mount configured to allow a plurality of different types of filters to be mounted to the filter mount,
wherein the different types of filters include (1) a threaded filter that is screwable into the filter mount and (2) a threadless filter that is mountable to the filter mount without being screwed into the filter mount.

2. The method of claim 1, wherein the filter mount includes a threaded connector for connecting the threaded filter and a threadless connector for connecting the threadless filter.

3. The method of claim 1, wherein the visor is removable from the respirator mask.

4. The method of claim 1, further comprising providing a speech transmitter to at least one of the facepiece or the filter mount.

5. The method of claim 1, comprising a selector to selectively change the respirator mask between a negative-pressure mode and a positive-pressure mode.

6. The method of claim 1, wherein the visor comprises:
a lens that is panoramic;
a rigid material providing ballistic protection; and
a compound curvature such that the lens is curved in a plurality of different directions.

7. The method of claim 1, wherein the threadless filter is mountable to the filter mount by being pushed into the filter mount.

8. The method of claim 1, wherein the threadless filter is mountable to the filter mount by turning the threadless filter by less than a complete rotation in the filter mount.

9. The method of claim 1, wherein the different types of filters include (1) a standard NATO threaded filter and (2) a filter different from the standard NATO threaded filter.

10. The method of claim 1, wherein the filter mount comprises a valve to regulate airflow within the respirator mask.

11. The method of claim 10, wherein the valve comprises a movable closure, and a biasing member tending to move the movable closure to close the valve.

12. The method of claim 10, wherein the valve is configured to remain open while the filter is connected to the filter mount.

13. The method of claim 10, wherein the valve is configured to automatically close in response to the filter being disconnected from the filter mount.

14. The method of claim 1, wherein the facepiece includes:
a face-engaging portion configured to engage with a wearer's face; and
a support portion supporting the visor and the filter mount,
wherein the face-engaging portion includes a first material, and the support portion includes a second material that is different from the first material.

15. The method of claim 14, wherein the first material at least one of an elastomeric material or a rubber material, and the second material is at least one of a non-elastomeric polymeric material or a non-elastomeric thermoplastic material.

16. The method of claim 14, wherein the first material is overmolded onto the second material.

* * * * *